(12) United States Patent
Schweich, Jr. et al.

(10) Patent No.: US 9,050,188 B2
(45) Date of Patent: Jun. 9, 2015

(54) METHODS AND SYSTEMS FOR HEART VALVE THERAPY

(71) Applicant: Caisson Interventional LLC, Maple Grove, MN (US)

(72) Inventors: Cyril J. Schweich, Jr., Maple Grove, MN (US); Todd J. Mortier, Maple Grove, MN (US)

(73) Assignee: Caisson Interventional, LLC, Maple Grove, MN (US)

( * ) Notice: Subject to any disclaimer, the term of this patent is extended or adjusted under 35 U.S.C. 154(b) by 0 days.

(21) Appl. No.: 14/268,076

(22) Filed: May 2, 2014

(65) Prior Publication Data
US 2015/0112427 A1 Apr. 23, 2015

Related U.S. Application Data

(60) Provisional application No. 61/894,766, filed on Oct. 23, 2013.

(51) Int. Cl.
*A61F 2/24* (2006.01)

(52) U.S. Cl.
CPC .............. *A61F 2/2409* (2013.01); *A61F 2/2427* (2013.01); *A61F 2/2418* (2013.01); *A61F 2230/0034* (2013.01); *A61F 2220/0016* (2013.01); *A61F 2/2436* (2013.01)

(58) Field of Classification Search
CPC ... A61F 2/2409; A61F 2/2418; A61F 2/2442; A61F 2/2445; A61F 2/2448
USPC ............ 623/1.24, 1.26, 2.17–2.18, 2.36–2.38
See application file for complete search history.

(56) References Cited

U.S. PATENT DOCUMENTS

| | | | |
|---|---|---|---|
| 4,680,031 A * | 7/1987 | Alonso | 623/2.13 |
| 5,423,887 A | 6/1995 | Love et al. | |
| 5,662,704 A | 9/1997 | Gross | |
| 5,855,601 A | 1/1999 | Bessler et al. | |
| 5,984,959 A | 11/1999 | Robertson et al. | |
| 6,113,631 A | 9/2000 | Jansen | |
| 6,296,662 B1 | 10/2001 | Caffey | |
| 6,309,417 B1 | 10/2001 | Spence et al. | |
| 6,332,893 B1 | 12/2001 | Mortier et al. | |
| 6,358,277 B1 | 3/2002 | Duran | |
| 6,530,952 B2 | 3/2003 | Vesely | |
| 6,569,196 B1 | 5/2003 | Vesely | |
| 6,582,462 B1 | 6/2003 | Andersen et al. | |
| 6,629,534 B1 | 10/2003 | St. Goar et al. | |

(Continued)

FOREIGN PATENT DOCUMENTS

WO  WO 2011/119101  9/2011

OTHER PUBLICATIONS

International Preliminary Report on Patentability and Written Opinion of the International Searching Authority in International Application No. PCT/US2013/036734, dated Oct. 21, 2014, 9 pages.

(Continued)

*Primary Examiner* — Andrew Iwamaye
*Assistant Examiner* — Leslie Lopez
(74) *Attorney, Agent, or Firm* — Fish & Richardson P.C.

(57) ABSTRACT

Systems and methods for medical interventional procedures, including approaches to valve implantation. In one aspect, the methods and systems involve a modular approach to mitral valve therapy.

20 Claims, 47 Drawing Sheets

(56) References Cited

U.S. PATENT DOCUMENTS

| | | |
|---|---|---|
| 6,767,362 B2 | 7/2004 | Schreck |
| 6,769,434 B2 | 8/2004 | Liddicoat et al. |
| 6,790,229 B1 | 9/2004 | Berreklouw |
| 6,883,522 B2 | 4/2005 | Spence et al. |
| 6,893,459 B1 | 5/2005 | Macoviak |
| 6,908,481 B2 | 6/2005 | Cribier |
| 6,949,122 B2 | 9/2005 | Adams et al. |
| 7,011,681 B2 | 3/2006 | Vesely |
| 7,018,406 B2 | 3/2006 | Seguin et al. |
| 7,044,966 B2 | 5/2006 | Svanidze et al. |
| 7,101,396 B2 | 9/2006 | Artof et al. |
| 7,147,663 B1 | 12/2006 | Berg et al. |
| 7,160,322 B2 | 1/2007 | Gabbay |
| 7,217,287 B2 | 5/2007 | Wilson et al. |
| 7,252,682 B2 | 8/2007 | Seguin |
| 7,320,704 B2 | 1/2008 | Lashinski et al. |
| 7,329,278 B2 | 2/2008 | Seguin et al. |
| 7,381,218 B2 | 6/2008 | Schreck |
| 7,381,220 B2 | 6/2008 | Macoviak et al. |
| 7,442,204 B2 | 10/2008 | Schwammenthal et al. |
| 7,503,930 B2 | 3/2009 | Sharkawy et al. |
| 7,524,330 B2 | 4/2009 | Berreklouw |
| 7,524,331 B2 | 4/2009 | Birdsall |
| 7,578,843 B2 | 8/2009 | Shu |
| 7,585,321 B2 | 9/2009 | Cribier |
| 7,597,711 B2 | 10/2009 | Drews et al. |
| 7,618,446 B2 | 11/2009 | Andersen et al. |
| 7,625,403 B2 | 12/2009 | Krivoruchko |
| 7,632,308 B2 | 12/2009 | Loulmet |
| 7,708,775 B2 | 5/2010 | Rowe et al. |
| 7,717,955 B2 | 5/2010 | Lane et al. |
| 7,727,276 B2 | 6/2010 | Machiraju |
| 7,748,389 B2 | 7/2010 | Salahieh et al. |
| 7,780,725 B2 | 8/2010 | Haug et al. |
| 7,896,915 B2 | 3/2011 | Guyenot et al. |
| 7,947,072 B2 | 5/2011 | Yang et al. |
| 7,947,075 B2 | 5/2011 | Goetz et al. |
| 7,959,672 B2 | 6/2011 | Salahieh et al. |
| 7,981,153 B2 | 7/2011 | Fogarty et al. |
| 7,988,725 B2 | 8/2011 | Gross et al. |
| 8,025,695 B2 | 9/2011 | Fogarty et al. |
| 8,048,153 B2 | 11/2011 | Salahieh et al. |
| 8,052,749 B2 | 11/2011 | Salahieh et al. |
| 8,055,360 B2 | 11/2011 | Park et al. |
| 8,057,540 B2 | 11/2011 | Letac et al. |
| 8,092,518 B2 | 1/2012 | Schreck |
| 8,092,521 B2 | 1/2012 | Figulla et al. |
| 8,123,801 B2 | 2/2012 | Milo |
| 8,133,270 B2 | 3/2012 | Kheradvar et al. |
| 8,142,492 B2 | 3/2012 | Forster et al. |
| 8,157,852 B2 | 4/2012 | Bloom et al. |
| 8,157,853 B2 | 4/2012 | Laske et al. |
| 8,163,011 B2 | 4/2012 | Rankin |
| 8,172,898 B2 | 5/2012 | Alferness et al. |
| 8,182,528 B2 | 5/2012 | Salahieh et al. |
| 8,182,530 B2 | 5/2012 | Huber |
| 8,206,437 B2 | 6/2012 | Bonhoeffer et al. |
| 8,231,670 B2 | 7/2012 | Salahieh et al. |
| 8,236,049 B2 | 8/2012 | Rowe et al. |
| 8,246,677 B2 | 8/2012 | Ryan |
| 8,252,051 B2 | 8/2012 | Chau et al. |
| 8,262,724 B2 | 9/2012 | Seguin et al. |
| 8,277,502 B2 | 10/2012 | Miller et al. |
| 8,282,051 B2 | 10/2012 | Nutaro et al. |
| 8,287,591 B2 | 10/2012 | Keidar et al. |
| 8,292,938 B2 | 10/2012 | Case |
| 8,308,796 B2 | 11/2012 | Lashinski et al. |
| 8,308,798 B2 | 11/2012 | Pintor et al. |
| 8,317,858 B2 | 11/2012 | Straubinger et al. |
| 8,323,332 B2 | 12/2012 | Agnew |
| 8,323,335 B2 | 12/2012 | Rowe et al. |
| 8,403,983 B2 | 3/2013 | Quadri et al. |
| 8,449,599 B2 | 5/2013 | Chau et al. |
| 8,579,964 B2 | 11/2013 | Lane et al. |
| 8,585,755 B2 | 11/2013 | Chau et al. |
| 8,685,085 B2 | 4/2014 | Guyenot et al. |
| 8,685,086 B2 | 4/2014 | Navia et al. |
| 2002/0151970 A1 | 10/2002 | Garrison et al. |
| 2003/0130726 A1 | 7/2003 | Thorpe et al. |
| 2007/0027533 A1 | 2/2007 | Douk |
| 2008/0004697 A1 | 1/2008 | Lichtenstein et al. |
| 2010/0049315 A1 | 2/2010 | Kirson |
| 2010/0100173 A1 | 4/2010 | Lafontaine |
| 2010/0217382 A1 | 8/2010 | Chau et al. |
| 2010/0262232 A1* | 10/2010 | Annest .......... 623/2.17 |
| 2010/0312333 A1 | 12/2010 | Navia et al. |
| 2011/0137410 A1 | 6/2011 | Hacohen |
| 2011/0224785 A1 | 9/2011 | Hacohen |
| 2011/0295363 A1 | 12/2011 | Girard et al. |
| 2011/0319988 A1 | 12/2011 | Schankereli et al. |
| 2011/0319989 A1 | 12/2011 | Lane et al. |
| 2012/0016464 A1 | 1/2012 | Seguin |
| 2012/0053675 A1 | 3/2012 | Borock |
| 2012/0059458 A1 | 3/2012 | Buchbinder et al. |
| 2012/0101571 A1* | 4/2012 | Thambar et al. .......... 623/2.17 |
| 2013/0184811 A1 | 7/2013 | Rowe et al. |
| 2013/0211508 A1 | 8/2013 | Lane et al. |
| 2013/0282110 A1 | 10/2013 | Schweich et al. |
| 2013/0282114 A1 | 10/2013 | Schweich et al. |
| 2014/0012372 A1 | 1/2014 | Chau et al. |
| 2014/0012373 A1 | 1/2014 | Chau et al. |
| 2014/0039611 A1 | 2/2014 | Lane et al. |
| 2014/0052237 A1 | 2/2014 | Lane et al. |
| 2014/0200662 A1* | 7/2014 | Eftel et al. .......... 623/2.38 |

OTHER PUBLICATIONS

U.S. Appl. No. 61/287,099, filed Dec. 4, 2009, Chau et al.
U.S. Appl. No. 61/266,774, filed Dec. 16, 2009, Chau et al.
International Search Report in Application No. PCT/US2013/036728, dated Aug. 8, 2013, 3 pages.
International Search Report in Application No. PCT/US2013/036734, dated Aug. 20, 2013, 4 pages.
International Search Report and Written Opinion in International Application No. PCT/US2014/061788, dated Jan. 28, 2015, 17 pages.

* cited by examiner

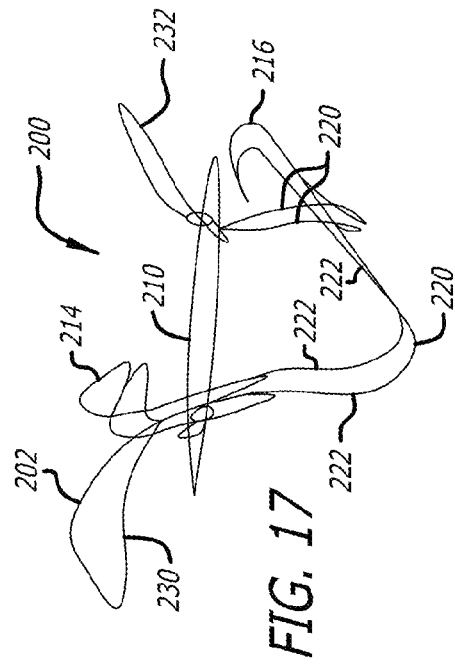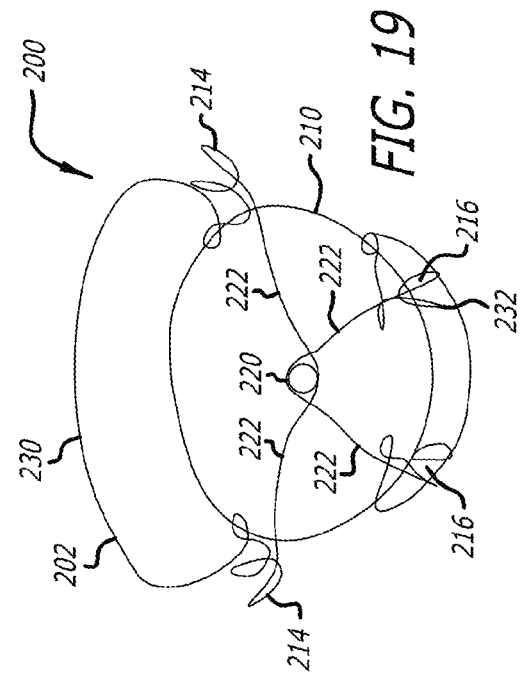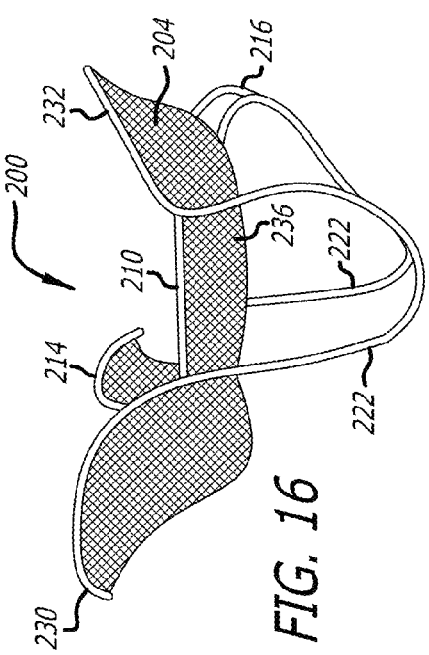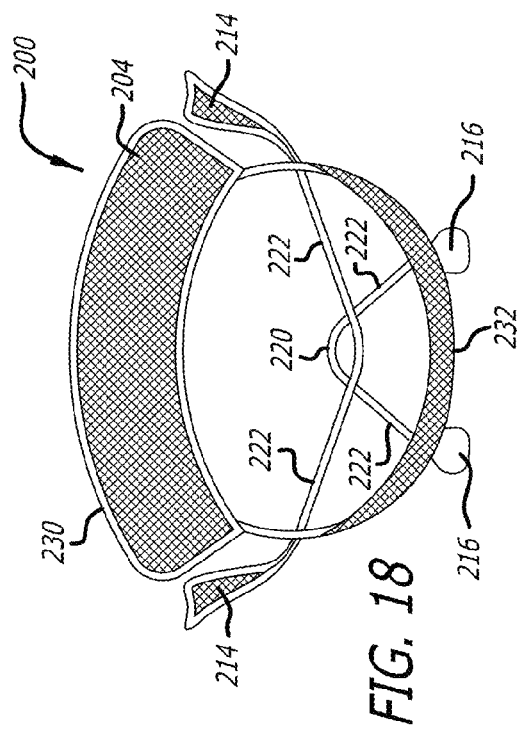

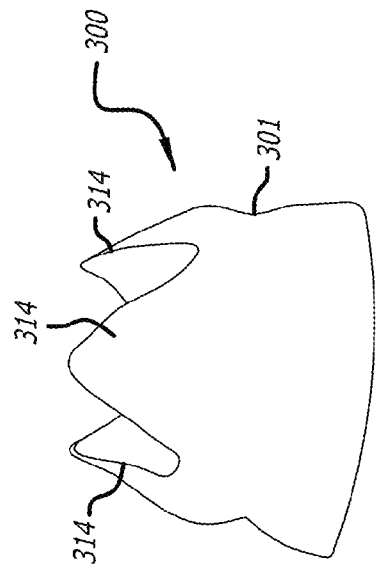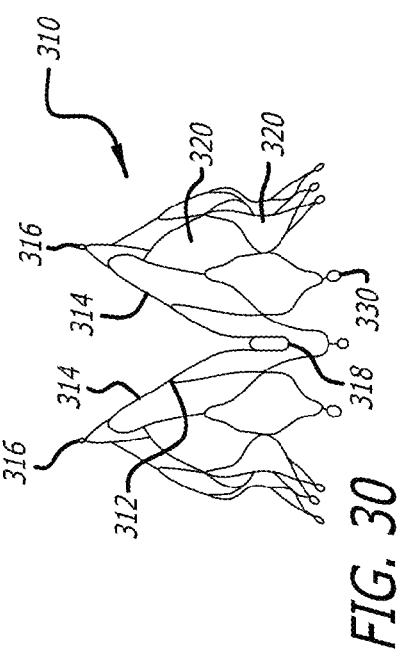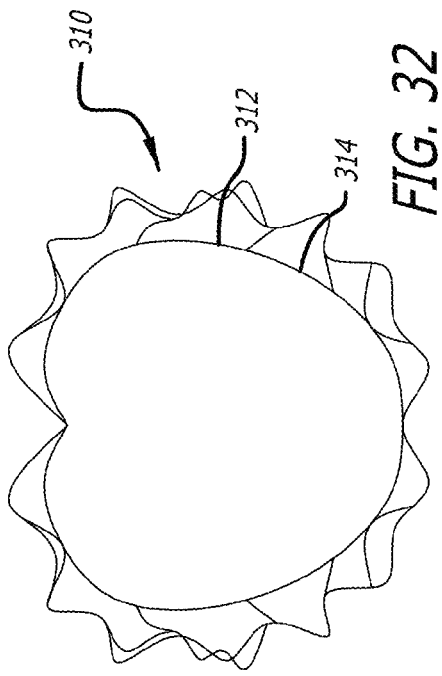

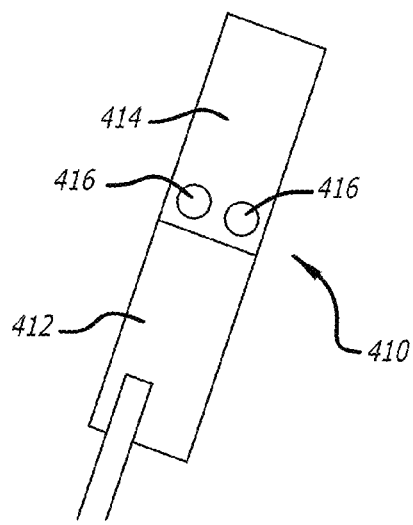 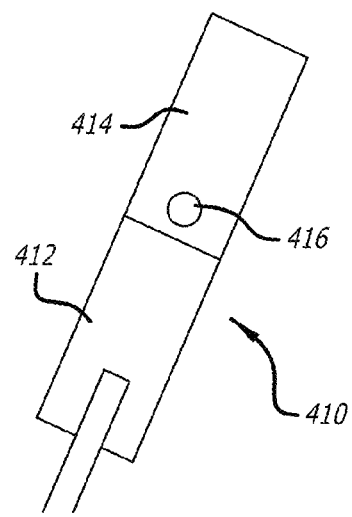
FIG. 53B          FIG. 53C
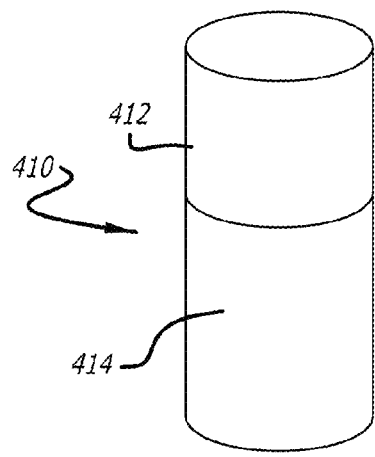 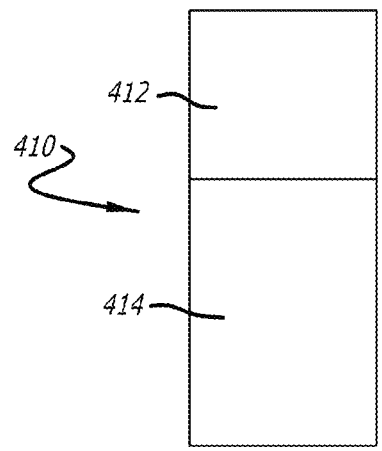
FIG. 53D          FIG. 53E

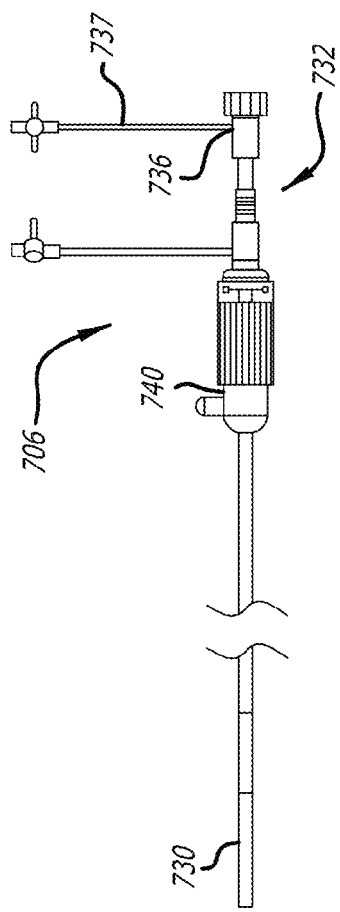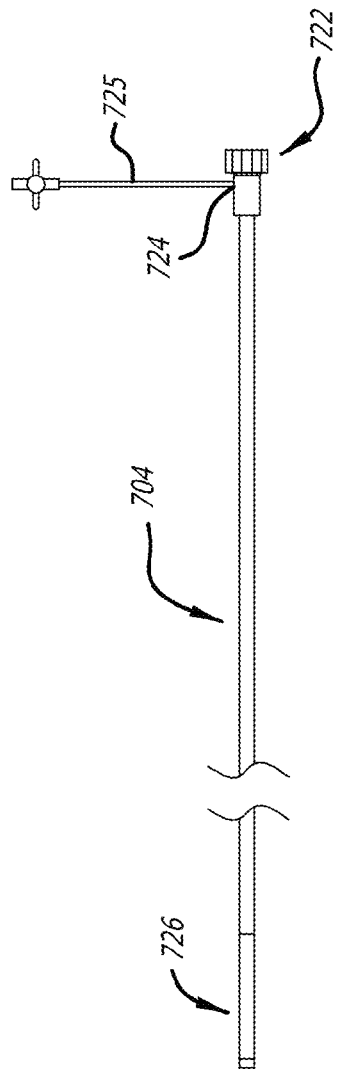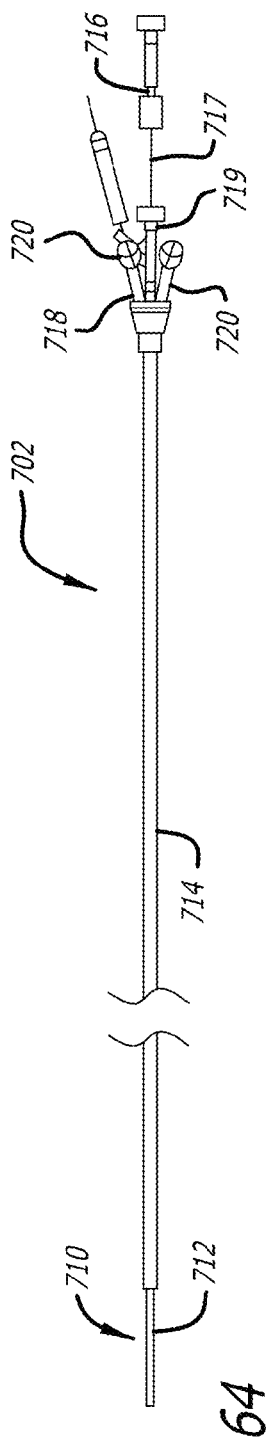

METHODS AND SYSTEMS FOR HEART VALVE THERAPY

CROSS-REFERENCES TO RELATED APPLICATIONS

This application claims the benefit of U.S. Application Ser. No. 61/894,766, filed Oct. 23, 2013, the entire disclosure of which is expressly incorporated herein.

BACKGROUND OF THE DISCLOSURE

The present disclosure relates to heart valve interventional systems and methods and more particularly, to mitral valve therapy systems and methods.

The long-term clinical effect of valve regurgitation is well recognized as a significant contributor to cardiovascular related morbidity and mortality. Thus, the primary goal of any therapy of the mitral valve is to significantly reduce or eliminate the regurgitation. By eliminating the regurgitation, the destructive volume overload effects on the left ventricle are attenuated. The volume overload of mitral regurgitation (MR) relates to the excessive kinetic energy required during isotonic contraction to generate overall stroke volume in an attempt to maintain forward stroke volume and cardiac output. It also relates to the pressure potential energy dissipation of the leaking valve during the most energy-consuming portion of the cardiac cycle, isovolumic contraction. Additionally, successful MR reduction should have the effect of reducing the elevated pressures in the left atrium and pulmonary vasculature reducing pulmonary edema (congestion) and shortness of breath symptomatology. It also has a positive effect on the filling profile of the left ventricle (LV) and the restrictive LV physiology that can result with MR. These pathophysiologic issues indicate the potential benefits of MR therapy, but also indicates the complexity of the system and the need for a therapy to focus beyond the MR level or grade.

It is also desirable to prevent new deleterious physiology or function of the valve. The procedure and system used to fix the mitral valve ideally should avoid worsening other (non-MR) existing pathologic conditions or creating new pathologic conditions as a result of the treatment. One of the critical factors to be managed is mitral stenosis or creation of an inflow gradient. That is, if a valve system is used that does not allow for sufficient LV inflow without elevated filling pressures, then critical benefits of MR reduction are dissipated or lost. Moreover, atrial fibrillation is to be avoided as it can result if elevated pressures are not relieved by the therapy, or are created by the system (high pressure results in atrial stress leading to dilatation ultimately leading to arrhythmias). Also, if the procedure results in damage to atrial tissue at surgery, it can result in the negative physiologic effect of atrial fibrillation. Further, one should be aware of the possibility of increased LV wall stress through an increase in LV size (LV geometry). Due to the integral relationship of the mitral valve with LV geometry through the papillary and chordal apparatus, LV wall stress levels can be directly affected resulting in alterations of LV filling and contraction mechanics. Accordingly, a system that does not preserve or worsens the geometry of the LV can counter the benefits of MR reduction because of the alteration of contractile physiology.

It has been generally agreed that it is preferable if the native valve can be repaired (e.g. with an annular ring), versus an open surgical valve replacement. Repair of valve elements that target the regurgitant jet only results in minimal alteration to the valve elements/structures that are properly functioning allowing for the least potential for negatively affecting the overall physiology while achieving the primary goal. Native valve preservation can be beneficial because a well repaired valve is considered to have a better chance of having long standing durability versus a replacement with an artificial valve that has durability limits. Also, while current surgical artificial valves attempt chord sparing procedures, the LV geometric relationship may be negatively altered if not performed or performed poorly leading to an increase in LV wall stress due to an increase in LV diameter. Thus, while repair is preferred and possible for technically competent surgeons, the relatively high recurrence rate of MR due to inadequate repair, the invasiveness of the surgery especially in sick or functional MR patients, and the complexities of a repair for many surgeons lead to a high percentage of mitral operations being replacement.

Conventionally, surgical repair or replacement of the mitral valve is performed on cardiopulmonary bypass and is usually performed via an open median sternotomy resulting in one of the most invasive high risk cardiac surgical operations performed, especially in subpopulations such as functional MR. Therefore, a key improvement to mitral valve operations is to significantly lower the risk and invasiveness, specifically utilizing a percutaneous or minimally invasive technique.

While there have been attempts to replicate existing surgical repair via less invasive surgical or percutaneous methods, given the complexity of repairing the valve surgically, the efforts have largely been deemed lacking in achieving adequate efficacy and have not altered the risk benefit ratio sufficiently to warrant ongoing investment, approval, or adoption. In particular, there has been a general technology failure due to the complexity of anatomy to percutaneously manage with an implant or implantable procedure. The broad spectrum of mitral disease directly influences outcomes with a resulting inability to match technology with pathology. There has also been observed inadequate efficacy with poor surgical replication and safety results. It has also been recognized that percutaneous approaches have been successful to certain valve procedures, such as aortic valve replacement associated with a single pathology and a relatively circular rigid substrate, mitral valves often suffer from multiple pathologies and a have flexible or elastic annulus with multiple structures, making this a more challenging goal.

Further challenges exist in positioning and orienting mitral regurgitation therapy structures at the interventional site. Cooperation and sealing between component parts has also been a consideration in effective mitral regurgitation therapy. Additionally, more can be done to both identify and take advantage of native anatomical features common to the mitral valve. More can also be done to streamline the implantation process.

Accordingly, what is needed is an effective long lasting MR reduction without creating negative physiologic consequences to the cardio-pulmonary system (heart, lungs, peripheral vasculature) including stenosis, LV wall stress and atrial fibrillation. It is also desirable to be able to perform the operation in a reliable, repeatable, and easy to perform procedure and to have a broadly applicable procedure for both patients and physicians, while employing a significantly less invasive method. Moreover, it is desirable to take advantage of anatomical features leading themselves to an effective mitral regurgitation therapy, and to provide component structures which cooperate to address regurgitation as well as implantation aids facilitating proper orientation and placement.

The present disclosure addresses these and other needs.

SUMMARY

Briefly and in general terms, the present disclosure is directed towards replacement systems and methods. In one particular aspect, the present disclosure describes a percutaneous or minimally invasive mitral valve replacement system that eliminates MR, provides adequate physiologic inflow, and preserves and/or improves LV geometry in a reliable, repeatable, and easy to perform procedure.

In one aspect, there is provided a mitral valve replacement system including an anchoring structure and an artificial valve configured to treat a native heart. In another aspect, there is provided a method of replacing a valve including providing anchor structure, advancing a valve delivery catheter into a heart, advancing an artificial valve out of the delivery catheter and into the heart, and positioning the artificial valve to treat a native heart.

An anchor assembly configured with feet or projections sized and shaped to engage an anatomical gutter located in the left ventricle proximate the mitral valve annulus acts as support for subsequent implantation of a replacement valve assembly. An orientation and location tool can be employed to facilitate proper positioning of the anchor assembly and replacement valve assembly at the mitral valve interventional site. In this regard, remote visualization techniques can be set in response to markers provided on the orientation tool and subsequently employed during an implantation procedure. An anchor placement tool or sub-structure is further provided to gain access to the mitral valve in a minimally invasive manner. Delivery systems for the anchor and valve assemblies likewise accomplish non-traumatic implantation. The anchor assembly includes structure for placement at or proximate a mitral valve annulus, as well as structure for sealing within anatomy and engagement with a waist portion of the mitral valve assembly. The implanted mitral valve presents a tri-leaflet structure for controlling blood flow, as well as structure for accomplishing a seal within the anchor.

In certain approaches, forces can be translated to various anatomical features of and proximate the mitral valve. In one approach, an anchor assembly can be implanted within the anatomical gutter leaving the leaflets of the mitral valve unaffected. In other approaches, structure of the anchor can cross the annulus of the mitral valve and can further partially or completely retain leaflets. Thus, forces generated by the heart and inherent in blood flow can be translated by an anchor directly and solely to the anatomical gutter, or such forces can be in part translated to leaflet, chordae and papillary muscle anatomy to varying degrees.

In one approach, the mitral valve replacement system addresses a number of basic functional requirements. One requirement is the valve function itself, the occlusion of flow during systole, and open to flow during diastole. Another requirement is the seal between the artificial replacement valve frame/structure and the tissue to prevent/minimize any paravalvular leaks or flow. A further requirement is the anchoring or securement function to hold the functioning valve in position and withstand the substantial and variable cyclical load placed on the valve during systolic pressurization of the valve surface. It is intended that each of these is met in the durable, therapeutically, and physiologically appropriate mitral valve replacement system disclosed herein.

The presently disclosed system may utilize a staged approach to the functional elements of the system, starting with the anchoring or securement functional element. Additionally, the staging can be performed within a single procedure or in multiple, time separated procedures, e.g. on different days. By staging and separating functional elements, the individual elements will be simpler in design and simpler to deploy and implant. This staging of the anchor implantation of the present invention provides a stable, reliable, consistent, substrate to deliver a replacement valve into the mitral position.

A mitral valve treatment system according to the present disclosure includes one or more of an anchor element, a sealing element, and a valve element, and can utilize an anchor delivery system, and a valve delivery system. More than one element may be incorporated into a structure, for example, an anchor element also may include a sealing structure, or a valve element may include a sealing structure. In accordance with the present teachings, the elements of the valve replacement system may be implanted in staged procedures, for example, an anchor element may be implanted during a first procedure and a valve element may be implanted during a second procedure. As disclosed herein, the processes, systems used for implantation, and timing of implantation may vary. The present disclosure further contemplates that the anchor element (and in some cases sealing element) of the disclosed mitral valve replacement system may be used with existing valve technologies, as discussed further below. Similarly, delivery systems may include those disclosed herein, but the present disclosure also contemplates that existing delivery systems may be used to deliver prior art valve structures.

Moreover, the valve anchor approach can fundamentally alter the complexity of performing a completely percutaneous mitral replacement by creating a reliable and consistent substrate. Thus, it is intended that the implant design exploit the geometry/mechanics of the commissures to create sufficient holding capability. In one particular aspect, as stated, the anatomical gutter found below a valve annulus is the site for anchoring. Further, design and delivery approaches that maintain native valve function providing the ability to completely separate and stage the implantation of the system functional components is contemplated as are delivery methods that have potential for quick fluoroscopic delivery, positioning, and deployment. Consequently, there is an optimal valve performance opportunity due to maximal design flexibility and technology leveraging, and a delivery capability to achieve precise positioning prior to valve deployment. The same creates desired tissue/implant sealing and maintains sub-valvular structural relationships.

Accordingly, employing the present system and method facilitates effective long lasting MR reduction without creating negative physiologic consequences to the cardio-pulmonary system (heart, lungs, peripheral vasculature) including stenosis, LV wall stress, and atrial fibrillation. The method can involve performance of the operation in a reliable, repeatable, and easy to perform procedure and is a broadly applicable procedure for both patients and physicians. A significantly less invasive method results, one which can be fully percutaneous from the start.

Other features and advantages of the present disclosure will become apparent from the following detailed description, taken in conjunction with the accompanying drawings, which illustrate, by way of example, the principles of the invention.

BRIEF DESCRIPTION OF THE DRAWINGS

FIG. 16 is a side view, depicting one embodiment of a wire frame anchor structure;

FIG. 17 is a side view of the structure of FIG. 16 with Dacron covering removed;

FIG. 18 is a top view, depicting the wire frame of FIG. 16;

FIG. 19 is a top view, depicting the wire frame of FIG. 18 with a Dacron cover removed;

FIG. 30 is a side view, depicting a valve frame;

FIG. 31 is a side view, depicting the valve frame of FIG. 30 with a covering;

FIG. 32 is a top view, depicting the valve frame of FIG. 30;

FIG. 53B is an enlarged view, depicting markers;

FIG. 53C is an enlarged view, depicting rotationally aligned markers;

FIG. 53D is a perspective view, depicting a cylindrical shaft which is not aligned with an imaging plane;

FIG. 53E is a side view, depicting a cylindrical shaft which is in plane or parallel with an imaging plane;

FIG. 62 is a side view, depicting an outer sheath of the delivery system depicted in FIG. 61;

FIG. 63 is a side view, depicting a delivery sheath of the delivery system of FIG. 61;

FIG. 64 is a side view, depicting an inner assembly of the delivery system of FIG. 61;

DETAILED DESCRIPTION OF THE PREFERRED EMBODIMENTS

Figure 1:
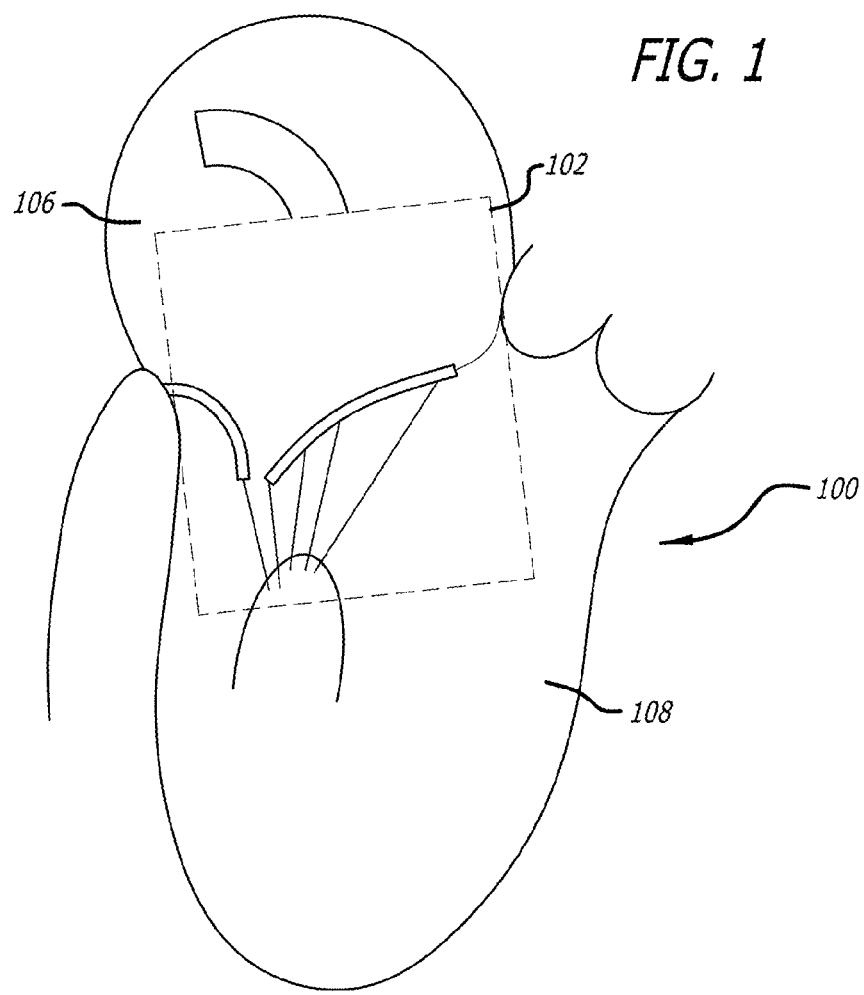
FIG. 1 is a cross-sectional view, depicting a native heart indicating an operating window region.

Referring now to the drawings, which are provided by way of background and example, and not limitation, the present disclosure relates to medical interventional procedures and devices. In various aspects, heart valve therapy is addressed and in particular, mitral valve replacement approaches are presented.

Overall, the present disclosure describes a system including a platform anchor, valve, and delivery technology that allows therapeutic flexibility (mitral replacement with either tissue or mechanical valves), implantation flexibility via either fully percutaneous or minimally invasive (trans-apical, trans-atrial) procedures, minimized delivery complexity to allow a simple to perform procedure, and a patient population that is not restricted by the underlying pathology.

A mitral valve replacement system according to the present disclosure includes one or more of an anchor element, sealing structure, and a valve element, and utilizes orientation tools as well as an anchor delivery system, and a valve delivery system. An anatomical gutter proximate the mitral valve is intended to be a target for anchoring at least portions of the replacement system. Generally, the gutter is a three dimensional composite LV sided anatomic structure that extends in a u-shape from one trigone region to the other bounded by the mitral leaflets on one side, annulus in the base region of the gutter, and the LV wall on the other side. Functionally, it collects and diverts sub-annular/leaflet blood during systole into the aortic outflow tract.

More than one element may be incorporated into a structure, for example, an anchor element also may include a sealing structure, or a valve element may include a sealing structure. In accordance with the present teachings, the elements of the valve replacement system may be implanted in staged procedures, for example, an anchor element may be implanted during a first procedure and a valve element may be implanted during a second procedure. As disclosed herein, the processes, systems used for implantation, and timing of implantation may vary. The present disclosure further contemplates that the anchor element (and in some cases sealing element) of the disclosed mitral valve replacement system may be used with existing valve structures, as discussed further below. Similarly, delivery systems may include those disclosed herein, but the present disclosure also contemplates that existing delivery systems may be used to deliver prior art valve structures.

It should be noted that in planned percutaneous structural heart interventions (TAVI, mitral repair, mitral replacement) (i.e. percutaneous), there are typically at least two procedures performed for each individual patient. The first procedure includes a diagnostic assessment and possible PCI/stenting of the patient's coronary arteries and often includes a right heart cath for cardiac physiology assessment. Valve implantation and or repair are not performed prior to knowing the patient has been previously completely revascularized if necessary.

Generally the most difficult and most significant requirement for a less invasive valve system is the anchoring attachment of the system. The presently disclosed mitral valve replacement system staging of the anchor implantation allows exploitation of various anatomic valve and ventricular structures to achieve the required holding force of the anchor system. When performed in two time separated procedures, staging the implantation of the anchor separately from other system elements provides time for tissue ingrowth into the anchor structure and resultant strengthening of the overall holding force of the anchor structure in the anatomy.

Staging of anchor implantation allows for maintaining native valve function until artificial valve element(s) are in place. Staging also helps in mitral valve replacement where there is limited operating space. It is to be recognized that immediate valve placement after anchor implanting is contemplated.

With reference to FIG. 1, there is shown a schematic cross-section of a heart 100. A box 102 is provided to indicate an operating window for mitral valve replacement. As can be gleaned from the schematic representation, the operating space for mitral valve replacement is limited by the size of the left atrium 106. Whereas the left ventricle 108 defines a larger space, when a repair procedure employs a left atrium approach, the cavity defined by the size of the left atrium 106 must be taken into consideration. Moreover, replacement structure and delivery systems must be sized and configured to be passed within and through, as well as function within the left atrium 106. In fact, the distance from a mitral valve annulus to a roof of the left atrium 106 is up to or approximately 4.5 cm. A delivery approach that delivers individual components separately (whether staged in separate procedures or not) can thus be advantageous since smaller sub-component parts can be introduced at the interventional site and later assembled. To wit, a fully assembled replacement device could be much more difficult to advance to the interventional site and be oriented properly to effect a replacement.

It is contemplated that anchor element embodiments utilize and exploit anatomic structures and geometry to attain the required mechanical holding forces whether engaged acutely or chronically with the addition of tissue ingrowth of the anchor. Another aspect is consideration of the anchor implant is the load distribution or force per unit of area of anchor attachment. This can be at a level that does not allow the anchor structure(s) to pull out of the tissue once attached. To maximize acute mechanical hold in the tissue, the profile geometry of the anchor tissue element can be designed to maximize the breadth and depth of tissue engagement as well as the surface width and geometry of the penetrating element. The tissue used to provide the holding force for the anchor can be exploited such that certain regions of the mitral valve have greater intrinsic tensile strength (e.g. anatomical gutter or trigone region) or utilize tissue that has a response that enhances the extent (thickness, area) of ingrowth (e.g. LV muscle wall). The tissue collagen orientation in certain regions needs to be accounted for if it is small chain, non-oriented fibers or can be used to maximize hold if it is larger chain and oriented collagen.

Due to the continuous and cyclical loads and motion of the system, anchor device biostability can be required, specifically fatigue resistance, corrosion resistance and overall mechanical durability. One of the system elements is intended to interface with tissue to form a seal. This can be the anchor forming the seal and the valve seals to the anchor, or the anchor holds valve and a valve element seals to the tissue. The implanted valve interface to anchor can provide sufficient and stable holding capability with a transfer of the valve load effectively onto the anchor. This may be accomplished by a frictional fit via expansion of the valve into the anchor and/or tissue or a mechanical interlock mechanism between the anchor and valve. Further, the anchor implant structure can be a biocompatible device, including specific biocompatibility for blood contact and tissue contact.

The specific anatomic locations that may provide mechanical and structural attachment of the anchor is another area of consideration. The anchor may be designed to incorporate one or more of a commissural location such as the anterior trigone region or the posterior leaflet cleft. An attachment location could also be the anterior portion of an atrial wall, or at an annular region/surface (posterior or anterior). Leaflet capture is also contemplated such as at the sub-posterior leaflet or the sub commissural leaflet. Attachment can also be at or within the left ventricle (endocardial) such as to the posterior wall (including posterior leaflet capture or a papillary space wedge), the apical/sub-papillary, the anterior/posterior wall bridge, or transmurally (septal, free wall, apex).

Figure 2:
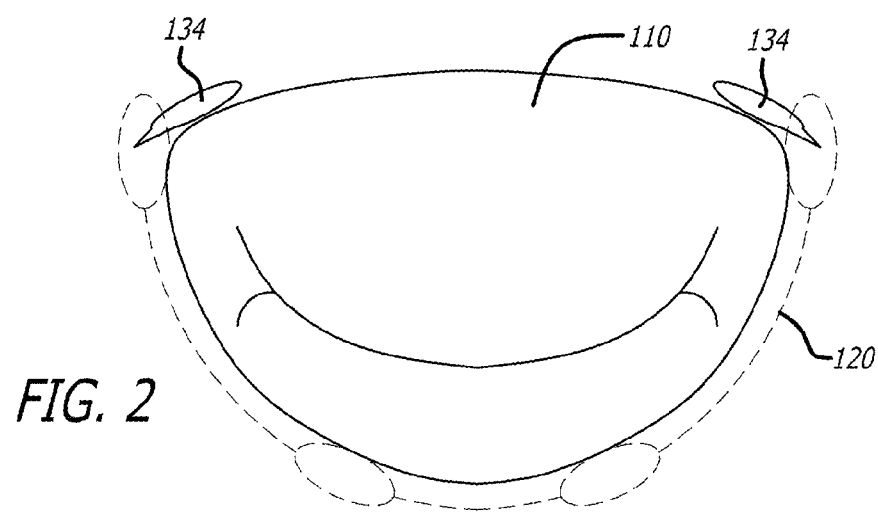
FIG. 2 is a top view, depicting a gutter perimeter of a valve including identified anchor locations.
Figures 3, 4:
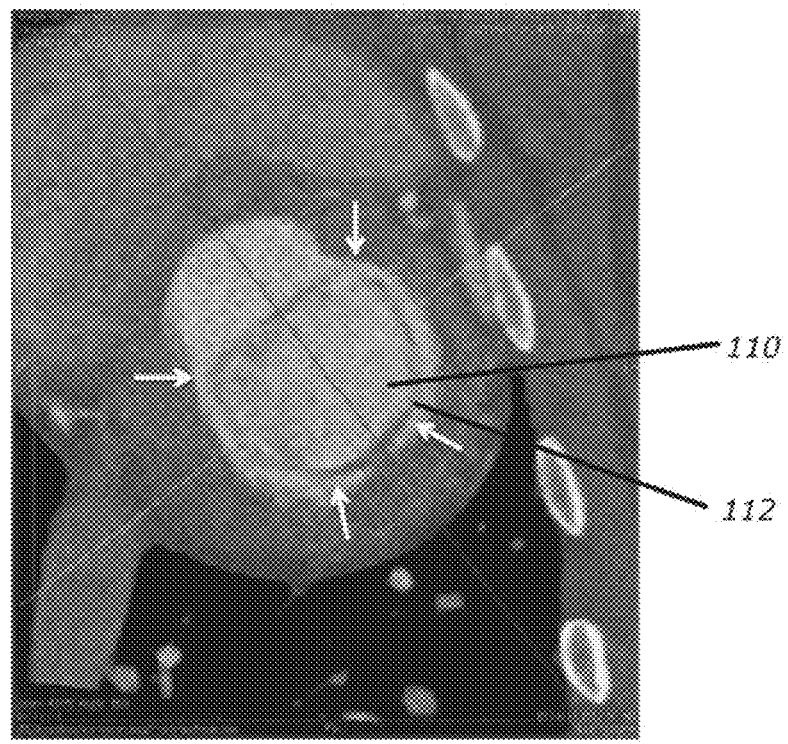
FIG. 3 is a CT sectional view of gutter anatomy, depicting leaflets and left ventricle wall with anchor locations identified.
FIG. 4 is a sub-valvular view, depicting an anatomical gutter perimeter with anchor locations identified.

With reference to FIGS. 2-4, anatomical anchoring interface structure is presented. FIGS. 2-4 depict various views of a mitral valve 110. FIG. 2 depicts a top view of a closed mitral valve 110, the dashed line representing the anatomical location of a gutter 120 which provides stable and reliable anatomy for anchoring a mitral replacement device. The dashed ovals represent intended locations for anchor structure engagement. The arrows included in FIG. 3 point to the left ventricle wall in a schematic representation of a CT scan cross-sectional view to provide a sense of the anatomy defining the gutter 120 between the left ventricle wall and a leaflet edge 112. FIG. 4 provides a sub-valvular view of the mitral valve 110 to provide further details of relevant anatomy. A dashed line again depicts the location of the gutter 120, the arrows pointing to anchor structure engagement location. It is to be recognized that the complex anatomy of the native chordae 130 and papillary muscles 132 present challenges for anchor engagement. However, there is a consistent and predictable anatomical structure pattern which exists across patient populations. Thus, anchor engagement locations within the gutter 120 are chosen to avoid chordae 130 such that anchor feet or projection are configured to be placed within defined spaces between chordae and hook into engagement with the gutter 120 for sub-leaflet attachment. The gutter 120 advantageously presents muscle tissue having good ingrowth characteristics lending to enhancing anchor function. The gutter 120 also presents a space removed from leaflet function so there is little to no impact on native heart valve operation subsequent to the anchor placements. The fibrous trigone 134 (See FIG. 2) additionally provides a high collagen, structure element for acute anchoring.

Figure 5:
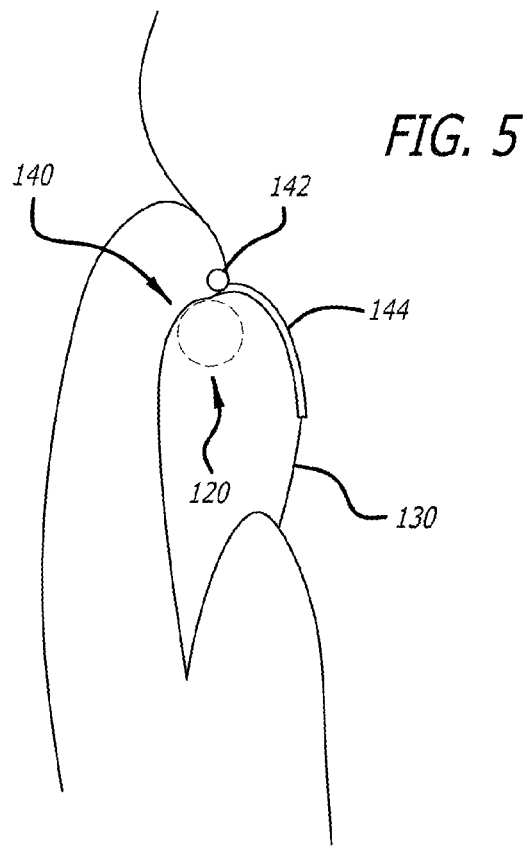
FIG. 5 is a side cross-sectional view, depicting tissue interfaces and an anatomical gutter with a leaflet closed.
Figure 6:
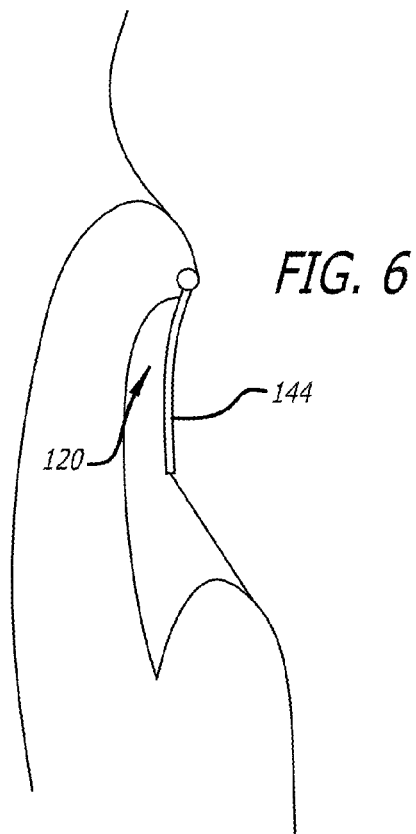
FIG. 6 is a side cross-sectional view, depicting tissue interfaces and anatomical gutter with a leaflet open.
Figure 8:
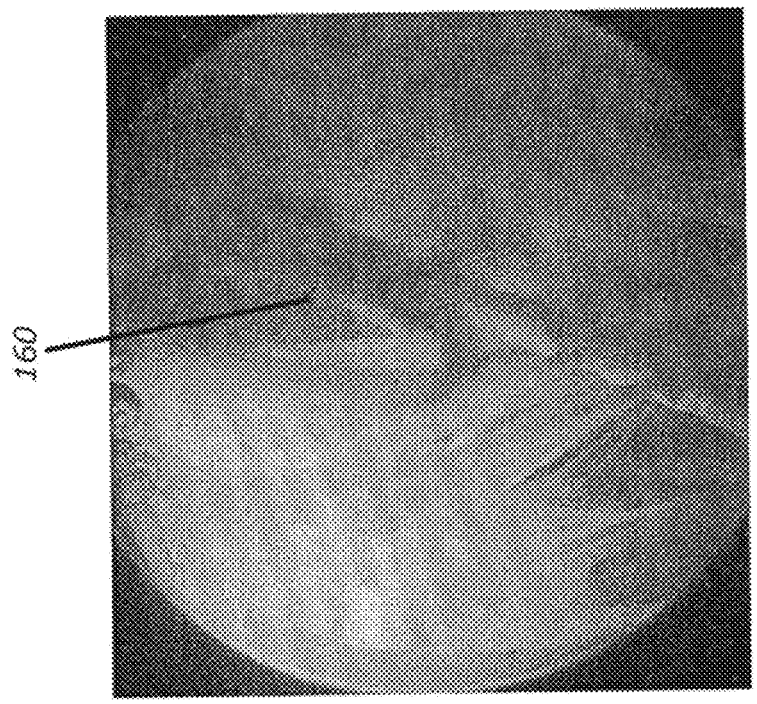
FIG. 8 is a rotated view, depicting an anchor foot passing through anatomy.
Figure 7:
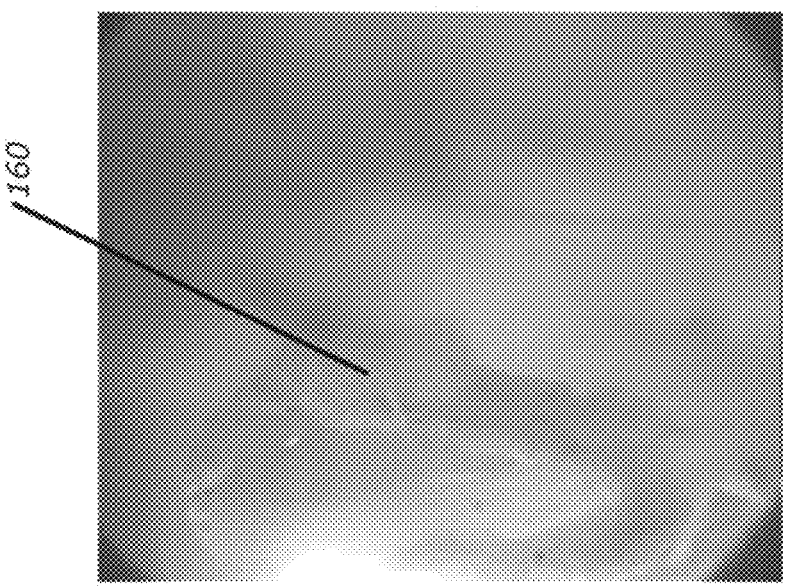
FIG. 7 is a lateral view, depicting a leaflet, subanular area behind the leaflet and a chordal web.
Figure 10:
FIG. 10 is a perspective view, depicting loop structure passing through a coaptive margin.
Figure 9:
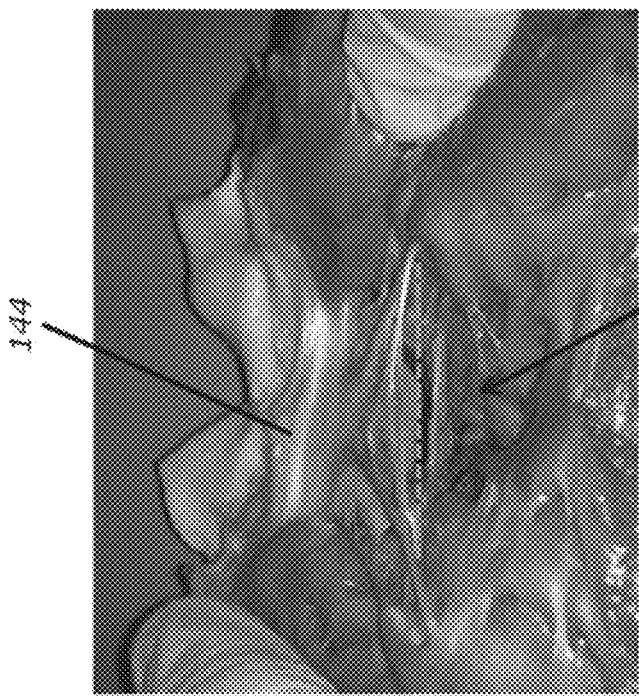
FIG. 9 is a perspective view, depicting a chordal tent with planar separation.
Figure 11:
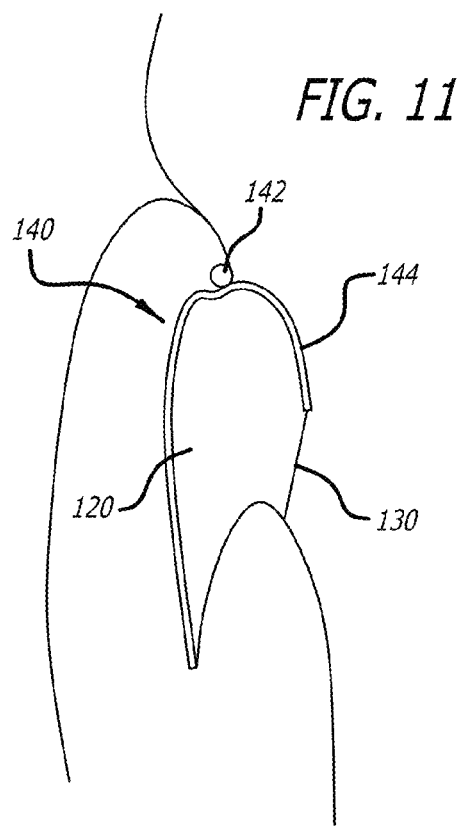
FIG. 11 is a side cross-sectional view, depicting tissue interfaces.
Figure 12:
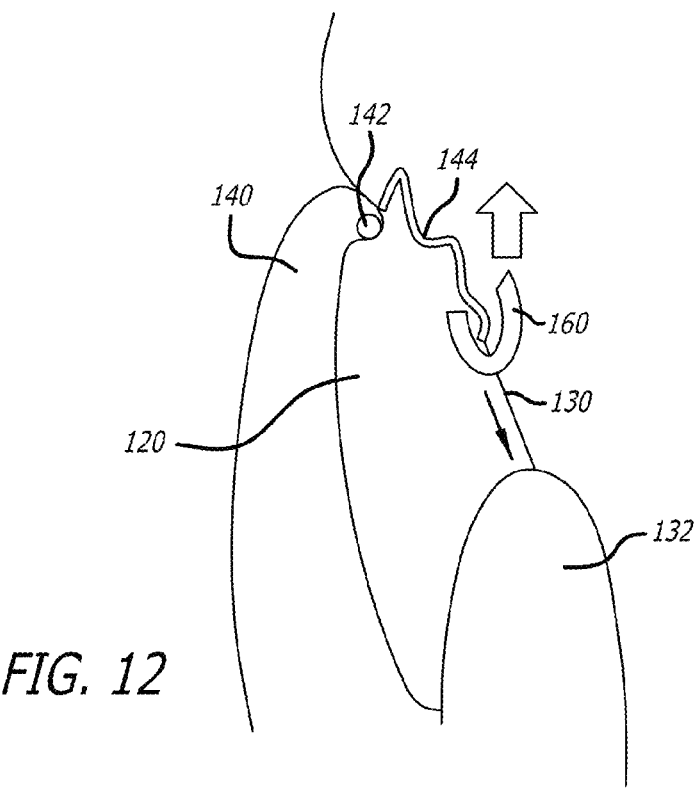
FIG. 12 is a side cross-sectional view, depicting leaflet tip loading.
Figure 13:
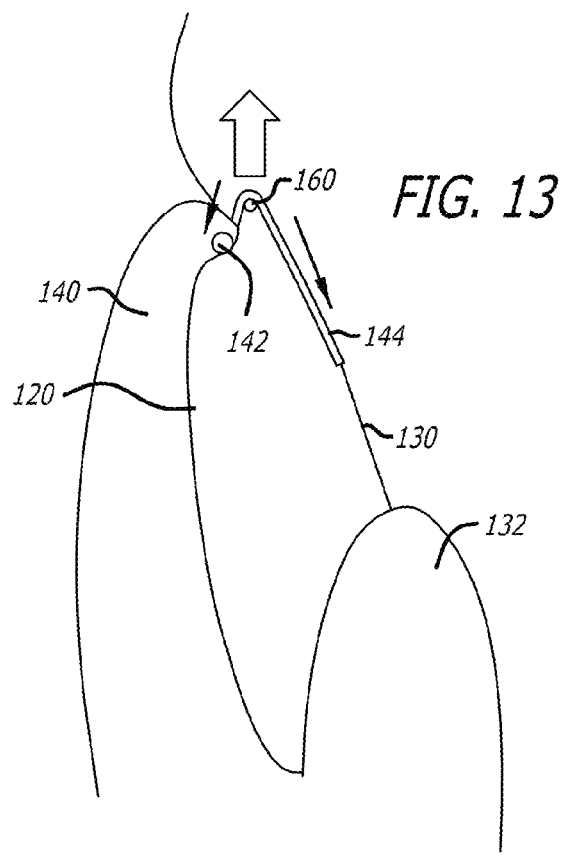
FIG. 13 is a side cross-sectional view, depicting alternative leaflet body loading.
Figure 14:
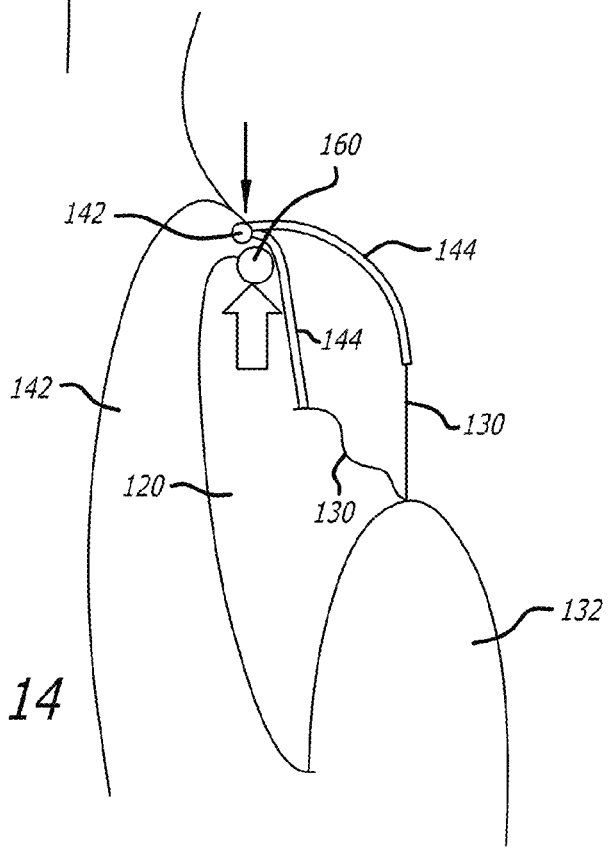
FIG. 14 is a side cross-sectional view, depicting annulus loading.

Further details concerning the gutter 120 can be understood from FIGS. 5 and 6, which depict a schematic cross-section of a left ventricle wall 140, a fibrous annulus 142 and posterior leaflet 144 of a heart. The gutter 120 exists both when the leaflet is open and closed and defines sufficient space to receive structure of an anchor device. FIGS. 7 and 8 provide further views of gutter space 120, indicating points where anchor structure 160 passes sub-valvular structure, and into the gutter. FIG. 9 additionally depicts a sub-valvular pocket 152 residing below the posterior leaflet (shown in a partially dissected heart), the same providing a convenient and effective space for receiving anchor structure. FIG. 10 depicts a V-shaped tent of chordae 154 connected to leaflets which again shows the space available for passing anchor structure into engagement with the gutter. Thus, a well-defined and distinct plane exists between chordae and the left ventricle wall which lends itself for the passage of loop or other structure without entanglement or loss of function.

Turning now to FIGS. 11-15B, various approaches to anchor loading points are discussed. With the valve leaflet 144 closed (FIG. 11), there is again a well-defined gutter 120 presented for anchoring structures. As shown above in connection with FIGS. 9 and 10, anchor structure can be passed between well-defined spaces among chordae 130. Should anchoring structure 160 be applied directly to a leaflet tip 144 (FIG. 12), load is distributed onto the chordae 130 and down to the papillary muscles 132. With such an arrangement, the leaflet 144 can become lax and thus affect heart function. Where anchor structure 160 is placed beneath the leaflet 144 (FIG. 13), load is roughly distributed evenly (represented by location of up arrow) between the annulus 142 and through the leaflet 144 to the chordae 130 and into the papillary muscle 132. Loads are thus distributed to natural load bearing structure but loading vectors (down arrows) still have different values.

In yet another approach (FIG. 14), load (represented by up arrow) can be applied by anchoring structure 160 directly to the annulus 142 by taking advantage of sub-annular anatomical geometry. Here, the leaflet 144 can help ensure that the anchor structure 160 is maintained in position below the annulus 142, both in a closed position (chordae 130 shown taut) and an open position (chordae 130 shown lax). In this way, the valve leaflet 144 remains competent until valve replacement structure is implanted as forces are applied to the annulus 142 but not the leaflet 144 or chordae 130.

Figure 15A:
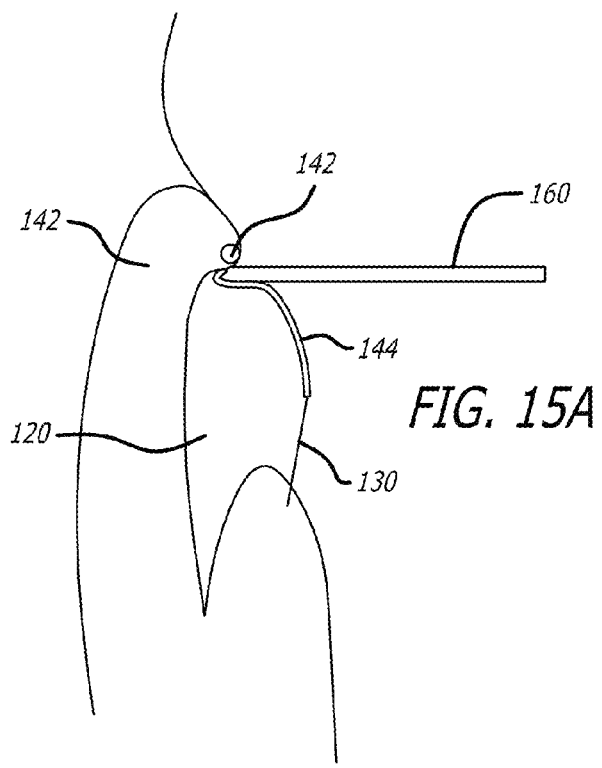
FIG. 15A is a side cross-sectional view, depicting anchor structure and a closed leaflet.
Figure 15B:
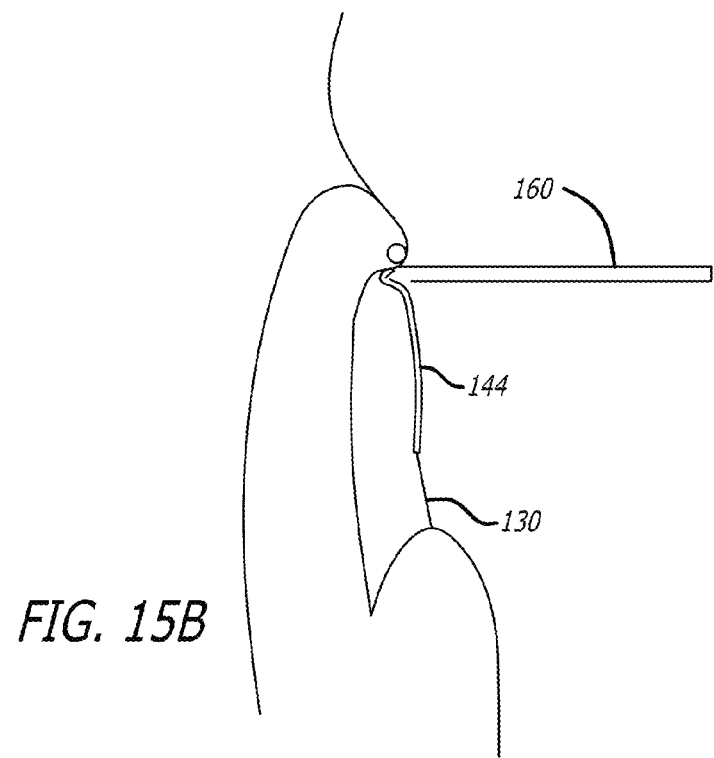
FIG. 15B is a side cross-sectional view, depicting anchor structure with a leaflet open.

As shown in FIGS. 15A-B, a supra-valvular leaflet anchoring approach is also contemplated. Anchor structure 160 is placed into engagement with the annulus 142 from above the leaflet 144. Here also, loading is directed to the annulus 142 but not to the leaflet 144 or chordae 130.

It is to be recognized that the mitral annulus is typically nonplanar, non-circular in shape, flexible and distensible. These all contribute to a complex substrate to effectively attach an artificial valve, and specifically the anchor structure. The anchor itself can thus include various approaches to support the skeletal structure. In one approach, the structure can be a supra-valvular structure with commissural feet. The commissural feet/projections can be structures which are multi-functional elements that can provide mechanical/geometric anchoring, penetration (needle/barb like) securement, and tissue based incorporation (in-growth) including subvalvular/sub-leaflet structures that extend into the LV wall, all of which do not interrupt leaflet, chordae or native valve function. Also, they can provide a positioning basis for the entire anchor because of their engagement with the commissural clefts in the anterior and posterior leaflets while still avoiding interaction or disruption of the chordae or native leaflets.

A ring structure can be designed to provide a D-shaped or alternatively a relatively circular, non-distensible, non-elongating homogeneous frame substrate that the artificial valve can engage and attach to during its deployment. This structure may be continuous or interrupted, and completely around annulus or only partially around annular circumference. Moreover, portions of the anchor can be sinusoidal in plane of valve leaflets trying to create continuous attachment around entire circumference (each sinusoid comes in and out of plane) or sinusoidal perpendicular to valve bridging from point to point creating, multiple attachment points, thereby allowing for tissue ingrowth between sinusoidal points of native leaflet or annulus tissue contact/engagement. The anchor can be malleable with points of attachment between commissures, a single wire or multiple connected wire components, or be formed into a saddle configuration to approximate natural saddle geometry of valve (may be based off of 3d echo or CT to determine geometry).

There may further be a covering of the skeletal frame of the anchor. The covering of the anchor skeleton can provide opportunity for facilitating collagen tissue ingrowth into or onto the implant structure and/or covering in locations such as on top (atrial side) of leaflet or annulus, at side of leaflets or annulus, at a ventricular wall at sub-valvular level, or underneath (ventricular side) of the leaflet or commissures.

A superstructure above the valve annulus may provide options for valve attachment to the anchor or even an alternative therapy such as mitral replacement via a septal lateral cinch. Various superstructures above the annulus can include A2 P2 points of attachment, two circles to allow for double aortic valves, or use of the atrial wall behind A2 or P2.

Materials for components used in multiple combinations and configurations, may include metals, especially for the anchor skeleton or frame structures such as Nitinol because of its superelasticity and ability to be compressed into a deliverable shape/state and then deployed into a functional state, titanium due to its strength and biocompatibility, stainless steel: hardened for its strength or malleable to aid in conforming to shape, cobalt/chromium alloy for strength and known valve component implant history; or composites to provide multiple properties based on anatomic location. Tissue elements also may be incorporated on the anchor implant to aid overall function of holding or tissue engagement and sealing including pericardial (bovine, ovine, porcine) tissue or valve tissue (bovine, ovine, porcine). Further synthetic polymers can be used as biocompatible elements in implants and on the anchor due to their know tissue and blood compatibility properties. These can include Elast-Eon (a silicone and urethane copolymer), ePTFE, urethane, silicone, PEEK, polyester (PET), or UHMWP.

Geometric/mechanical holding force for anchor that exploits the geometry/configuration of anatomic structures (relative to force vector) to achieve the necessary holding force required by a deployed artificial valve or other therapeutic element is further contemplated. The force vector encountered by the anchor structure's commissural projections are substantially under shear loading verses a perpendicular load relative to the tissue. Commissural projections or foot elements that are able to deploy behind the anterior and posterior leaflets in the gutter where the leaflet meets the annulus provides for direct mechanical holding capability. The commissural projections of the anchor structure connected and bridged to each other provide an ability to create a mechanical wedge structure to resist the force and hold the valve in position. LV wall projections of the commissural feet can provide for the ability to develop deep tissue penetration elements into the muscle, wider elements to increase surface area of contact/attachment, and longer projections to increase holding capacity. Moreover, because the projections can be placed such that they are supra annular and sub-annular, a C like structure in cross section can be utilized that is either connected or clamped. With regard to tissue penetration based securement, direct mechanical holding force is contemplated for an anchor that utilizes the natural strength of the LV and leaflet tissues to hold onto anchor structure. These elements can be configured to either be inserted into the tissue and resist pull out (barb like), or they may go into and out of tissue to provide a tissue "bite" like a stitch, or both elements can be employed. The structure can be located posterior annulus or entire annular perimeter, or adjacent leaflet tissue, the trigone/anterior annulus, an endocardial LV surface or LV Muscle tissue. Further, the tissue penetration securement elements can be linear (staple or nail like), helical (rotation axis is perpendicular to tissue interface or rotation axis is parallel to tissue interface (in/out/in/out)), curved and or curled, or bent (L shaped or S shaped).

As stated, it is also contemplated to use chronic ingrowth to provide long term stable implantation of the artificial valve and proper sealing function. In addition, chronic ingrowth of implant structural elements can serve as a fundamental mechanism to achieve the necessary holding force of the anchor functional element of the system. It exploits the natural healing response to foreign bodies placed into tissue and the blood stream to develop a strong collagen based tissue connection between the implant surface structures and the native valve tissue with a possible endothelial surface. This can be achieved while still managing the response to prevent unwanted damage to anatomic structures, damage to blood elements, or creation of thromboemboli.

More areas of consideration are the surface composition elements, specifically the material choice and texture to promote tissue reaction and device incorporation with maximal force holding capability. These elements can also be incorporated onto the tissue penetration elements to further increase the holding force by incorporation deep into tissue rather than just at the surface. The anchor can have a gross surface modification (barbs, slits), a surface texture/pores to promote ingrowth and mechanical hold, a fabric material covering (Dacron velour, double velour, ePTFE), a wire brush (multiple short wire elements) or an adhesive. There can further be a single or multiple points of attachment, planar attachment or by way of a confluent surface. Moreover, the tissue/anchor interface can be rigid or flexible and can include a wire frame structure that puts a compressive force onto surface contact interface to promote increased response. Also, tissue surface modification can include an abrasive, a chemical irritant to promote inflammatory response or application of heat.

In current conventional approaches to valvular intervention, a diagnostic echocardiograph is initially performed to assess valve function followed by two percutaneous procedures. First, a diagnostic angiography is performed with or without a right heart catheterization to assess, for example, whether they might also require revascularization first, prior to valve intervention. Here, patients do not receive valve therapy without the patient being fully revascularized. Thereafter, at a different time and place, valve replacement therapy is performed involving fixation/attachment, accomplishing a tissue sealing interface, and valve deployment and then release. In contrast, the presently described approach, however, can include an assessment involving a diagnostic echocardiography followed by a unique percutaneous valve procedure sequencing. First, a diagnostic angiography (+/− right heart cath) can be performed along with anchor fixation/attachment and anchor/tissue sealing. Subsequently, either later or during the same interventional procedure, valve replacement therapy can occur involving valve deployment and release. Thus, since the anchor implant allows the native valve to remain functional, the anchor implantation procedure could be added to the end of the angio (+/− PCI), and not require a separate interventional procedure. A quick, simple, and reliable anchor deployment could permit a fully ingrown structure that significantly enhances the holding force of a subsequently implanted replacement valve. Tissue ingrowth of the entire anchor perimeter, or at key positions thereon, can in fact provide the necessary tissue seal in advance of valve deployment. Moreover, the anchor design could be simplified due to less required acute holding force. Therefore, a tissue incorporated and healed anchor provides a structure to perform several methods of annular adjustment, including plication, reduction annuloplasty, and septal-lateral cinching.

In one specific embodiment, an anchor assembly 200 can be embodied in a frame 202 including supra-annular and sub-annular structure (See FIGS. 16-19). The anchor assembly is designed to not interfere with native valve function, allowing it to be placed some time prior to a replacement valve without degradation of valve function during the period of time between the anchor implantation and the valve implantation, whether that time is on the order of minutes, or even several days or months. It is also to be noted that the frame can be formed from a single continuous wire, or created compositely from multiple wires. The diameter or width of the wire or other structure forming the frame can range from up to 0.016 inches to 0.0235 inches or more (FIGS. 16 and 18 show the anchor with a fabric covering 204 and FIGS. 17 and 19 show the frame without covering.) A generally D-shaped central ring 210 is sized and shaped to be received at, above, or below a mitral valve or other annulus. This ring can assume a diameter of about 28-36 mm when circular or a commissure to commissure dimension of up to 30 mm to 40 mm or more and an anterior to posterior dimension of up to 20 mm to 30 mm or more and can be formed from an element having a diameter or width that ranges from up to 0.010 inches to 0.018 inches or more. Also, a circular valve interface to ring dimension can range from up to 28 mm to 36 mm and a D-shaped valve interface to ring dimension can range from up to 30 mm to 40 mm (commissure to commissure) and up to 20 mm to 30 mm anterior to posterior tip. Moreover, the anchor 210 can be configured such that portions thereof reside both above and below an annulus.

Extending from the central ring 210 are a plurality of projections or feet 214, 216. Such projections are sized and shaped to engage the sub-annular, valve gutter described above. A first pair of projections 214 are sized and shaped to each extend through one of anterior and posterior commissures and engage within or adjacent the trigone structure. In one approach, the projections can be spaced approximately 30-45 mm. Also, the projections can have a height ranging from up to 8 mm to 12 mm or more, and have a gutter engaging surface area ranging from 10-24 $mm^2$. The width of the projection can range from 2.5 to 4 mm or more and have a length ranging up to 8 mm to 12 mm or more. A second pair of projections 216 are supported by or extend from downwardly directed arms 220 which are at an opposite end supported by the central ring 210. A distance between the first and second pair of projections can be about 20-33 mm. Such arms 220 are configured when implanted to extend from the central ring 210 through the boundary between the anterior and posterior leaflets. From their connection or support points with the arm 220, each individual projection of the second pair of projections 216 extends upwardly and at an acute angle. The projections 216 are sized and shaped so that when implanted they avoid interference with mitral chordae, valve leaflets, and papillary muscles. Terminal ends of the projections are further configured to be sized and shaped to be received within and engage a posterior portion of the sub-annular gutter (as shown and described above).

The sub-annular structure of the anchor frame 210 further includes a central hub 220 which can both function as structure employed as a releasable connection during device delivery, as well as a base from which sub-annular support arms 222 extend, one to each projection 214, 216.

Figure 21:
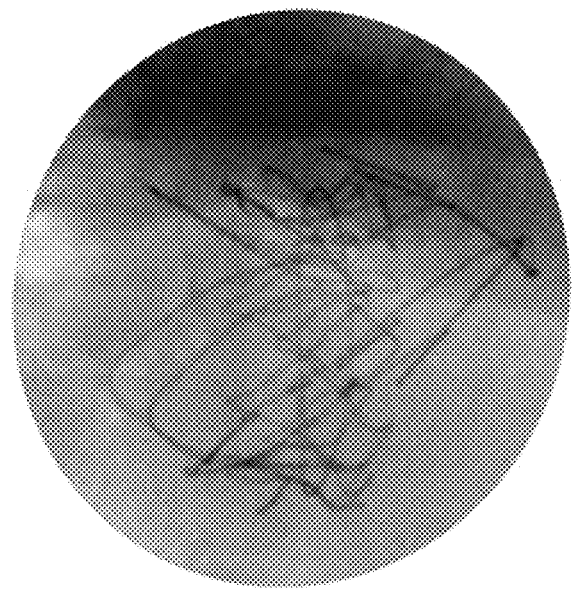
FIG. 21 is a fluoroscopic image, showing an anchor and valve implanted within anatomy.
Figure 20:
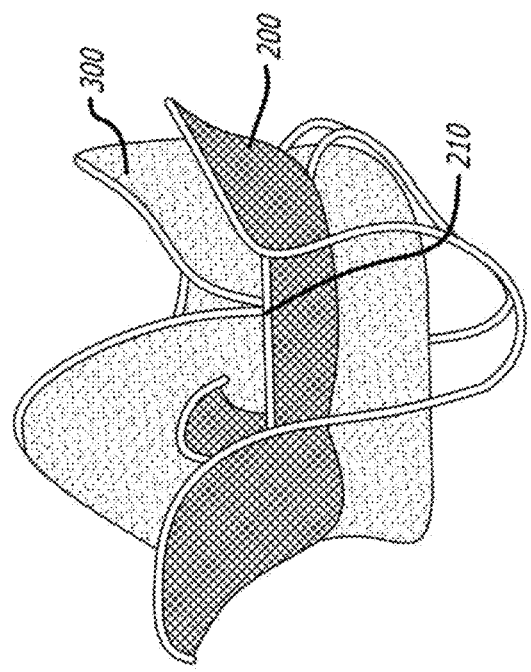
FIG. 20 is a side view of the anchor, depicting the valve assembly loaded within the anchor structure of FIG. 16.

The supra-annular structure of the wire frame 210 includes an anterior apron or visor frame 230 and a smaller posterior apron or visor frame 232. A wire forming these frames can range from up to 0.016 inches to 0.0235 inches or more, or up to 0.016 inches to 0.030 inches or more, respectively. As best seen in FIGS. 16 and 18, the apron frames accept a fabric material there across. The apron provides stability from downward forces during left ventricle filling. A skirt 236 extending below the central ring 216 is further provided for tissue ingrowth and for longer term sealing against leakage between native valve leaflets and an anchor/valve assembly. In one or more approaches, the anterior skirt height can be about 6-12 mm with a flare range of 110-180 degrees, and the posterior skirt height can be 4-10 mm with a range of about 110-180 degrees. Ventricular support structure can further range from 10-15 mm from a leaflet tip. FIG. 20 depicts one embodiment of a valve assembly 300 received by the anchor assembly 200. The valve assembly 300 can include a waist which receives the central ring 210 (See also FIG. 31). FIG. 21 shows a fluoroscopic image of the wire frame of the anchor and valve assemblies implanted within an interventional site. The anchor and valve assemblies can be configured so that the valve resides entirely or partially within the left atrium.

Figure 22:
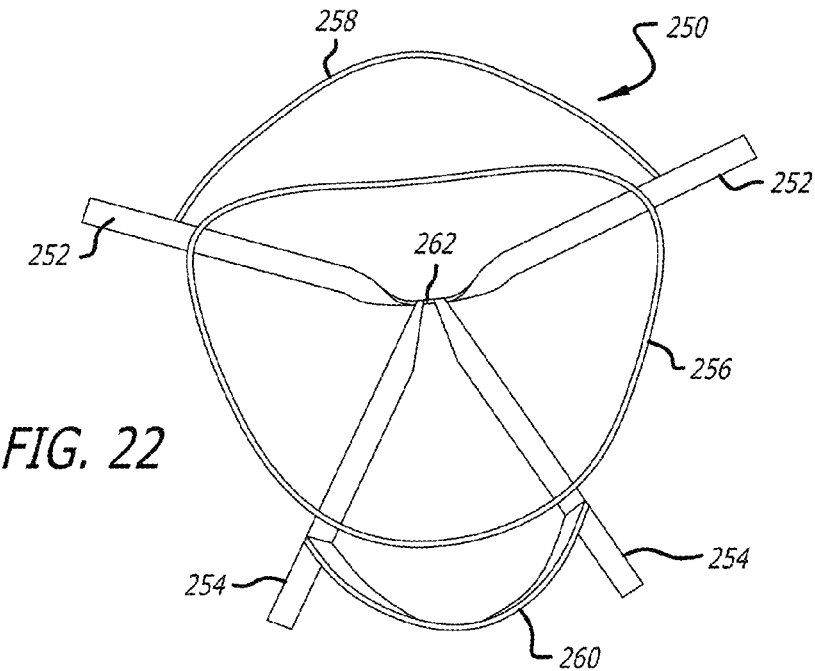
FIG. 22 is a top view, depicting a laser cut ribbon frame anchor.
Figure 23:
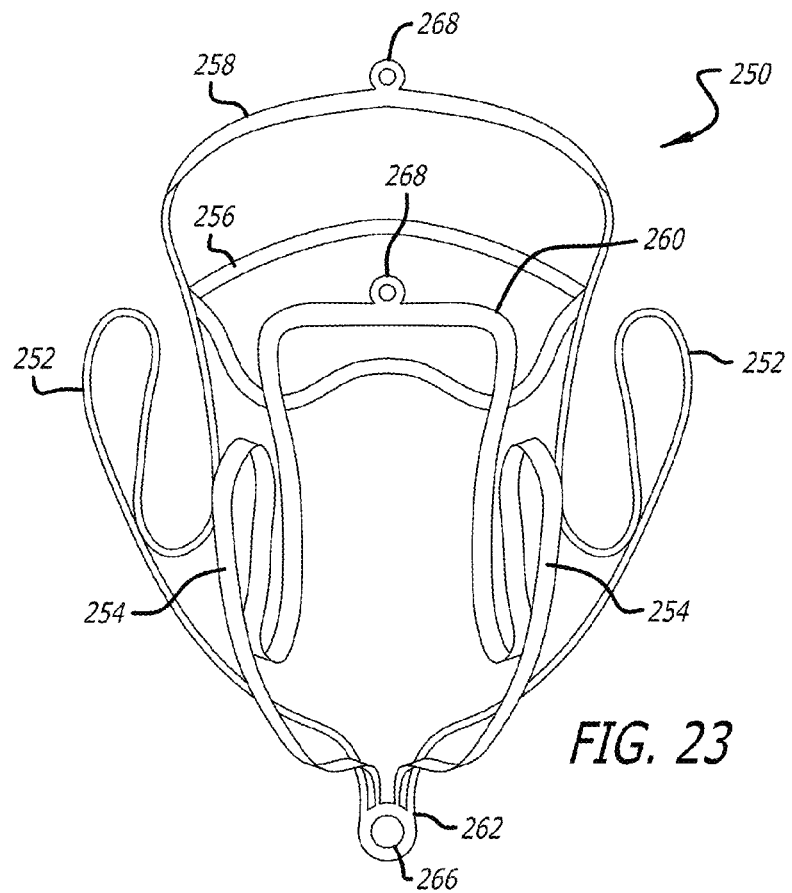
FIG. 23 is a perspective view, depicting the laser cut ribbon frame anchor of FIG. 22.

Another embodiment of an anchor assembly 250 is depicted in FIGS. 22 and 23. Rather than being formed from a continuous or segmented wire, this anchor 250 is defined by a flat or ribbon structure. Such structure can have a width of 0.035-0.050 inches and a thickness ranging from 0.008 to 0.015 inches. In one approach, the anchor can be laser cut from a tube in its final form, or cut from a tube and later formed into a desired shape. In one embodiment, the anchor 250 is configured to form projections 252, 254 for engaging a gutter formed in natural tissue, and includes a central generally D-shaped ring 256 sized and shaped to engage a valve to be positioned proximate or at a valve annulus. The members defining the ring can have a width of 0.012 to 0.020 inches and a thickness of 0.0115 to 0.015 inches. The device further includes anterior and posterior frames 258, 260 defining aprons or visors configured to stabilize the anchor within the interventional site as detailed above. The numbers defining the visor can have a width of 0.012-0.020 inches and a thickness of 0.0115 to 0.015 inches. Extending downwardly from each projection 252, 254 individually and toward a hub 262 is a support arm 264. An eyelet 266 formed at the hub 262, and the eyelets 268 formed on the apron frames 258, 260 define structure that can be employed to facilitate delivery of the anchor 250 at an interventional site. Ventricular support structure can have a width ranging from 0.042-0.060 inches and a thickness of about 0.015-0.020 inches.

Certain areas of the anchor 250 can be widened, such as feet or contacting portion of projections 252, 254 to present a desired contact pressure at an annulus. These projections can have a height ranging from 8-12 mm, a surface area of 6-15 mm$^2$, and width and lengths of 2-3 mm and 3-5 mm, respectively. Also, by embodying the flat or ribbon profile, thinner material can be employed in the anchor 250, thus facilitating deliverability by enabling the device to be compressed to a smaller dimension. The ribbon structure also lends itself to improved results to material fatigue where a wider aspect of the ribbon can be placed or configured to offset forces. It is to be further recognized that the anchor 250 is contemplated to be covered with material for ingrowth and other functional reasons. For example, as with the embodiment above, material covered aprons function to aid in directing blood flow from the atrium to the ventricle.

Figure 24:
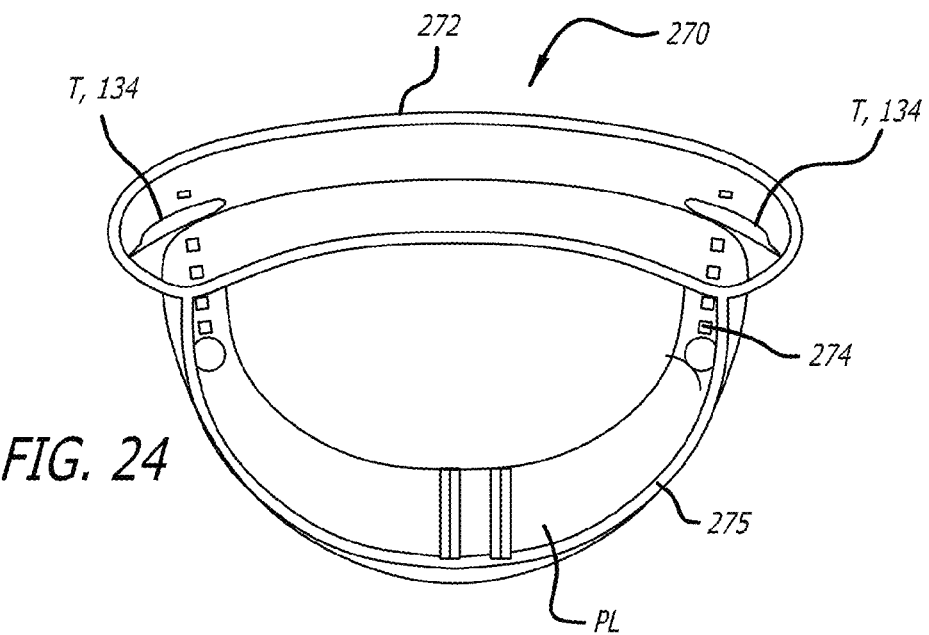
FIG. 24 is a top anatomic view, depicting an anchor with forward projecting commissural projections or feet.
Figure 25:
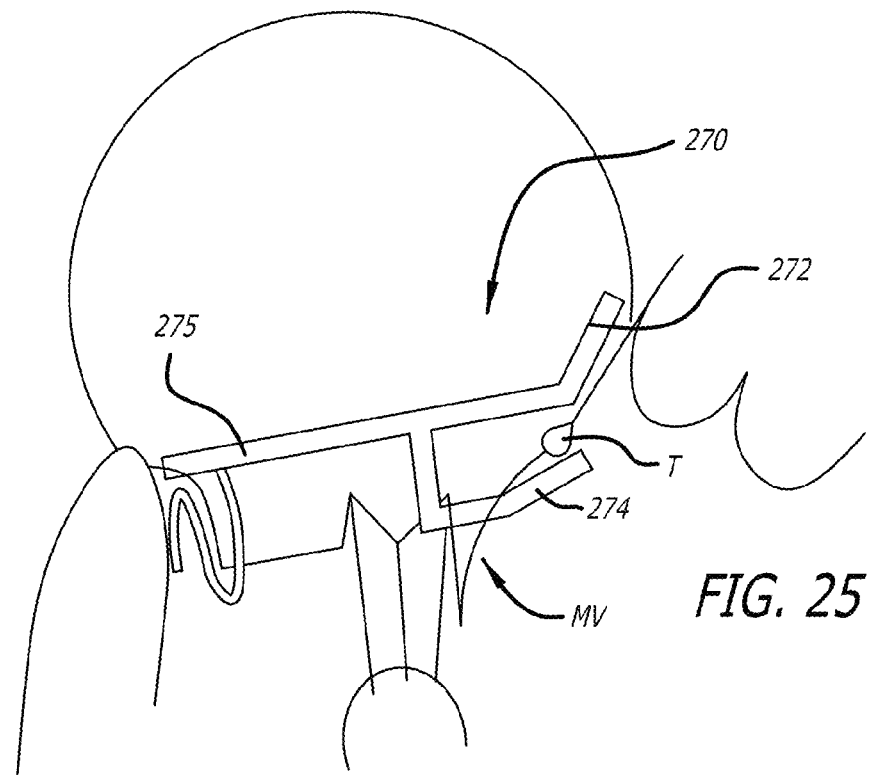
FIG. 25 is a side view, depicting the anchor of FIG. 24.

Turning now to FIGS. 24 and 25, there is presented a schematic representation of an alternative embodiment of a frame of an anchor 270 placed at a mitral valve MV. This particular approach to an anchor 270 includes an anterior apron 272, but lacks a posterior apron. Anterior projections 274 extend from a generally D-shaped central ring 275 and engages directly under the trigones T. A pair of posterior projections 275 also extend from the central ring 275 and into the gutter adjacent the posterior portion of the posterior leaflet PL.

Figure 26:
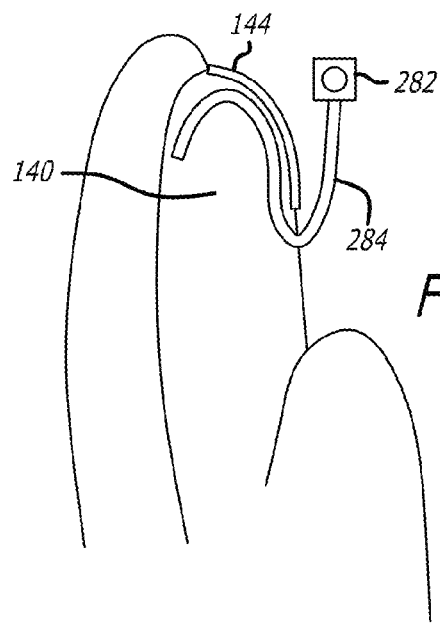
FIG. 26 is a side cross-sectional view, depicting clip structure of an anchor configured within anatomy.
Figure 27:
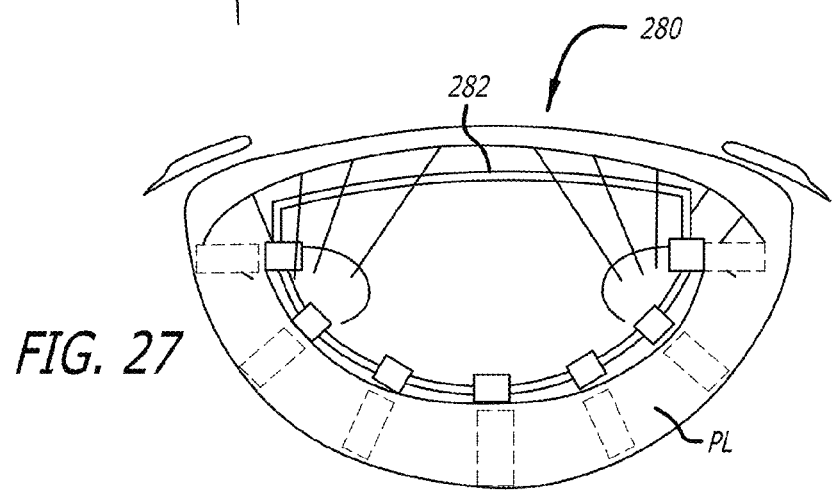
FIG. 27 is a top view, depicting an anchor with clip structure placed about an open valve.
Figure 28:
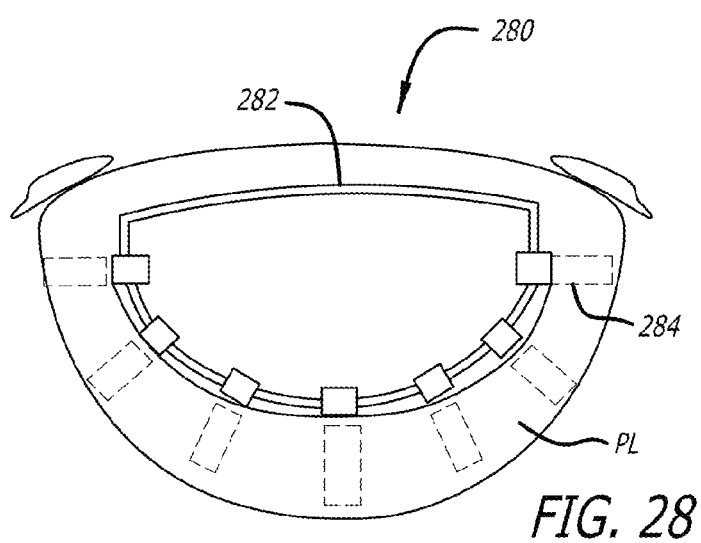
FIG. 28 is a top view, depicting the anchor structure of FIG. 27 placed about a closed valve.

In yet another approach (FIGS. 26-28), an anchor 280 can include a generally D-shaped ring 282, and a plurality of projections 284 extending from the curved side of the D-shape. As described before, the projections 284 are sized and shaped to extend to within the gutter 140 to accomplish a seating and securing function. In the embodiment depicted, the posterior leaflet PL is essentially captured by the projections 284. Thus, in a replacement approach employing this anchor 280, it may be desirable to immediately follow up implantation of the anchor 280, with the insertion of a replacement valve. In the meantime, the anterior leaflet can provide adequate coaptation until the valve is set.

Figure 29:
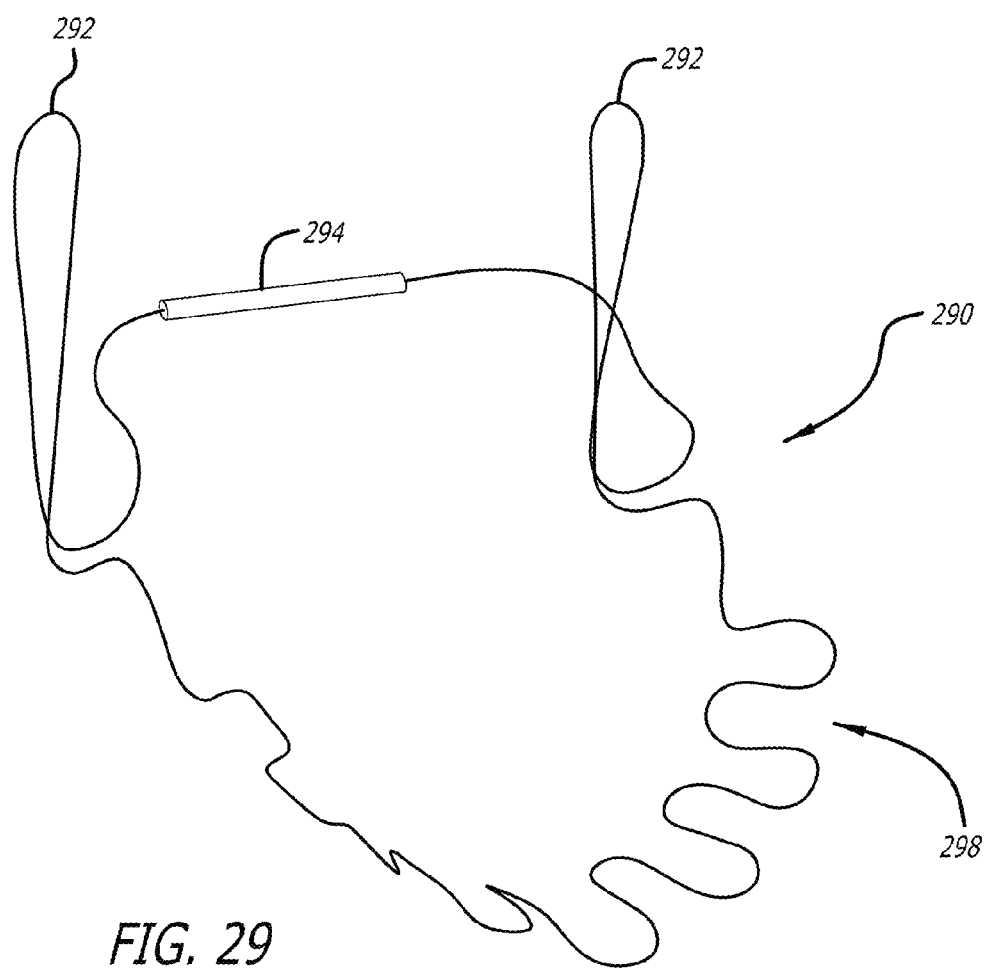
FIG. 29 is a perspective view, depicting the anchor of FIGS. 24 and 25.

FIG. 29 depicts yet another approach to an anchor device 290. Anterior projections 292 are sized and shaped to be received within and engage directly under the trigones adjacent the anterior portion of a valve annulus. An anterior crossbar 294 provides stability to the anchor 290 placed at or near a valve annulus. A posterior portion 295 of the anchor 290 defines a sinusoidal shape and can be designed to hold the posterior leaflet of a mitral valve. Again, the anterior leaflet of the valve will provide a closing function by engaging the sinusoidal portion 295 of the anchor device 290. The loading of this anchor 290 is primarily curved by the leaflet tips to the chordae connecting the posterior leaflet.

As stated, staging is the ability to stage the implantation of valve structure so that it could be deployed in the same procedure as that of the implantation of anchor and sealing structures, or thereafter. As the anchor and sealing structures grow into and are incorporated in the tissue/existing anatomy, the holding capability of these structures increases until such time as the valve/assembly is deployed, either automatically (e.g., suture dissolving over time) or by some trigger mechanism or actuation during a second procedure. This actuation could be achieved remotely without invading the body (e.g., RF or ultrasound-like actuation).

The valve replacement system according to the present disclosure allows for valve delivery flexibility. Specifically, tissue valves can be delivered either via a fully percutaneous procedure or a minimally invasive surgical delivery of the valve without modification to the valve implant to accommodate the alternative route.

Yet another aspect of having a stable consistent anchor platform for receiving a valve structure is that it allows for valve sizing that is appropriate for the patient population (FMR, structural, mixed) and even specific to the patient being treated. In other words, it allows for the largest valve possible in every patient rather than compromising size (smaller than physiologically desired) to accommodate technology limitations in systems that must combine multiple (increase complexity) valve, attachment, sealing and delivery structures.

The system according to the present teachings also allows for therapeutic flexibility of the artificial valve. The presently disclosed system allows for beating heart implantation of both tissue and mechanical valves. As disclosed herein, delivery systems are provided that allow implantation of mechanical valves via either a trans-apical or trans-atrial thorascopic route.

Moreover, while surgical tissue replacement valves in the mitral position have conventionally often been basic and inverted modifications of the tri-leaflet aortic counterpart, the percutaneous delivery requirements (collapse/expand) of the TMVR allows for designs specific to mitral position on several functional requirements. For example, there is sufficient size for blood inflow so as to not trade regurgitation for stenosis. One key aspect is that in functional MR with native annular dilatation, the replacement valve does not need to fill the whole annular area of the now dilated annulus. A smaller area can be used while still creating sufficient size to prevent any inflow obstruction/stenosis. Also, it is desirable to maintain LV chordal connections and geometry to maintain LV functional geometry and stress configuration. Cutting or disruption of the chords can create significant increases in LV wall stress and resultant loss of cardiac function.

A durable valve design balances sufficient valve height relative to the diameter to prevent excessive post loads and leaflet stresses. In the mitral position (vs. aortic) this is accentuated with the generally larger valve diameter requirement (lower through flow pressure) and the higher valve loads encountered when closed (LV systolic pressure vs. diastolic aortic pressure). In surgical replacement mitral tissue valves, the valves are designed for the base to be sewed to the annulus and the stent leaflet posts extending from the base, but are short to minimize LV depth to prevent outflow tract obstruction or native leaflet entanglement. In these valves, the base also tends to be designed as a cylinder and therefore is not extended into the atrium to prevent potential pockets of stagnated blood.

Sealing against the native valve is to be a consideration. A valve that relies on radial expansion and or compression to create the seal requires a valve frame that is larger than the native annulus and a larger radial force to create the interface. Sufficient anchoring interface and holding is also an important consideration. Valves that rely on frictional interface to create anchoring force require relatively larger radial expansion force capability increasing the complexity of the stent frame. Ability to collapse into a deliverable configuration and then reliably expanded configuration can be addressed as well as the prevention of LV outflow tract obstruction. Too great of an encroachment into the LV beyond the native mitral annulus can impact the position and function of the native anterior leaflet. If it is pushed too far down and out, it can be pulled into the outflow tract during systole creating functional obstruction of the LV outflow tract. Moreover, prevention of flow stagnation regions to prevent clot formation and embolization can be important on both the atrial side as well as the ventricular side, specifically in the sub-leaflet gutter region.

Regarding these final two considerations, aortic valves that are being modified to use in mitral position as well as surgical valves conventionally all have a generally tubular design at their base region or beyond up into the commissural post region. This tubular design that bridges across the native mitral valve has the possibility of creating outflow tract obstruction and pockets of stagnation behind the valve and native leaflet region if it extends too deep into LV or can create significant flow stagnation regions if the "tube" extends too far into atrium with blood having to flow up and over the valve base to reach LV during diastole. Additionally, the use of a tubular symmetric valve in a D-shaped mitral annulus may result in uneven distribution of stresses across leaflets and therefore reduced durability.

Thus, in one contemplated embodiment of a percutaneous replacement mitral valve, there is structure for facilitating an optimum valve for the mitral position. With respect to atrial biased positioning, the contemplated valve is positioned with a bias to the atrial side with the LV side only extending to or short of the commissural and posterior leaflet tips when they are in the diastolic position (vertical to LV wall). This allows for minimal interference with native leaflets and chordal connections, minimizing engagement and interference with the anterior leaflet therefore minimizing potential for outflow tract obstruction, minimizing sub-leaflet (LV side flow stagnation and potential for clot formation and embolization, and allows for sufficient valve height to manage commissural post strain and leaflet stresses. Taller or longer leaflets for a given valve diameter have smaller leaflet stresses.

The contemplated approach is also contemplated to embody a "ring in ring" stent design. Here, this is an inner ring for large circular leaflet/occluder geometry for optimum function and durability. The inner ring can consist of the 3 commissural posts joined by the 3 arches and the 3 leaflet cusps sewn to the posts and arches. This structural relationship that allows the outer ring to deflect and adapt to the non-circular native anatomy while maintaining circular inner geometry allows for overall better valve performance and maximizes durability. Another aspect of this configuration is that the leaflet excursion during diastole where the leaflets define a circular shape is that the leaflets do not impact or come into contact with the outer support frame/ring reducing the likelihood of damage to the leaflet tips as can happen with an overall circular support frame. Moreover, it is contemplated that the leaflets can be formed from glutaraldehyde fixed pericardium or aorta cusps from one or more of a bovine, porcine, ovine or equine, and having a thickness of 0.005-0.020 inches or specifically between 0.008-0.012 inches and being anisotropic (collagen fibers circumferentially oriented) such that modules in one direction is higher than another (E circumferential>E radial).

The replacement mitral valve also includes central support of commissural posts (vs. base) to minimize cyclical strain and improved durability. Loading during leaflet closure is translated to the posts and creates tip deflection toward the valve center. Having the posts supported more to the middle of the overall stent frame helps minimize cyclical strain and therefore improves durability. The longer posts and leaflet height combine with a more centrally supported post to improve overall durability due to more uniform distribution of stresses between the leaflets. Further provided is an outer ring for adaptable sealing interface and native valve engagement. The outer ring can adapt to the native leaflet and valve shape and size while maintaining the central core inner ring.

The contemplated replacement valve can also include a scalloped or arched leaflet cusp design. With the more atrial positioned valve, the scalloped arches or cusps help minimize atrial flow stagnation both during diastole when the leaflets are in the open position, the blood flows between arches which sit proximate the native annular height, and during systole as the backside (non-leaflet side) of each arch is also pressurized and creates dynamic motion behind the cusps. Traditional tubular design valves have no such capability. With the leaflet cusps sewn to the arches, there is also efficient load transfer from the leaflets to the arches and then to anchor structure, also minimizing stent deflection/strain and enhanced durability.

The replacement valve is also contemplated to include a receiver waist for engagement with the anchor. The waist of the valve engages with the anchor ring structure to provide for a simple geometric interlock for load transfer to the anchor rather than frictional fit to anchor or the native valve. Therefore, the radial strength of the valve is less than required if a frictional fit was used; it needs to be properly sized, but does not require radial force expansion into the anchor ring.

Additionally, collapsibility, expression, repositioning, and recapturing of valve are all further requirements or desirable aspects of the overall valve design. The current embodiment has several elements that contribute to an improved capability to perform these functions. That is, the potentially lower radial force required for the overall valve design can allow the valve to collapse with less force both initially during insertion into delivery catheter, as well as when the valve may need to be partially collapsed for repositioning, or fully collapsed for recapture and removal. Also, the arches of the valve create an improved leading edge (rather than a collapsed cylinder) for the valve to be retrieved into the delivery sheath if needed, provide natural points of holding and individual control during expression and deployment, provide lower regional outward radial force that facilitates holding during deployment into the anchor as well as during recapture. The arches or scallops can allow the valve to partially function during placement for a more controlled implant with less potential for negative hemodynamic consequences to the patient. Also, attachment to the arches allows for functional assessment of valve prior to final release. The three points of proximal hold also create the ability to control the planarity of the waist section of the valve so it becomes coplanar with the anchor prior to full deployment. The three inner posts also may provide a distal holding point during delivery.

Accordingly, referring to FIGS. 30-38, there is presented one particular approach to a valve 300 embodying a number of the above-identified desirable valve features. Various views of the valve frame 310 alone are set forth in FIGS. 30, 32, 35 and 36 to provide a sense of its overall structure. In FIG. 30, only the foreground structure of the frame is shown so that a repeating pattern can be best appreciated. FIG. 32 shows a top view of the cylindrical D-shape of the frame 310.

Figure 36:
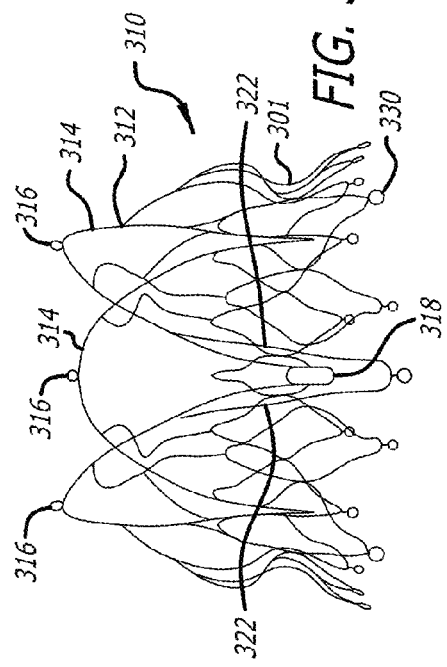
FIG. 36 is a side view, depicting the wire frame of FIG. 35.
Figure 35:
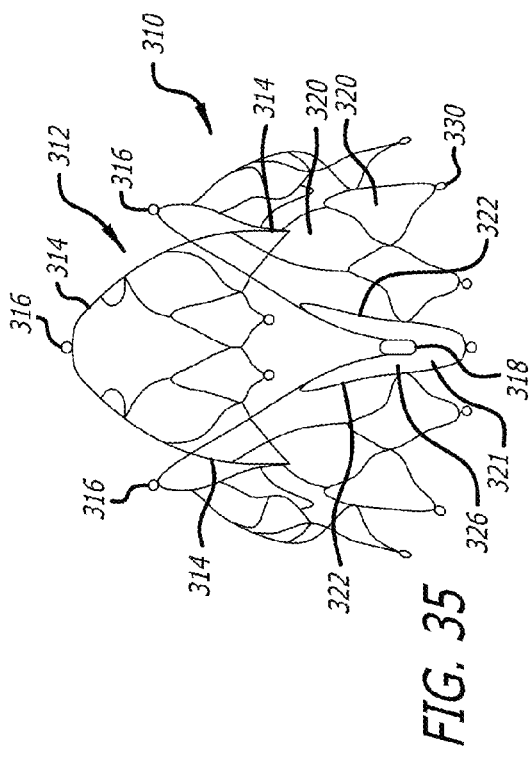
FIG. 35 is a perspective view, depicting another approach to a wire frame for a valve assembly.

As best seen in FIGS. 32, 35 and 36, the frame 310 includes an undulating ring 312 having three arches 314. Each arch 314 defines a generally parabolic profile having a loop 316 at its apex and adjacent arches 314 being connected at their bases to form commissural posts 318. In one particular embodiment, the members defining the frame have a thickness of up to 0.012 to 0.024 inches, and can be in the range of 0.016-0.018 inches.

Attached to anchor ring 310 are a plurality of closed cells 320. Although the cells 320 can assume various shapes, as shown, when expanded, each cell includes upper and lower narrowed ends and a wide mid-section. There is an interrupted first row of such cells 320 circumventing a bottom portion of the frame 300, such cells 320 being interrupted by a half cell 321 longitudinally aligned at each commissural post 318. A second interrupted row of cells 320 are connected to and reside up above the first row of cells 320. Upper curved arms of the lower set of cells 320 define a lower section of the interrupted upper row of cells 320. The upper row of cells 320 are interpreted by members of adjacent arches 314 leading to the commissural posts 318. Additional support is provided by extending members 322 extending from upper ends of members defining the half cells 321, to thereby define a larger V-shaped cell 326 encompassing each of the commissural posts 318. Curved arms also extend from the upper narrow portion of the second row of cells 320 to an arch. Further, configured at the base of each of the closed cells 320 and the half-cell/V-shape cells 321, 326 are loops 330. Such loops can be engaged by device delivery structure for accomplishing implantation. FIG. 32 in particular depicts an isosceles triangle arrangement of the inner posts (ring).

As best seen in FIGS. 30, 35 and 36, the frame embodies a waist 301. As described above, this waist 301 is sized and shaped to receive an anchor implant. In one embodiment, the waist is 18-34 mm anterior to posterior, and 20-44 mm commissure to commissure. A ratio between the same can be 0.5 to 1. Moreover, when applying tissue or fabric 333 to the valve assembly 300, as shown in FIG. 31, the waist remains. Flaring of the valve assembly can result in an anterior to posterior dimension of 20-40 mm, a commissure to commissure dimension of 24-50 mm, and a ratio between the same of 0.05 to 1. The total valve height can be 20-36 mm (with the underlying frame having a post to arch tip dimension of 20-36 mm), and the valve can embody a 17-33 mm effective diameter.

Figure 33:
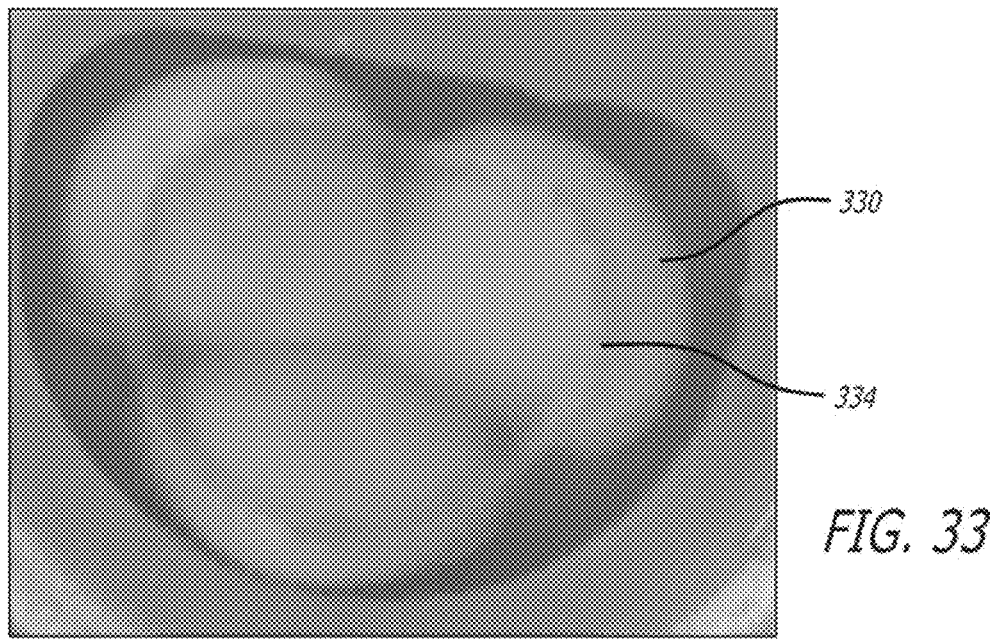
FIG. 33 is a top view, depicting the valve frame of FIG. 31 placed within simulated anatomy.
Figure 34:
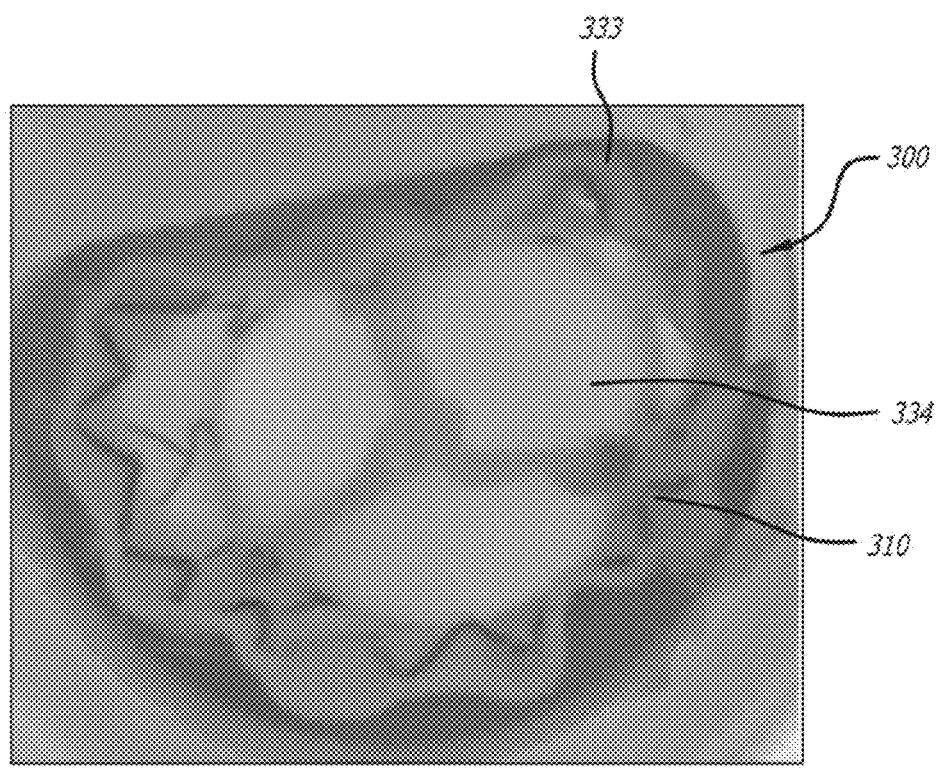
FIG. 34 is a bottom view, depicting the valve of FIG. 31 placed within simulated anatomy.
Figure 38:
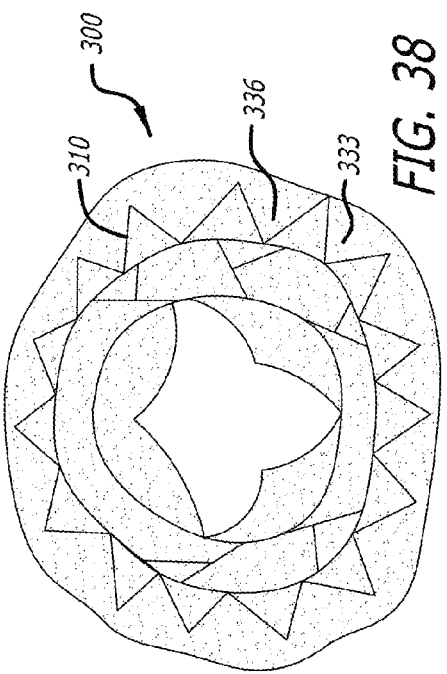
FIG. 38 is a bottom view, depicting the valve frame of FIG. 37 in an open position.
Figure 37:
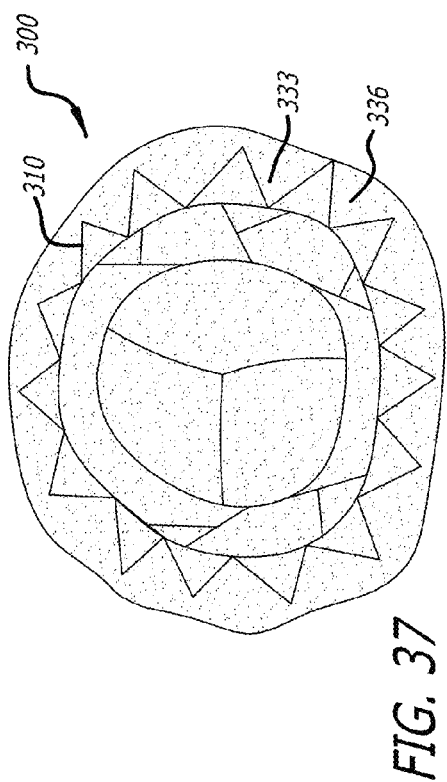
FIG. 37 is a bottom view, depicting a covered valve frame in a closed position.

With reference to FIG. 33, a top view of the valve assembly 300 is shown implanted within an interventional site. It is noted that while the indentation region of the assembly can resemble a D-shape, the valve orifice 334 is generally circular for optimal valve performance. FIG. 34 provides a bottom view of a closed valve assembly 300 implanted at an interventional site. FIGS. 37 and 38 are provided to show ventricular views of an implanted valve assembly 300 in closed and open positions, and with a flaring 336 of the valve frame 310 and tissue or fabric creating a component sealing surface with anatomy.

Figure 39:
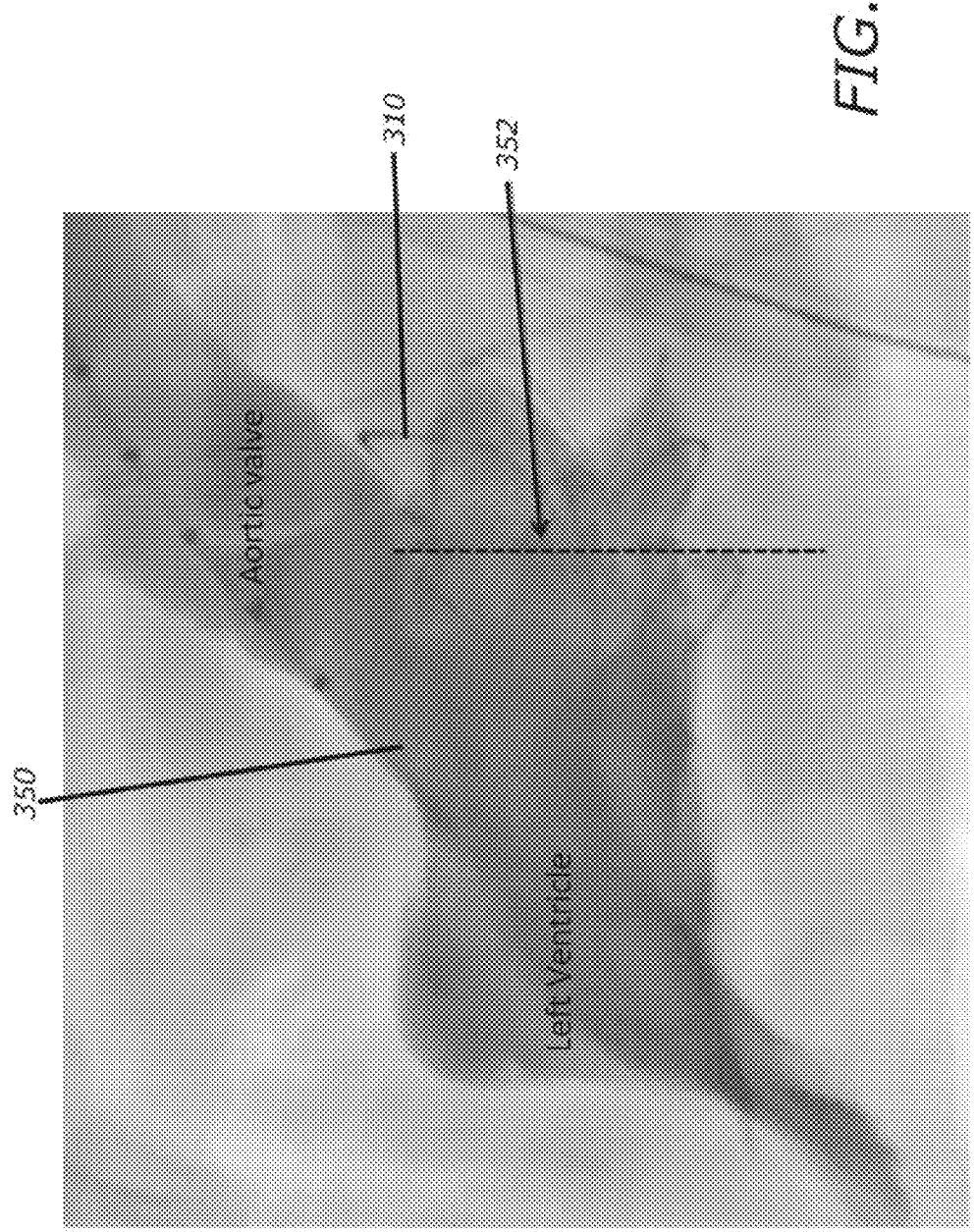
FIG. 39 is a fluoroscopic side view, depicting the valve of FIG. 31 placed within tissue.

An anatomical side view of the valve assembly within tissue is represented in FIG. 39. Here, a fluoroscopic dye 350 has been injected into the left ventricle area to assist with showing anatomy via fluoroscopy. The dashed line follows the native mitral valve plane 352. The frame 310 of a valve assembly can be seen implanted above the left ventricle. Note that the dye is contained within the ventricle, indicating good valve performance by the implanted valve assembly.

The requirements of the sealing interface with the native valve include ventricular to atrial sealing during systole, atrial to ventricular sealing during diastole, and stable chronic sealing that results from ingrowth incorporation of the sealing interface with the native valve. One approach to sealing is to utilize a native tissue engagement structure with the native leaflets along the annular perimeter to create a LV pressurized seal. This is not a mechanically compressive or attachment (active fixation) seal onto the native tissue. It also requires minimal or no radial expansion beyond the tissue engagement interface. In one contemplated embodiment of the percutaneous mitral valve, the frame is externally covered by tissue. During systole, the tissue expands radially reaching out to the native valve to create a paravalvular seal. The external tissue also expands radially on the atrial side cuff (outer covering on valve) to create a supra annular seal during systole.

Figure 40:
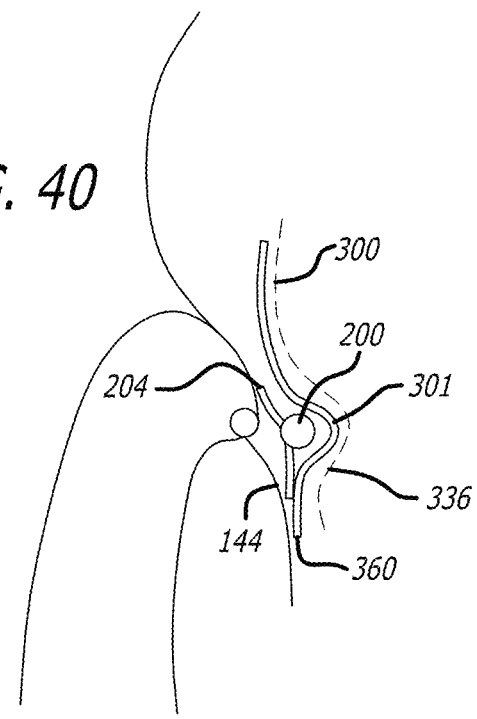
FIG. 40 is a cross-sectional side view, depicting a sealing skirt of a valve assembly.
Figure 40A:
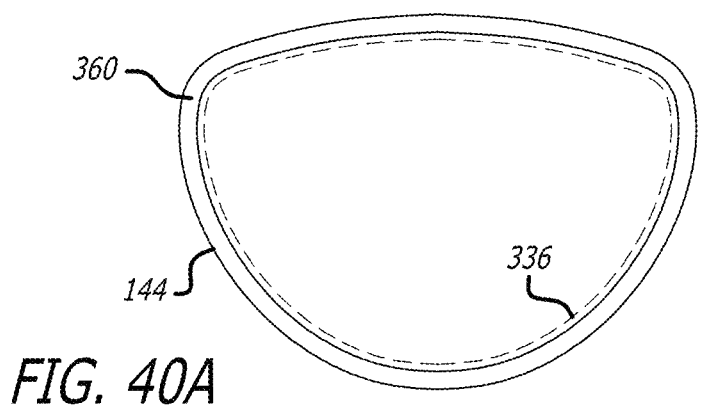
FIG. 40A is a cross-sectional top view, depicting a sealing skirt of a valve assembly.

As shown in FIG. 40, an anchor frame 200 covered with fabric 204 can be placed proximate an annulus of a natural valve including leaflets 144. A replacement valve assembly 300 is placed into engagement with the anchor 200 by positioning the waist 301 of the valve assembly so that it receives the anchor 200. Thus, fabric such as Dacron of an anchor frame is placed adjacent native tissue on both ventricular and atrial sides of a valve annulus thereby facilitating a seal. Pericardial tissue (e.g. one or more of glutaraldehyde fixed ovine, equine, porcine or bovine pericardium having a thickness of 0.0005-0.036 inches, or 0.05-0.014 inches) 360 is further provided on the valve assembly 300. The fabric 204 of the anchor 200 interfaces with the biological tissue 360 of the valve assembly 300, thus facilitating a seal between the anchor 200 and valve 300. Moreover, the atrial position of the valve 300 is selected to facilitate a sealing surface to be at or near a collar of the valve frame and adjacent to the valve annular region to endeavor optimizing overall perimeter engagement of the sealing surface as seen in FIG. 40A taken in cross section just below the Dacron 204 of the anchor (i.e. anterior leaflet region, commissural region, posterior leaflet region).

Next, imaging and implantation is discussed. Relevant aspects of imaging are to evaluate valve function pre- and post implantation, and to facilitate proper positioning of the implant components. Echo imaging, either ICE or TEE is sufficient and available for valve function assessment. Imaging for device position is more complex and requires establishing repeatable and consistent views (imaging planes) and reference landmarks (device relative to anatomic structure or other device) to reliably and accurately position the system. Imaging for device placement preferably also includes fluoroscopic imaging.

Figure 41:
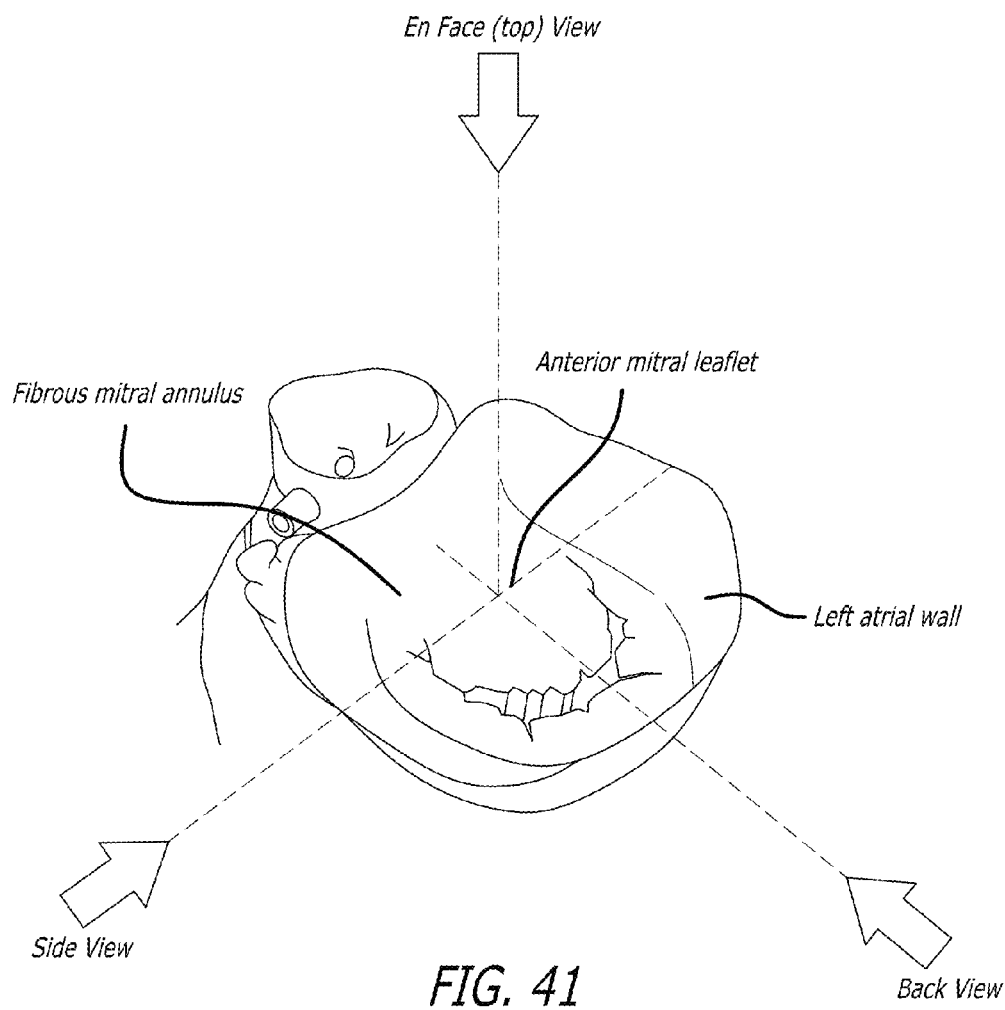
FIG. 41 is a perspective view, depicting heart anatomy and desired imaging planes.

As shown in FIG. 41, side, top and back views of a mitral valve comprise the orthogonal views which are useful in an implantation procedure. As described below, once an orientation tool is in position across a mitral valve, using a self-orienting loop with tactile feedback, C-arms of a fluoroscopy machine are lined up with markers on loops of the orientation device to establish registration angles that correspond with views relative to the mitral valve for delivery and replacement components. By doing so, the mitral valve, which is not easily visible on fluoroscopy, can be confidently targeted by virtue of properly aligned angles on the fluoroscopy machine.

Figure 42:
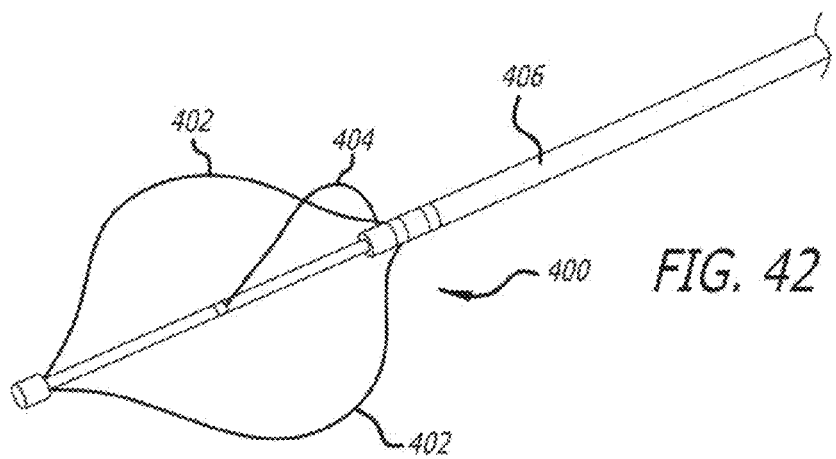
FIG. 42 is a perspective view, depicting an orientation tool.
Figure 43:
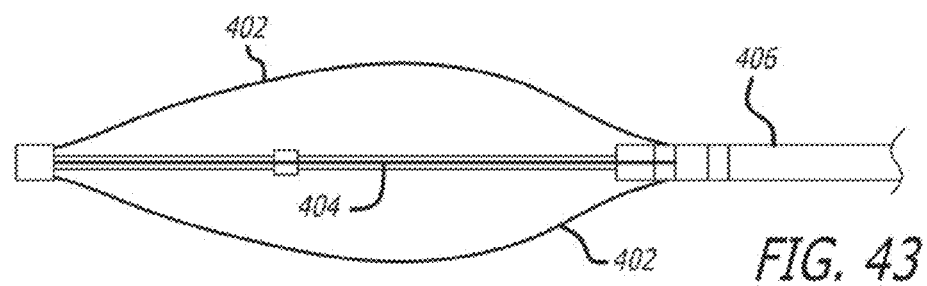
FIG. 43 is a side view, depicting the orientation tool of FIG. 42.

One approach to understand in the intra-procedure device position is to establish orthogonal views of the valve annulus, ventricle, and atrium. In order to assess target anatomy, an orientation loop 400 (See FIGS. 42 and 43) can be placed in the coaptive margin between the anterior and posterior leaflets, and employed to establish implantation sites and reference points.

Figure 44:
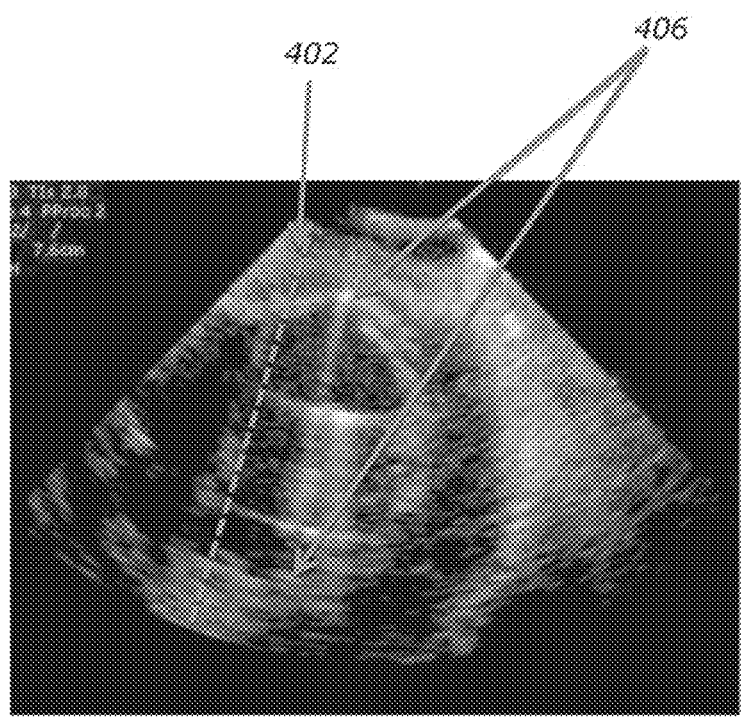
FIG. 44 is a schematic representation of an echo image, depicting use of an orientation tool within anatomy.
Figure 46:
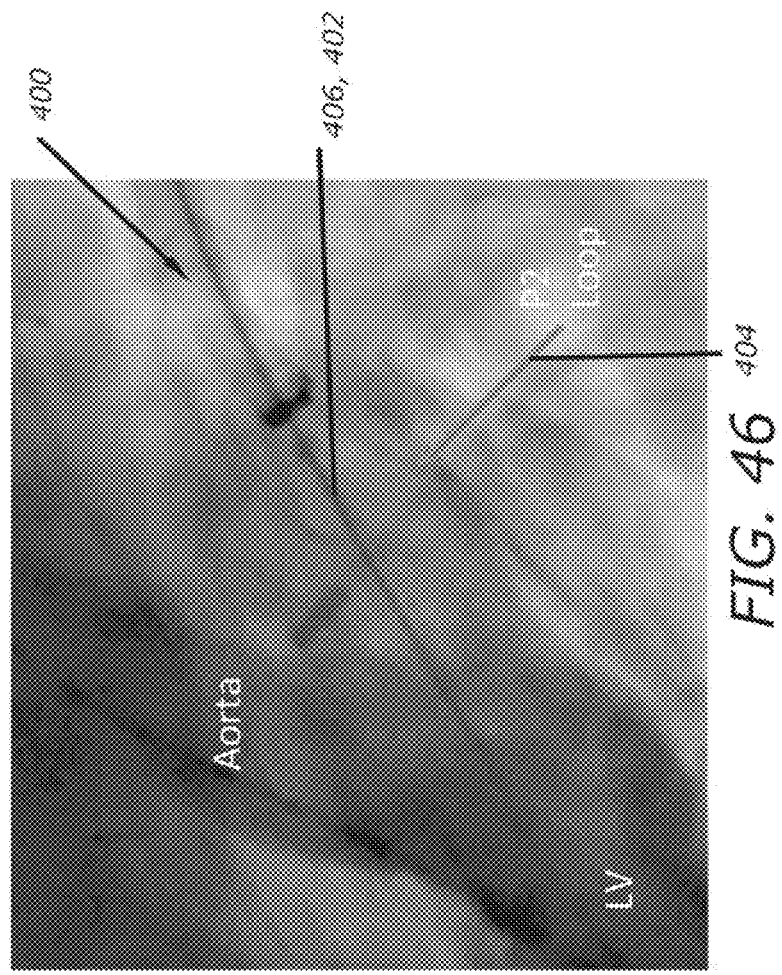
FIG. 46 is a fluoroscopic side view, depicting yet further use of the orientation tool within anatomy.
Figure 45:
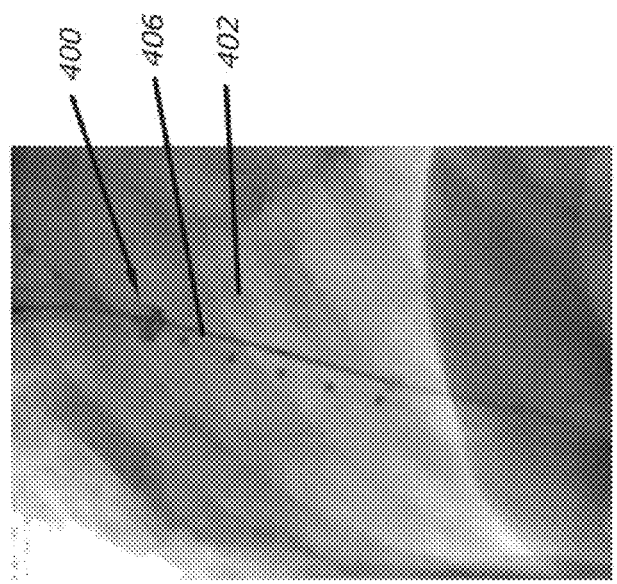
FIG. 45 is a fluoroscopic side view, depicting further use of an orientation tool within anatomy.
Figure 47:
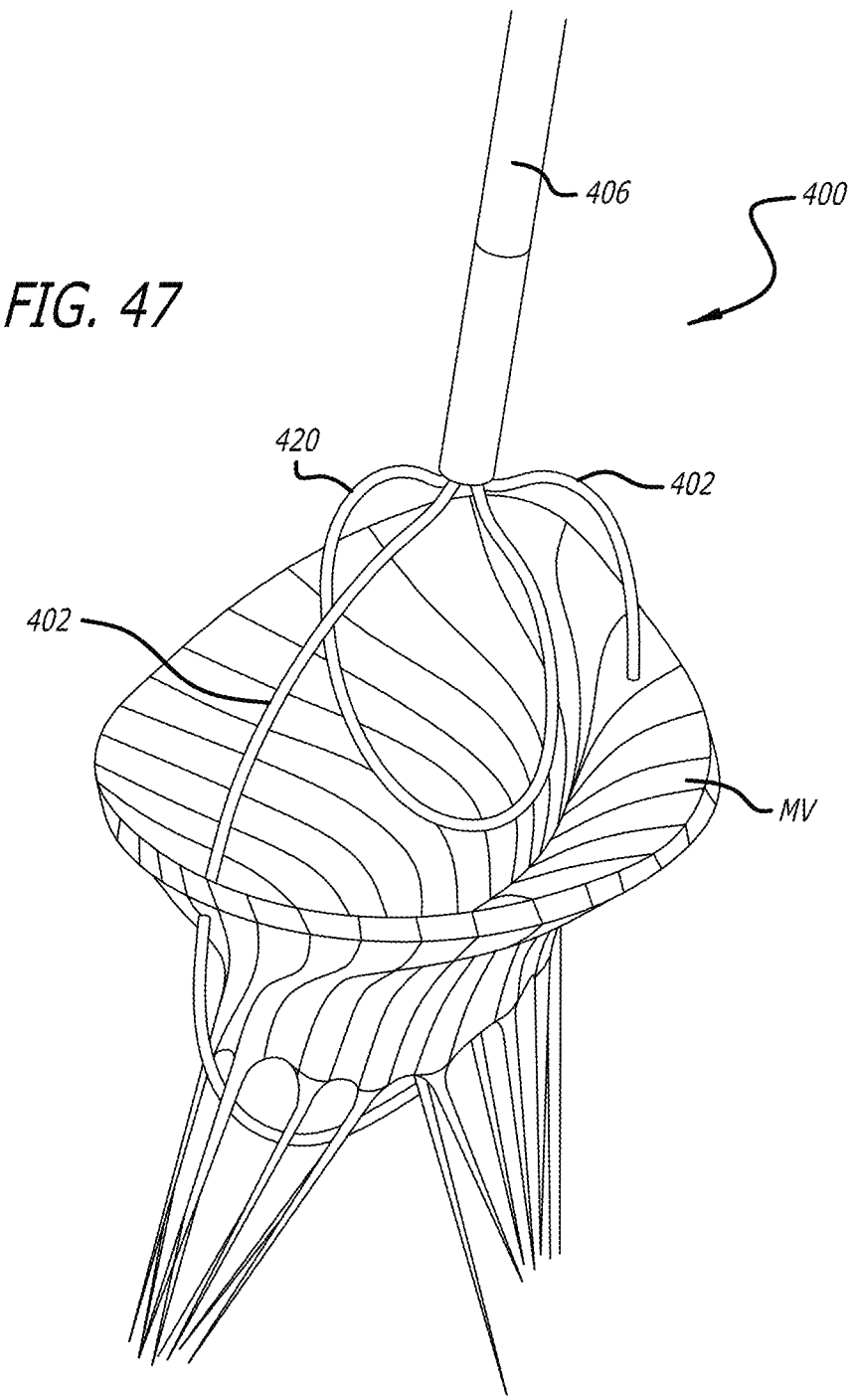
FIG. 47 is a perspective view, depicting an alternative approach to an orientation tool.
Figure 48:
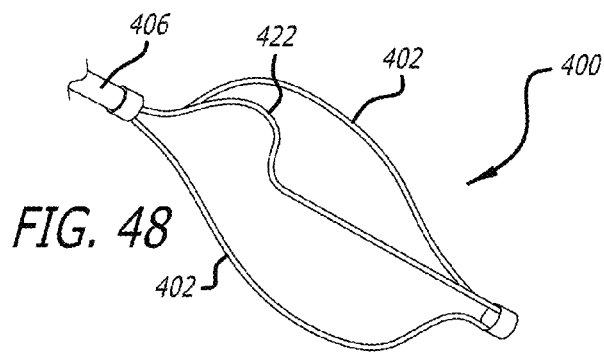
FIG. 48 is a perspective view, depicting further details of the orientation loop of FIG. 42.
Figure 49:
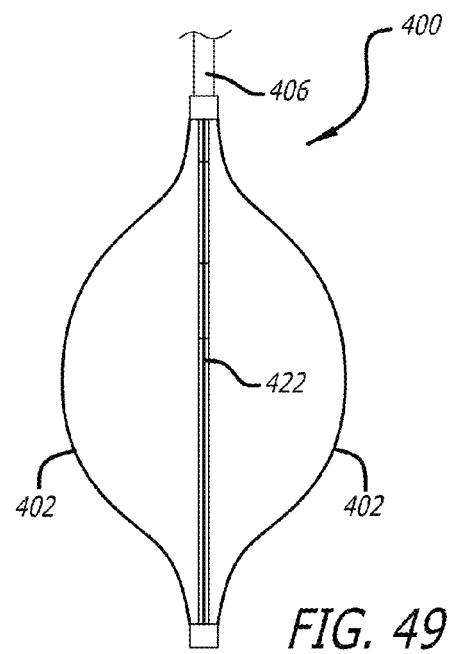
FIG. 49 is a back view, depicting the orientation tube of FIG. 48.
Figure 50:
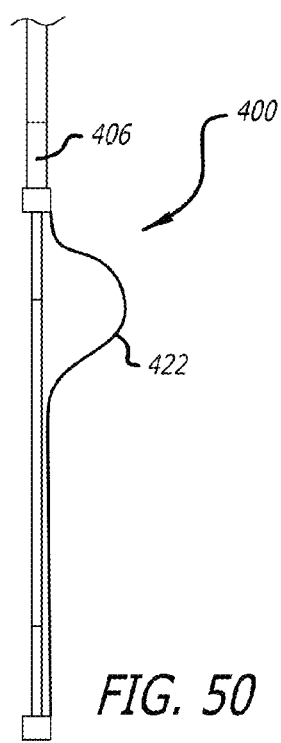
FIG. 50 is a side view, depicting the orientation tool of FIG. 48.
Figure 51:
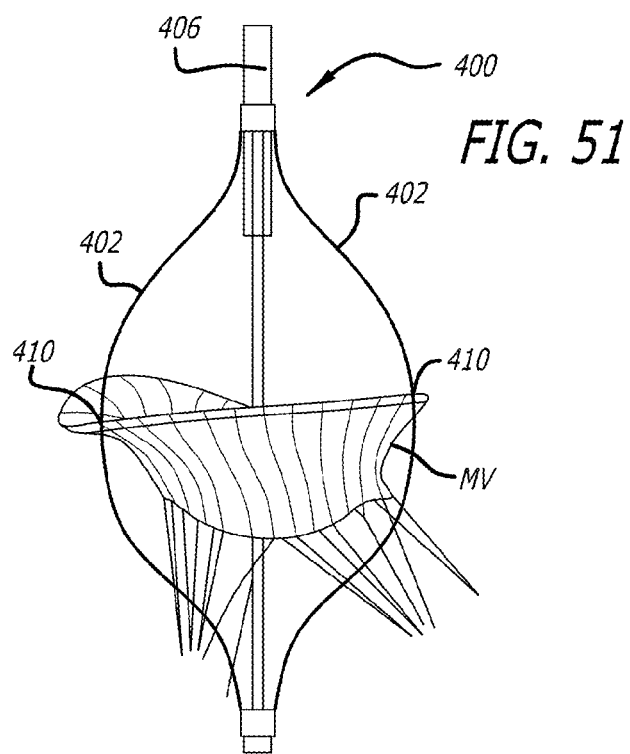
FIG. 51 is a side view, depicting further details of the orientation tool of FIG. 49.
Figure 52:
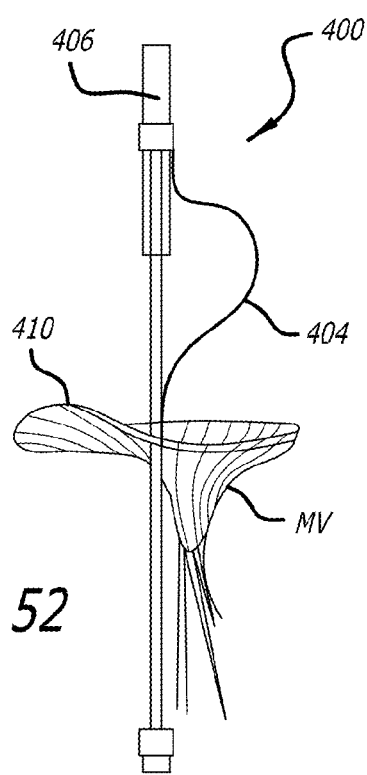
FIG. 52 is a rotated side view, depicting yet further details of the orientation tool of FIG. 50.
Figure 53A:
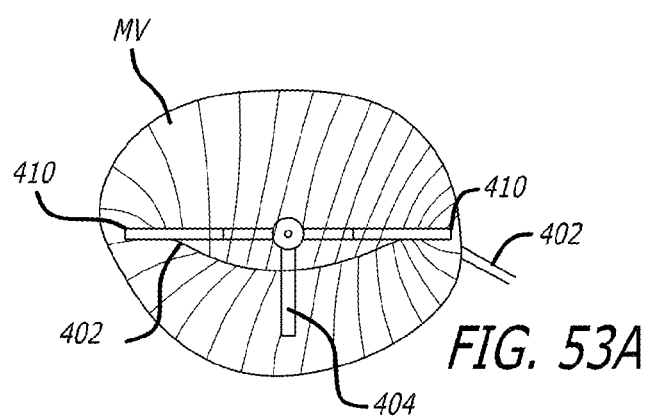
FIG. 53A is a top view, depicting use of the orientation tool.

In one approach, a catheter 400 is provided with orthogonal loops/structures, one large 402 and one small 404 that can be advanced into and above the valve, respectively, and can be attached to an elongate member 406 extending from the loops to an operator. It is to be noted that the large loop will be positioned within the coaptive margin such that the anterior and posterior chordal tents will orient the frame based on the leaflet tips engaging the sides of the frame and possibly more importantly, the chordal tent plane between the anterior and posterior chords engaging along the entire sub-valvular extent of the loop 402 (See also FIG. 44). The distal (bottom) end of the smaller loop 404 will be positioned at the valve plane by both tactile and fluoroscopic visualization (bounce/deflection) as it interacts with the leaflets. FIG. 45 depicts the use of the orientation loop 400, showing the large loop 402 fully expressed and the small loop 404 in alignment with the elongate member 406. FIG. 46 is a side view showing the larger loop 402 fully expressed/expanded, both arms of which being in alignment with the elongate member 406 and the small loop 404 extending over the valve leaflet.

Referring to FIGS. 51-53A, one can further appreciate the positioning of an orientation loop within valve anatomy. Again, the tool 400 is placed through a valve MV and positioned so that the large loops 402 of the device are placed along the coaptation margin of the valve. By registering markers 410 positioned at the extreme width of the large loops 402, as stated, the angles of the views can be registered for fluoroscopy and ultrasound equipment for later use in anchor and valve placement and orientation, knowing that the orientation of the anchor and valve themselves will not be easily identified by remote visualization. Measuring the native annulus dimensions via the orientation loop markers 410 with fluoroscopy can also be performed. FIGS. 53B-E depict further detailed structure which can be relied upon to determine orientation. Markers 410 can be banded, including dark regions 412 and light regions 414. They can also include a plurality of radiopaque or other aligning dots or sub-markers 416. The relative position of the aligning dots 416 can be used to determine the rotational position of a marker 410, and thus the structure to which it is attached (See FIGS. 53B-C). Moreover, axial alignment of a marker 410, and thus the structure to which it is attached, can be determined by observing whether an angled (FIG. 43D) or true side view (FIG. 53E) is presented.

These two frame loops 402, 404 can thus assist in establishing the desired camera positions for back, side, and En face (top) views (views shown in FIG. 41). By moving the camera (not shown) until the image indicates two orthogonal lines (en face), one large loop with short line in top center (CC Side View), or one small loop with long line extending through loop and down into the left ventricle. Further, the commissural line and position can be established based on the large loop 402 orientation being parallel to commissures which can be confirmed in the short axis echo image which will indicate commissural points and two "dots" indicating cross section through the large loop. In this way, a determination can be made concerning the location of the valve leaflet plane during systole. Next, a guide catheter tip can be oriented to be directed at the valve center in the x, y, and z axes via the wire extension from the loops being linear with each loop in each side image plane to thereby establish imaging planes.

Alternative embodiments of an orientation tool are provided in FIGS. 47 and 48-50. In one approach, the orientation tool 400 can include the large loops 402, but the elongate member 406 terminates at the beginning of the loops, or the device otherwise lacks a generally straight longitudinal member extending through the loops. Moreover, a small loop 420 is defined by a generally circular member configured orthogonally to the large loops 402. The orientation device 400 shown in FIGS. 48-50 resembles that presented above in connection with FIGS. 42 and 43. The small loop 422 defines a path like the small loop of FIGS. 42 and 43, but again, lacks an extension of the elongate member passing therethrough.

It is to be noted that the dual orthogonal loop structures can be used as a structure to pass cleanly through the mitral sub-valvular apparatus without chordal entanglement. Once the imaging planes are established, reference landmarks can be used to direct the insertion of an anchor, especially on depth relative to the valve plane. In particular, the depth of the leaflet tips during diastole could be established for foot insertion depth.

With respect to orientation/positioning methods, utilizing a separately implanted anchor substrate is the ability to utilize a fluoroscopic alignment technique to mesh the anchor with the valve. In this scenario, the x-ray fluoroscopic camera could be adjusted so a radiopaque (complete or interrupted around perimeter) anchor structure would be visualized in a relatively straight line (camera orientation—line connecting emitter with intensifier—is perpendicular to anchor circular axis, or parallel to plane of anchor ring). The valve frame structure could similarly have a radiopaque perimeter at the point at or near the interlock region with the anchor. When the anchor was viewed in the manner described, the valve axial orientation could be adjusted so the radiopaque perimeter was also a line (without moving camera position) meaning the two cylindrical axes of the anchor and valve were now parallel. Subsequently, the valve line could be appropriately positioned above, below, or at the interlock region. This linear alignment of the two radiopaque structures would be even more visually pronounced as the valve frame was being expanded/deployed, whether by balloon or self-expanding. This could additionally allow for fine tuning or adjustment prior to final engagement of the valve with the anchor structure.

General fluoroscopy based methods can be used to evaluate use of markers/overlays on a fluoro screen within the same camera/table position. It is noted that some equipment has built in marking capability within an image view. Further, device length markers in the form of a pigtail with 1 cm marks (useful in the Back view where pigtail is running through center of image) can be employed as can a wire with 1 cm marks along distal length, such as 1 cm marks on the pusher shaft. Further, dye injection methods are contemplated to better view sub-leaflet structure (with a curved diagnostic catheter placed sub-P2). Visible or augmented anatomic landmarks are of course to be considered including use of a guidewire in circumflex and tracking of the ICE probe or guidewire into coronary sinus. Finally, evaluations using echo LAX views to see leaflet tips in foot locations are contemplated.

After setting remote visualization equipment using the orientation tool, it is contemplated that a positioning frame may be used to guide and support the delivery and positioning of the anchor implant. Proper positioning requires rotational control because of the C-shaped coaptive margin of the native valve and the D-shaped annulus of native valve. Proper positioning of an anchor may also be facilitated by proper centering of the anchor structure prior to engagement and interface with the native valve.

Thus, it is contemplated that a loop like structure can be employed to assist centering the system within the native annulus. Additionally, a loop with an axially directed bent V like structure can be used to facilitate rotational orientation of the system if the limbs of the V project forward toward the commissures along the coaptive margin. The expression diameter (distance from center line) of the loops can both be controlled with coaxial, but separate distal and proximal control of the loop structures; drawing the distal and proximal control points together expands the loop structures.

Figure 54:
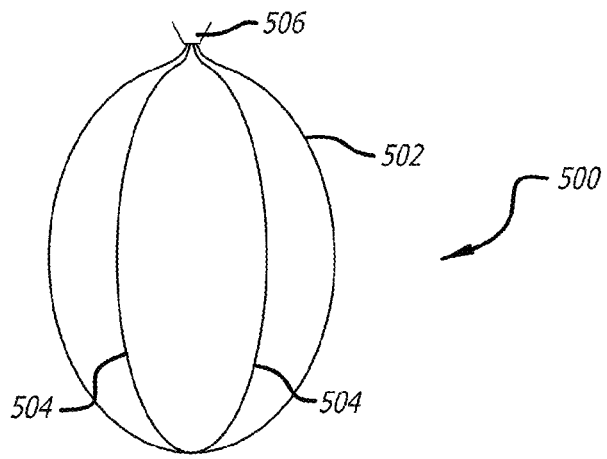
FIG. 54 is a side view, depicting positioning frame structure.
Figure 55:
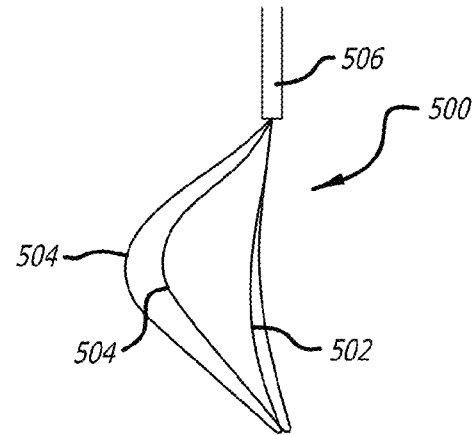
FIG. 55 is a rotated side view, depicting the positioning frame structure of FIG. 54.
Figure 56:
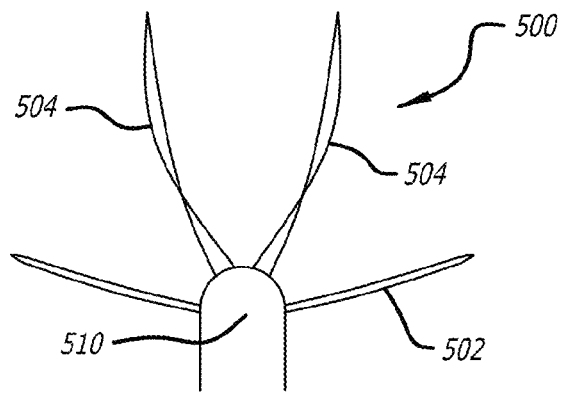
FIG. 56 is a top view, depicting the positioning frame of FIG. 54.

A combination of a simple loop and V loop structure connected together can facilitate both rotational and centering of the structure and/or anchor. Accordingly, with reference to FIGS. 54-56, there is shown one contemplated embodiment of an anchor guide tool 500. A distal end of the device forms a basket-like configuration defined by a first planar loop 502 and a pair of generally V-shaped members 504. The basket-like distal end is attached to an elongate member 506 which has a length sufficient to be remotely controlled by an operator. The device can further be inserted through a tubular sheath 510 that acts to fold and compress the distal end for advancement to the interventional site.

Figure 58:
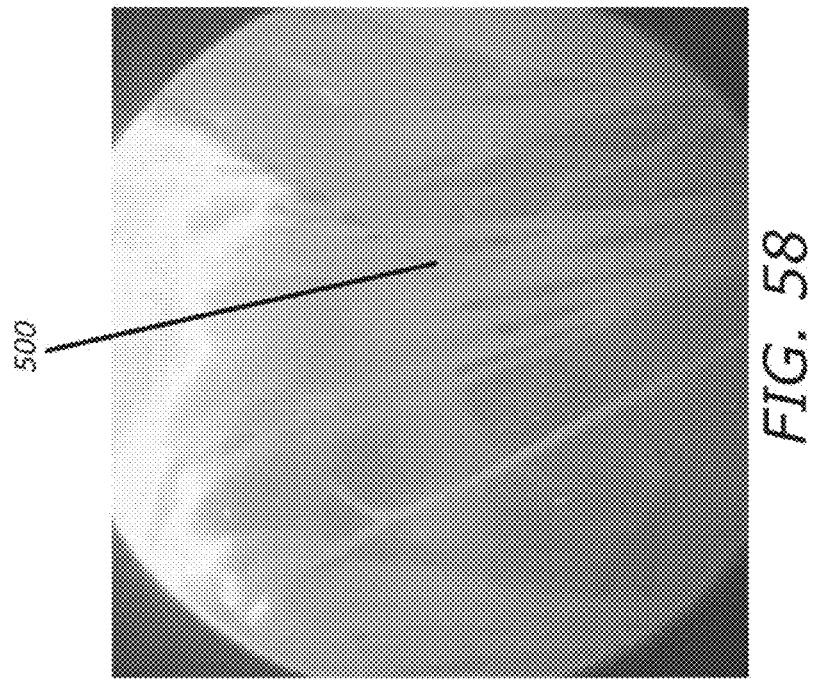
FIG. 58 is a side view, depicting further use of the positioning frame structure within anatomy.
Figure 57:
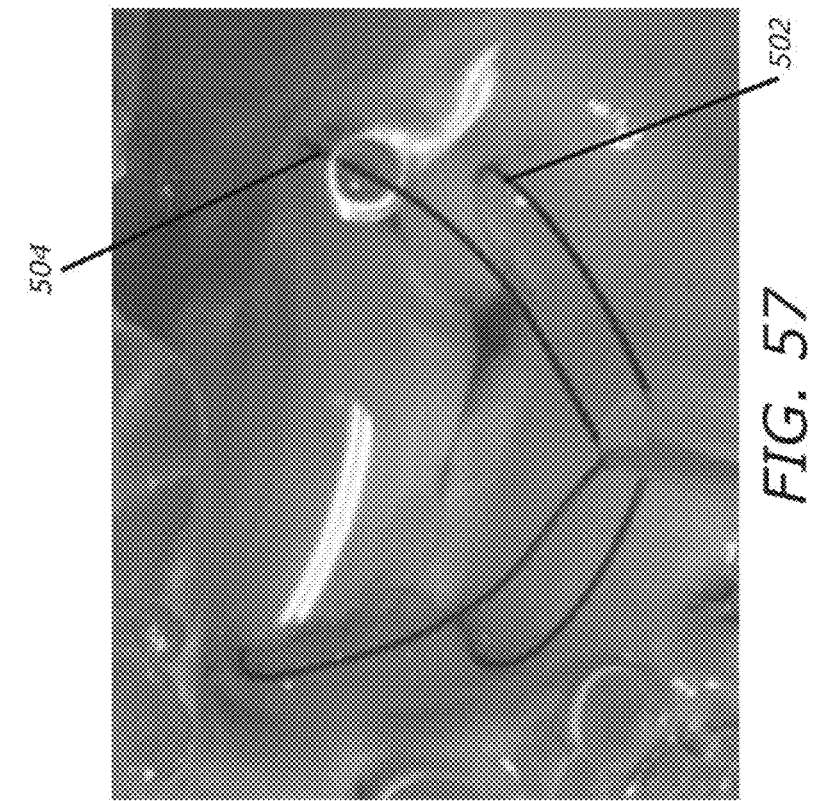
FIG. 57 is a perspective view, depicting the positioning frame structure within anatomy.

The struts defining the planar loop 502 and V-shaped member 504 can be configured to releasably engage an anchor frame (not shown). Proximal and distal connections between the struts and anchor structure can be arranged to accomplish variable express of the anchor within anatomy. In use (See FIGS. 57 and 58), the anchor guide device 500 is advanced across a mitral valve, the planar loop 502 and V-shaped members 504 being placed through the coaptation with lateral extremities configured within the anterior and posterior commissures. Once so inserted, the valve remains competent.

Figure 59:
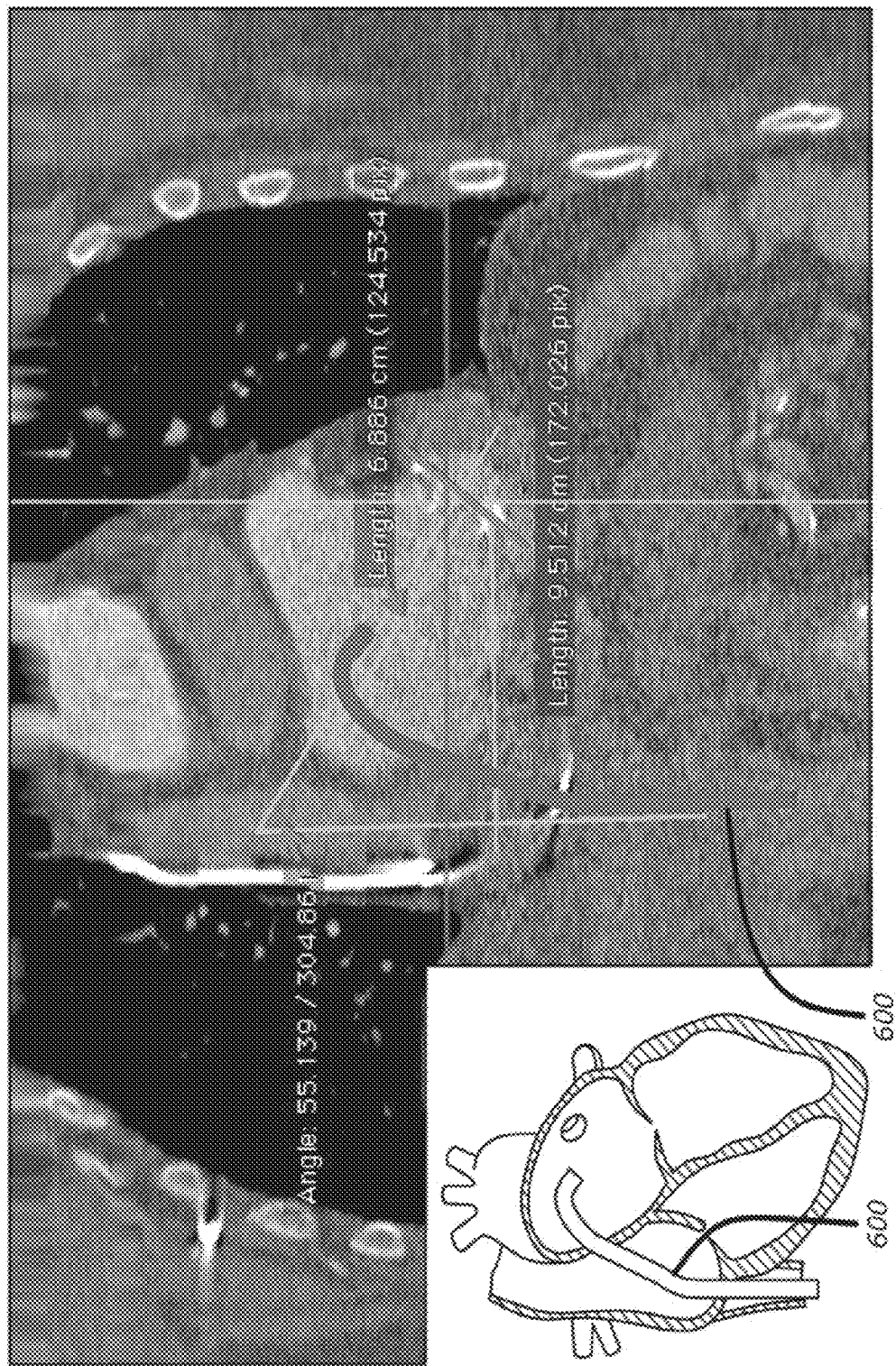
FIG. 59 is a cross-sectional view, depicting positioning of a left atrial access catheter.
Figure 60:
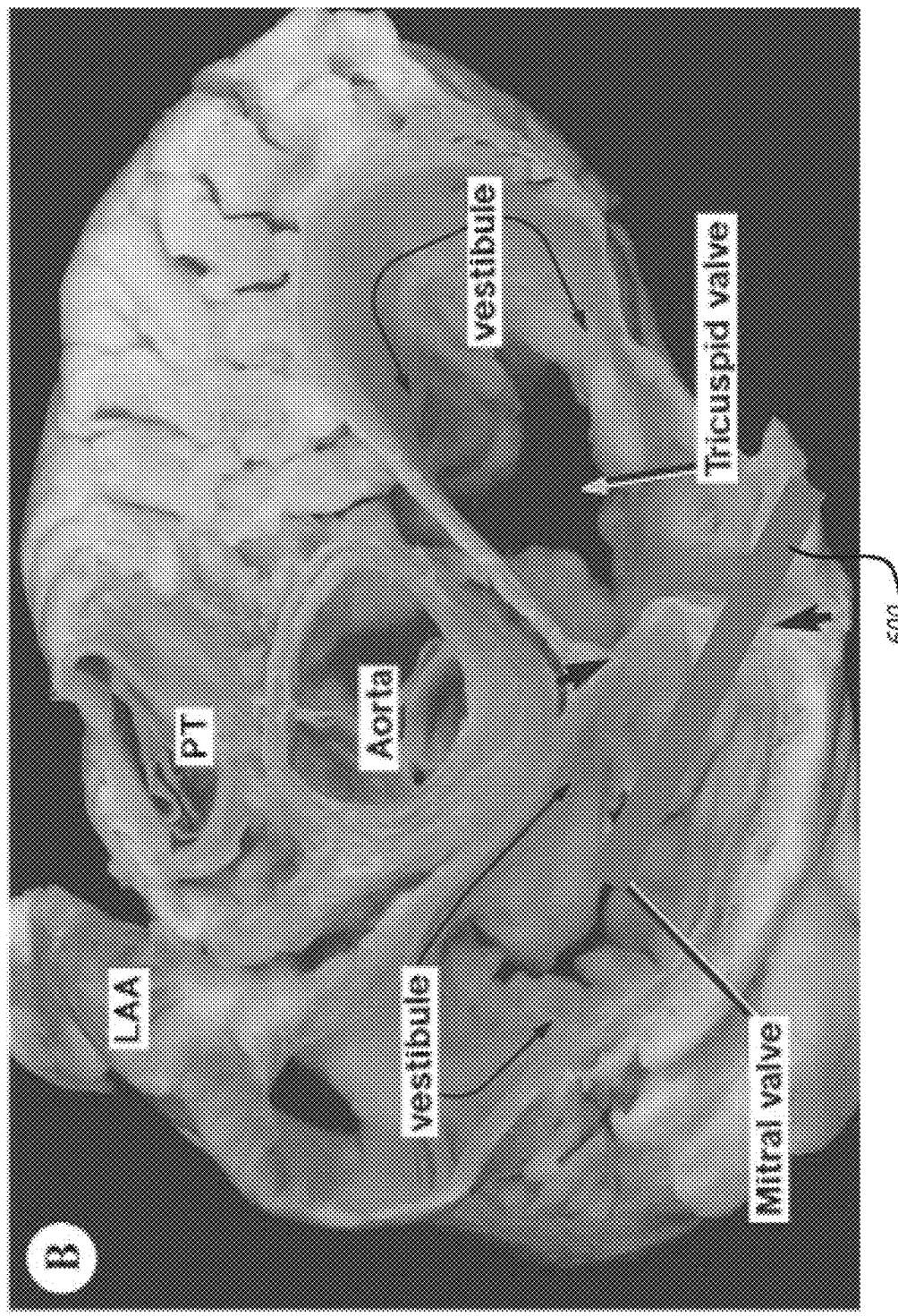
FIG. 60 is a top cross-sectional view, depicting a left atrial access catheter within anatomy.

Turning specifically now to FIGS. 59-64, one particular approach to implantation is presented. It is noted that delivery components of the anchor allow for tracking navigation through the various vasculature to the right atrium, across the inter-atrial system, and facilitating directing the anchor delivery toward the native mitral valve. FIG. 59 illustrates an atrial, deflectable access catheter 600 in position across the atrial septum and within the left atrium. FIG. 60 illustrates a top view of the atrial access catheter in position across fossa ovalis.

Figure 61:
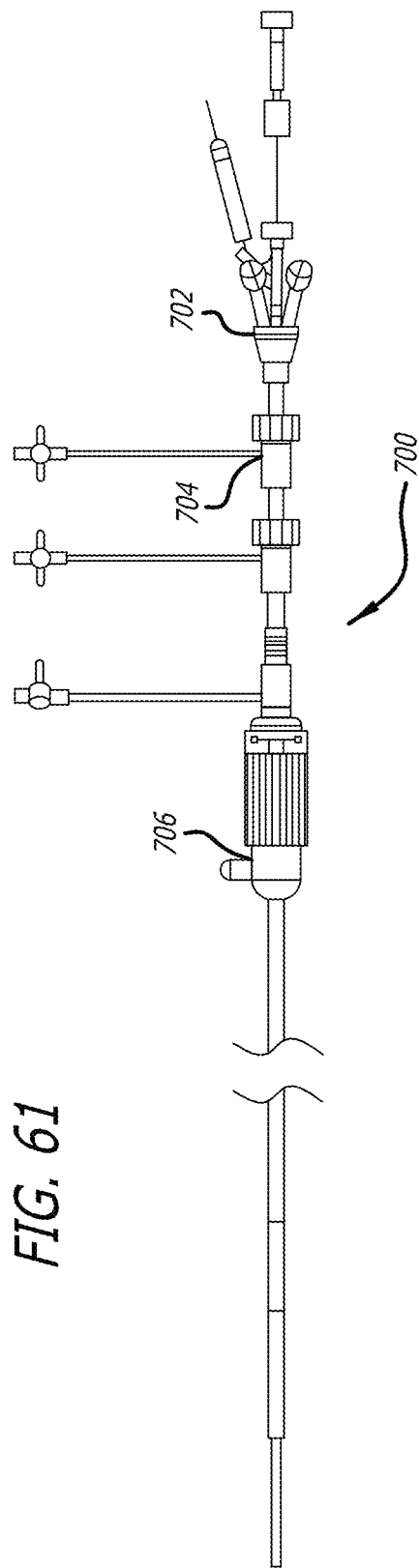
FIG. 61 is a side view, depicting one embodiment of a delivery system.
Figure 65:
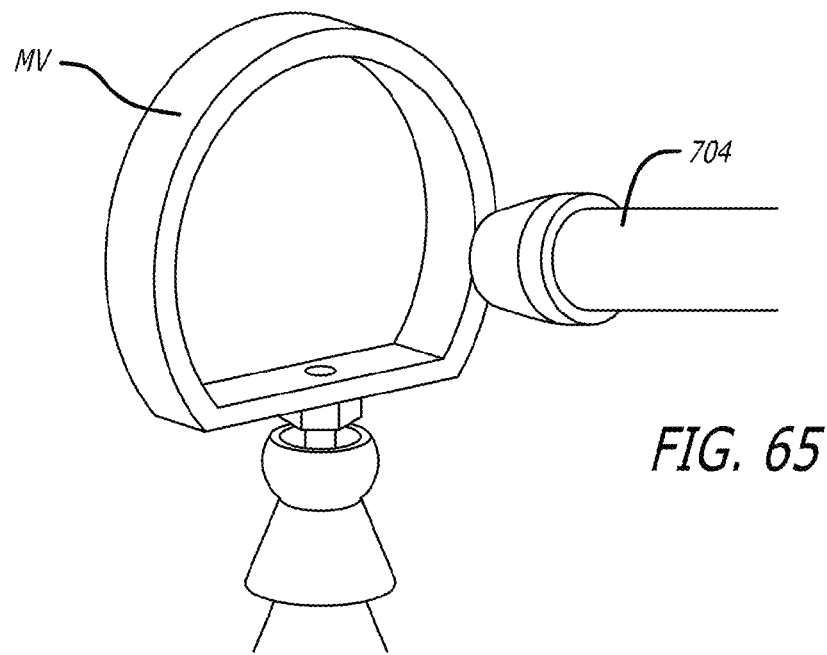
FIG. 65 is a perspective view, depicting advancing a delivery system towards a mitral valve plane.
Figure 66:
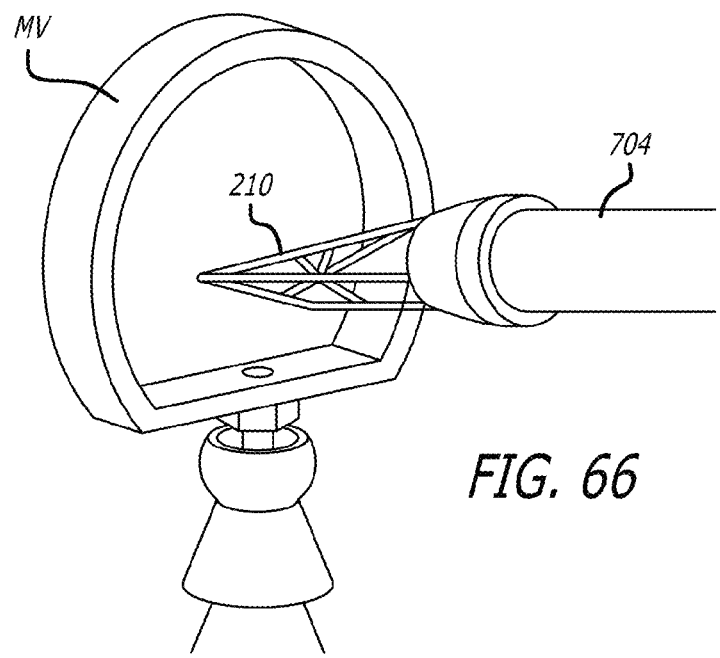
FIG. 66 is a perspective view, depicting a partially expressed anchor of a delivery system.
Figure 67:
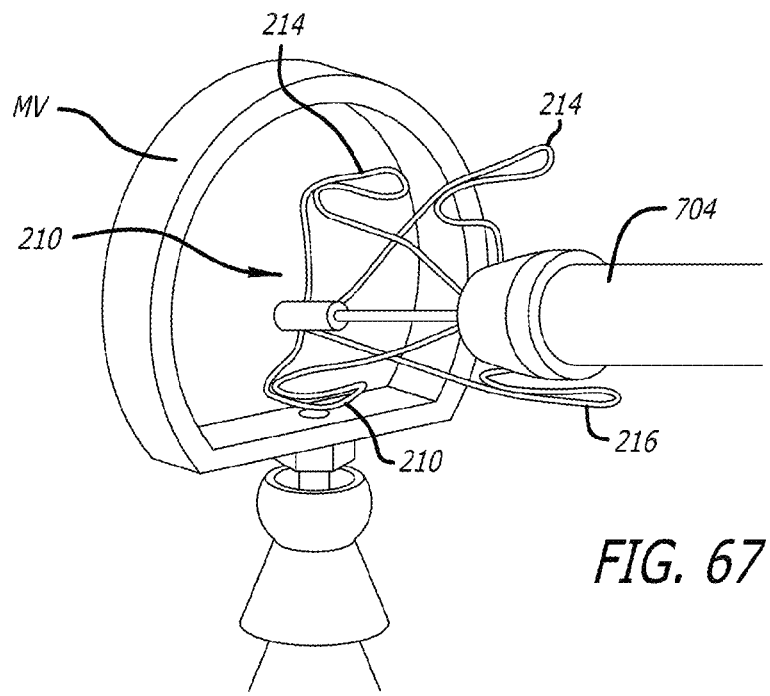
FIG. 67 is a perspective view, depicting further expression of an anchor assembly.
Figure 68:
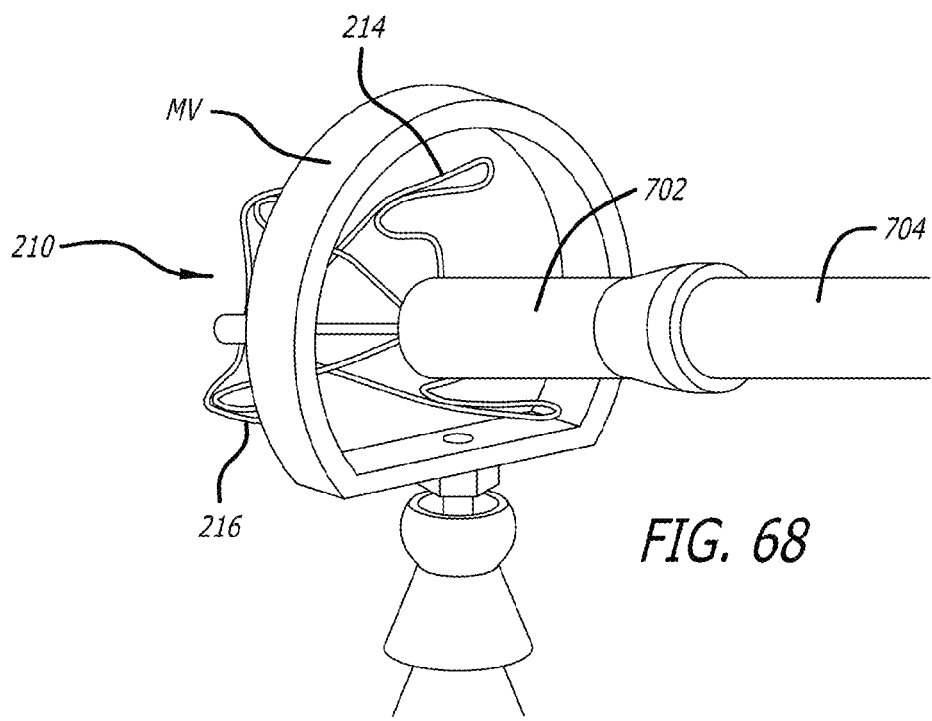
FIG. 68 is a perspective view, depicting further advancement of an anchor and delivery sheath through simulated anatomy.

Referring now to FIGS. 61-64, there is shown components of one embodiment of an anchor delivery system 700. FIG. 61 illustrates the delivery system in its assembled form where various components are coaxially arranged. An inner delivery catheter 702 is longitudinally translatable and insertable within a delivery sheath 704, which is longitudinally translatable and insertable within a deflectable sheath 706. Each component defines a generally elongate profile having a length sufficient to extend from outside a patient's body, where a manipulation end is presented to an operator, to an interventional site within a patient's body, such as extending to the mitral valve through the venous system to the right atrium, across the atrial septum and into the left atrium.

Focusing on the inner catheter 702, it includes a distal end 710 configured to releasably engage an anchor assembly (not shown). Structure such as that depicted in FIGS. 54-56 can further be employed to so releasably engage portions of the anchor. As stated, other structure such as control wires can be utilized to effect desired control and releasable connections. For example, the hoops or loops previously described as forming part of the anchor can be used for releasable connections to central wires (not shown). As such, the inner catheter is contemplated to include an inner elongate member 712 extending from the distal end 710 through an inner catheter sheath 714 to a proximal terminal end 716 of the device. The proximal terminal end 716 can include a connection for manipulation by an operator so as to cause the inner elongate member 712 to slide within the inner catheter sheath 714. At a proximal end of the inner catheter sheath can be configured a W-connector 718. The W-connector includes a central opening 719 for receiving the inner catheter elongate member 712 and a pair of angled receivers 720 adapted to accept delivery control wires or other structure. Through the ability to longitudinally translate the inner catheter elongate member 712 with respect to the inner catheter sheath 714, as well as through the use of various delivery control wires (not shown), desired manipulation of an anchor can be achieved.

The delivery sheath 704 (FIG. 63) is embodied in a tubular member extending from a proximal terminal end 722 equipped with a connector 724 having a hemostatic valve configured therein. Auxiliary access is provided to the connector 724 via a side tube 725 terminal with a conventional touhy borst or other adapter. This access may be used for flushing, aspirating, infusing contrast, etc. A distal end 726 of the sheath 704 presents a generally circular opening sized and shaped to receive an anchor assembly.

The deflectable sheath 706 (FIG. 62) also embodies an elongate tubular member including a distal portion 730 and a proximal portion 732. The tubular structure is of course large enough to receive the tubular structure of the delivery sheath, the terminal end presenting a generally circular opening. The proximal end 734 can be equipped with a connector 736 also including a hemostatic valve and a side tube 737 including a touhy borst or other adapter providing access to the valve. The proximal portion is also contemplated to include a control knob 740 configured to accomplish through conventional methods the deflection of the distal portion 730 of the deflectable sheath 706. In this regard, the control knob can function to reel in or pay out wires extending within the deflectable sheath and connected thereto at various points to cause a turning of the sheath to various degrees and angles, and at one or multiple locations. The tubular body of the sheath is thus contemplated to be axially flexible, as are the members defining the inner delivery catheter and delivery sheath. In this way, as the deflectable sheath 706 is turned, or curved, the delivery catheter and delivery sheath follow without kinking.

The deflectable sheath is contemplated to deflect into a curve adapted for entering a left atrium and secondarily, to be directed to the valve (back down at valve and then up out of plane as will be further described below). Further, various combinations of catheter deflections are contemplated. There can be a single catheter with bi-directional capability, that is a primary bend at inter-atrial septum and a distal secondary bend, as well as a proximal secondary bend (right atrial bend region). Moreover, in a dual approach, there can be an inner secondary curve ability. One key to the system is to prevent rotation of an inner deflectable vs. an outer during secondary bending.

Expression of the anchor refers to its release from a collapsed state into an expanded shape for engagement and deployment into the native valve. Due to the limited working space to express the anchor above the native valve, designs that allow for radial expansion during expression provide advantages. Additionally, component structures that provide preferential bending or folding points or planes during compression and then expansion also provide advantages, such as ribbon like elements within the anchor design or strain relief eyelets/loops within the frame.

Figure 69:
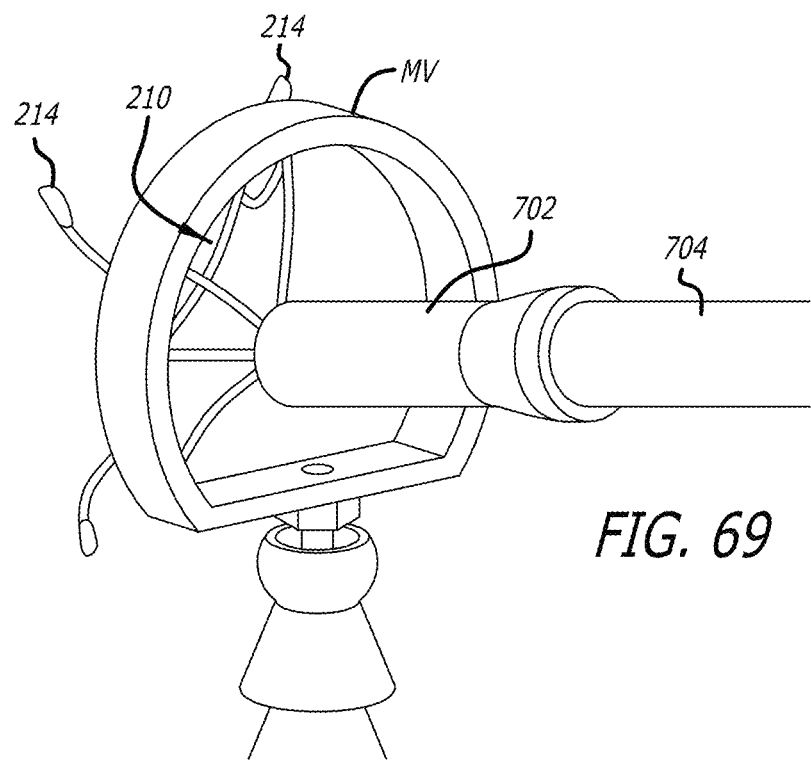
FIG. 69 is a perspective view, depicting yet further expression of an anchor within simulated anatomy.
Figure 70:
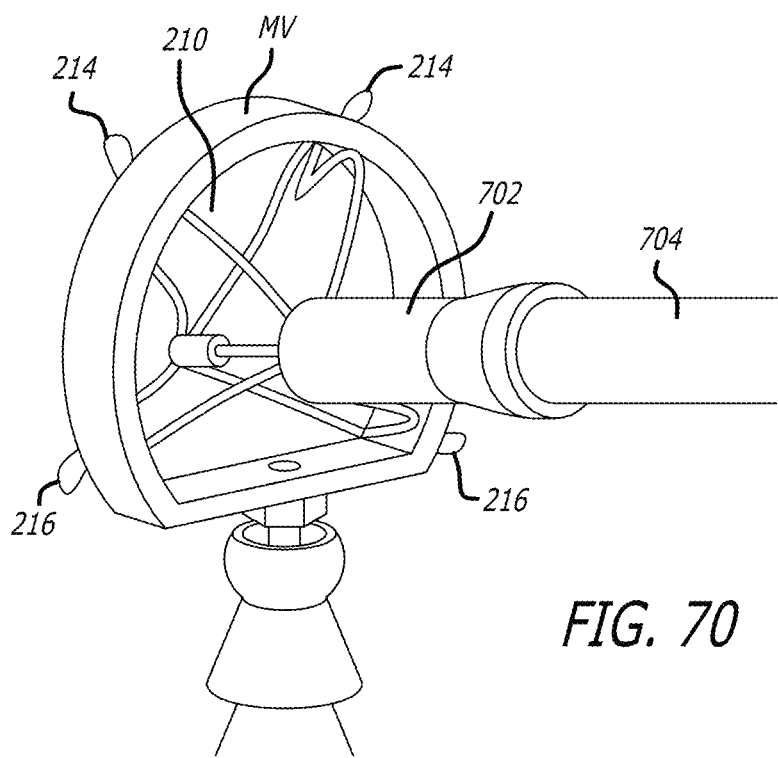
FIG. 70 is a perspective view, depicting placement of anchor structure within simulated anatomy.

With reference to FIGS. 65-71, the technique of expression of an anchor can be accomplished by advancement of the distal section of the anchor 200 (shown as the frame 210 in the FIGS.) out of the delivery sheath 704 until the distal tip (holding point) becomes proximate the native valve mitral valve plane. Note that curved deflectable catheter is not shown in these figures. The anchor 210 may first be only partially expressed, as in FIG. 67, by relative movement of the components of the inner catheter 702. The degree of expression (extent feet 214, 216 extend out from center point) can be controlled via the advance distance of inner coaxial pusher element of the inner assembly catheter. Next, the anchor and inner catheter are advanced across the mitral valve into the ventricle. The anchor 210 can then be rotated into correct alignment with the commissures via the torqueable inner member (using previously determined image plan as guidance). The anchor 210 may then be fully expressed in the ventricle, as shown in FIG. 69, then retracted to position the feet into the gutter region under the valve leaflets. Release of the proximal anchor controls allows for the visor or apron elements of the anchor to provide supra-annular holding. Once the anchor 210 is fully expressed, additional proximal controls can be used to make the anchor feet 214, 216 coplanar with the native valve mitral valve, or the pre-formed shape of the feet may be suitable as a final deployed configuration for anchoring in the valve anatomy.

Figure 71:
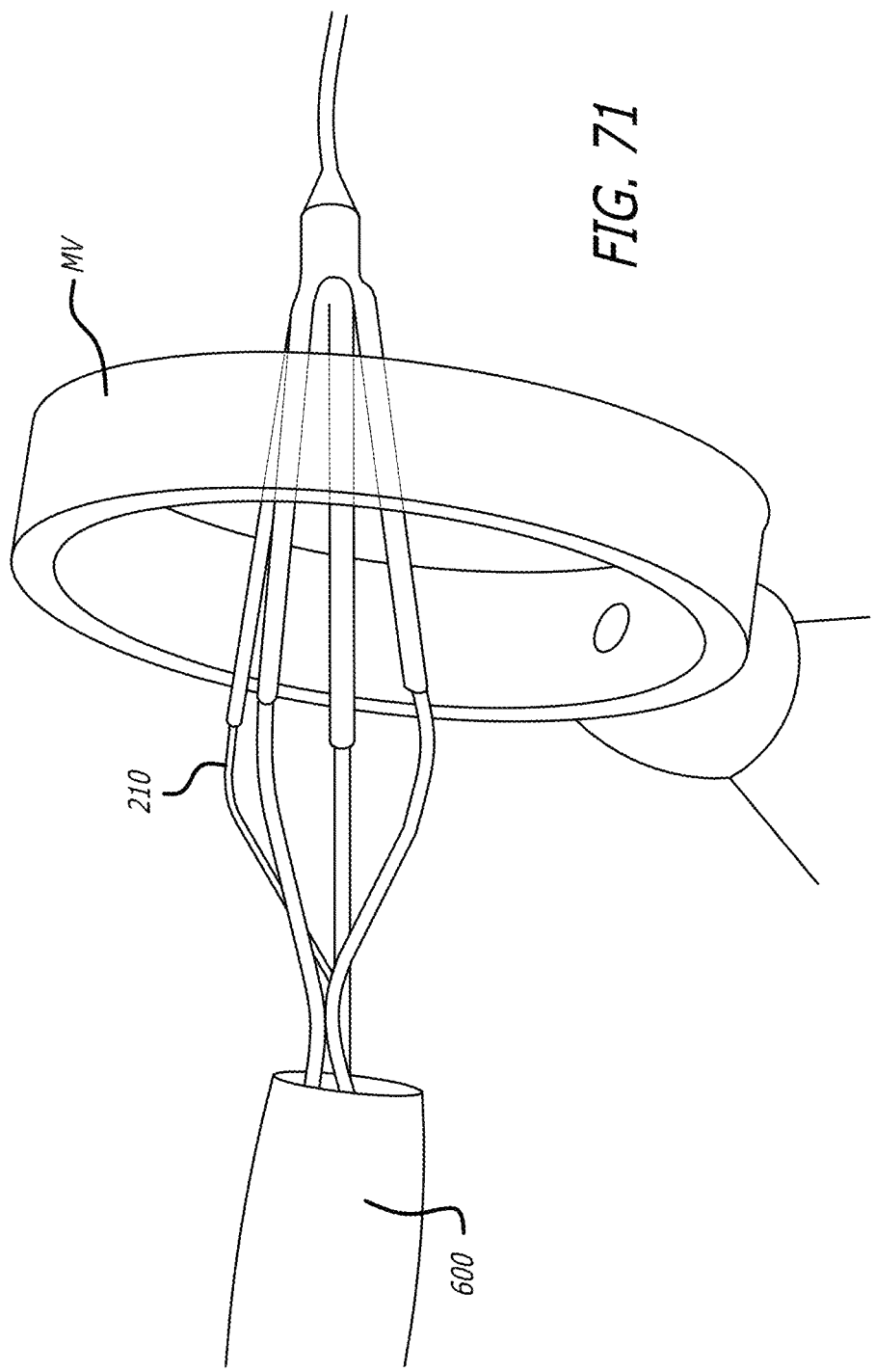
FIG. 71 is a side view, depicting recapturing an anchor assembly.

As shown in FIG. 71, recapture of the anchor assembly 210 via collapse of anchor via proximal and distal hold elongation with inversion of each individual foot is possible (here shown with use of optimal deflectable catheter 600). In this way, the anchor can be repositioned as needed prior to final implantation.

Figure 72:
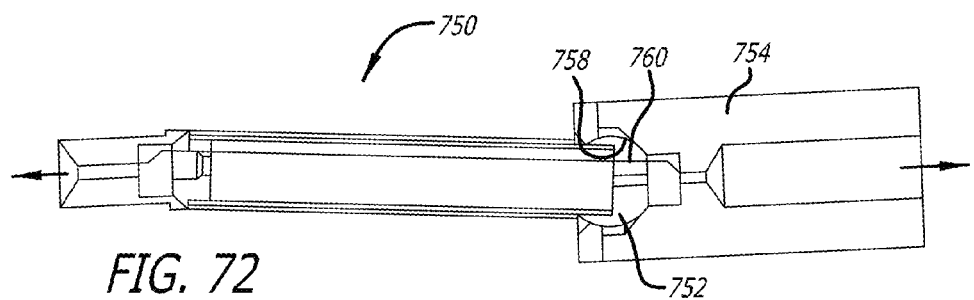
FIG. 72 is a side view partially in cross-section, depicting one embodiment of a valve delivery catheter.
Figure 73:
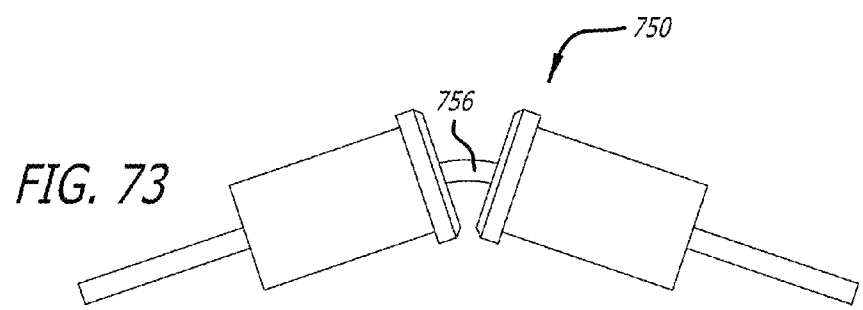
FIG. 73 is a side view depicting one approach to an articulation of a delivery catheter.
Figure 74:
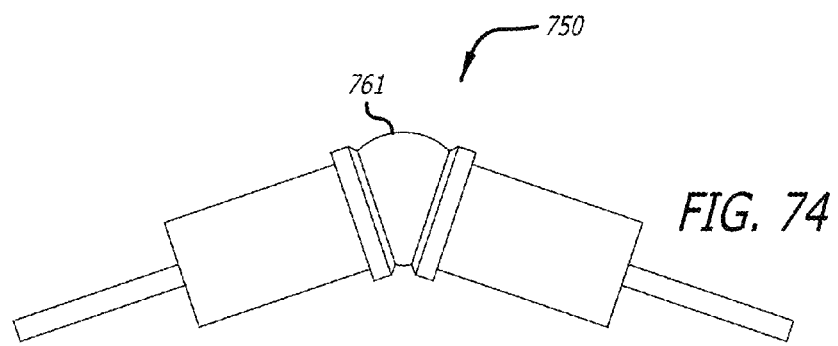
FIG. 74 is a side view, depicting another approach to an articulating portion of a catheter.

To facilitate the correct placement of the valve with respect to the anchor, it may be desirable that the angular orientation of the valve be adjusted without substantial translation of the valve. This may be accomplished by providing a valve delivery catheter 750 with an articulating joint or gimbal 752 proximate a valve capsule 754 (See FIGS. 72-74). It has been found that such a joint allows the instant center of rotation of the valve capsule 754 to be close to the valve capsule 754, thereby reducing the amount of translation of the valve during deflection.

Considering now the trajectory of a valve delivery catheter assembly 750, it can be seen that this joint 752 placement may also provide for a radius of curvature of less than 1 inch. The radius of curvature also may be less than about ½ inch, or, the radius of curvature may be less than 0.25 inch.

The flexible or articulating joint or gimbal 752 may be constructed by providing a proximal section and a distal section of the catheter assembly 750 connected by a flexible connecting component. The flexible connecting component may be comprised of a flexible shaft 756. The flexible shaft may be constructed from the following materials or elements: nitinol tubing, nitinol wire, braided polymer shaft, coil reinforced polymer shaft, elastomeric polymers, slotted metal tubing, etc. These elements may be combined to provide the desired column strength and flexural stiffness.

The joint or gimbal 752 may be provided with additional column strength by providing a bearing surface 758 between the proximal and distal components. This bearing surface may be spherical, cylindrical or other curved surface. It is preferred that the surfaces have continuous curvature to provide smooth operation in the desired direction. For example, a spherical bearing surface may enable articulation in a number of different directions, while a cylindrical surface may limit deflection to a plane perpendicular to the cylindrical surface. It can be seen that if the bearing surface forms a complete sphere, the center of rotation of the proximal and distal components will be at the center of the sphere. In some cases it may be desirable for the length of the joint to be smaller than the diameter of the spherical bearing surfaces. In this case, the bearing surface can be truncated such as in the case of a spherical cap or dome. This enables both the length and diameter of the joint to be reduced.

The joint or gimbal 752 may further include a center lumen or guidewire lumen 760. In this case it is desirable that the curvature of the center lumen be minimized to improve guide wire movement and prevent kinking. It can be seen that shaft curvature is minimized for given angular deflection and arc length when the curvature is constant along the arc. It has been found that for the joint design of FIG. 73, this can be accomplished by allowing the instant center of rotation of the proximal and/or distal components to change as the joint is deflected. In contrast, the bearing surfaces 761 of the joint shown in FIG. 74 constrain the location of the center of rotation. In the case of spherical or cylindrical bearing surfaces, it has been found that this may cause the center lumen to assume an undesirable non-uniform curvature. In this case it may be advantageous not to affix the center lumen to the bearing surfaces but to allow them to move to permit a more gradual curvature. Alternatively, the free length of the center lumen and the curvature of the bearing surfaces may be chosen to reduce the curvature of the center lumen.

Figure 75:
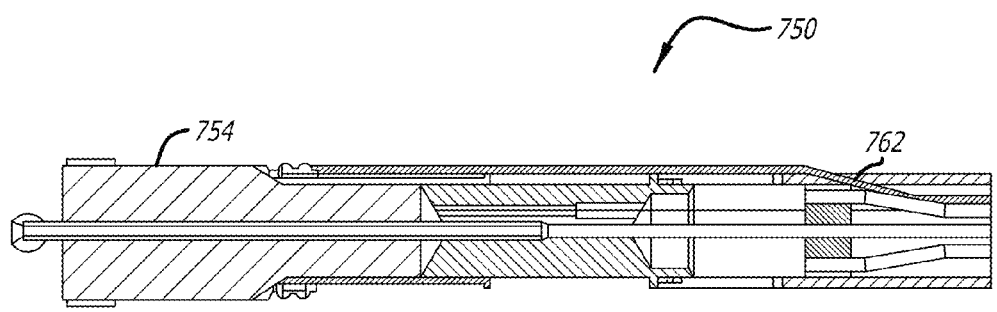
FIG. 75 is a side view partially in cross-section, depicting a distal portion of a valve delivery catheter.
Figure 76:
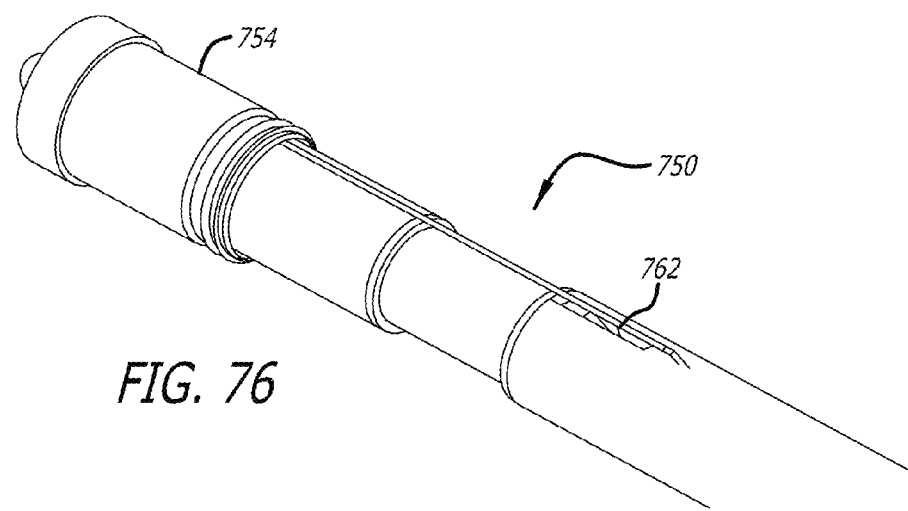
FIG. 76 is a perspective view of a distal end of a delivery catheter.

In some cases, it may be desirable for the joint to deflect or articulate freely under loads applied to the catheter or valve capsule. In other cases, it may be advantageous to actuate the deflection be external means. In these embodiments, deflection may be accomplished by means of actuators connecting the proximal and distal components at at least one location away from the centerline of the joint. These actuators may be comprised of wires, tubes, yarns, cables, or threads, herein called wires 762 (See FIGS. 75-76). In one embodiment, tension applied to a single wire causes deflection in that direction. In another embodiment, two wires acting in opposition to each other cause deflection and straightening in one direction in a plane. In still a further embodiment, three or more non-co planar wires enable deflection in a plurality of planes or directions. Moreover, a plurality of non-coplanar wires enables deflection in substantially any direction. In yet another embodiment, a plurality of wires acting in both a tensile and compressive direction provides both deflection and axial compression resistance.

Control of the actuating wires can be accomplished by means of knobs and levers. It has been found that the effective length of actuators passing through a catheter may be affected by deflection of the catheter, resulting in potentially undesirable actuation effects. This effect can be mitigated by providing actuator guide lumens with proximal and distal ends, said ends fixed relative to proximal and distal actuator effectors. These actuator guide lumens are allowed to move within the catheter shaft in regions between the proximal and distal ends so as to compensate for flexure of the catheter. In one embodiment, the actuation effectors are constructed so that deflection of an actuator on one end of the catheter results in an opposite deflection at the other end of said catheter. The magnitudes of said deflections may be scaled to compensate for stretching or deformation of catheter components under actuation stresses. It can be seen that multiple bends by be controlled by attaching the actuators in series with each other. The control mechanism may be locked in place by tightening a collar against the proximal bearing surface.

In order to maintain control of the valve during deployment it may be desirable to provide a rigid coupling segment across the interface between valve and catheter at the proximal end of the valve delivery capsule. It is further advantageous to minimize the overall length of the stiff section of the valve capsule. To this end, the sheath is constructed as a telescoping assembly where the comparatively stiff proximal section of the valve capsule bridging the proximal valve interface is kept short and a landing zone is provided for the telescoping valve segments. In one embodiment, the telescoping valve segments are provided with flanges that interact with each other to ensure that segments pull back in the proper manner. In a preferred embodiment, the actuator wires attach to the distal capsule 754. The distal capsule under influence of the actuator wires slides back over the proximal capsule. The distal capsule is provided with a flange that engages a corresponding flange on the proximal capsule, thereby causing in to retract in turn. It can be seen that this can be extended to any number of sections in order to further shorten the length of each individual section and the required length of landing zone. In some embodiments, some of the capsule sections are rigid, where others are flexible. Flexible capsule segments may be configured so as to pass over the landing zone and follow the curve of the catheter. In some embodiments, flanges are provided to limit the extension of the capsule segments. This facilitates loading of the valve into the capsule and prevents inadvertent detachment of the capsule.

Figure 77:
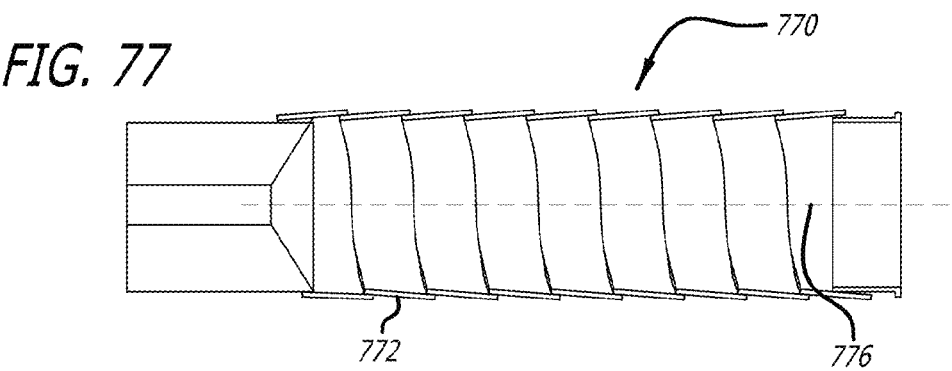
FIG. 77 is a side view depicting a helical structure of a delivery catheter.
Figure 78A:
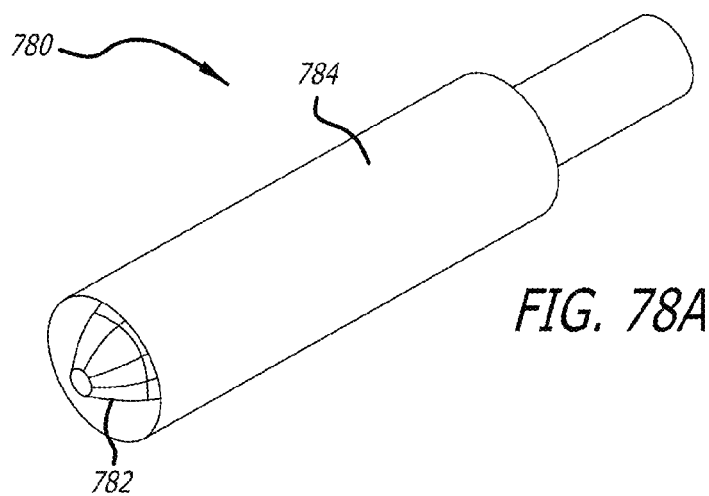
FIG. 78A-F are various views, depicting a distal portion of a valve delivery catheter.
Figure 78B:
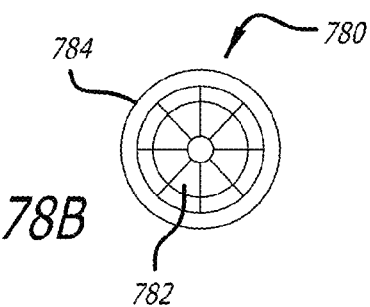
Figure 78C:
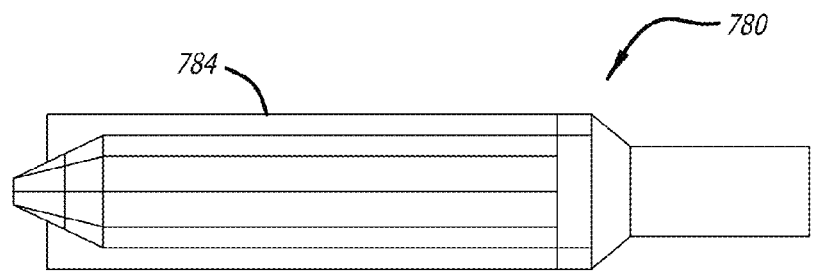
Figure 78D:
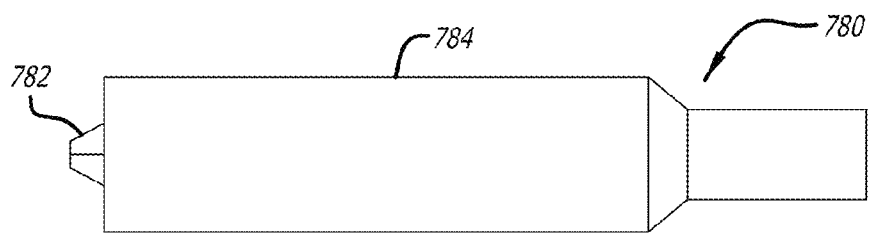
Figure 78E:
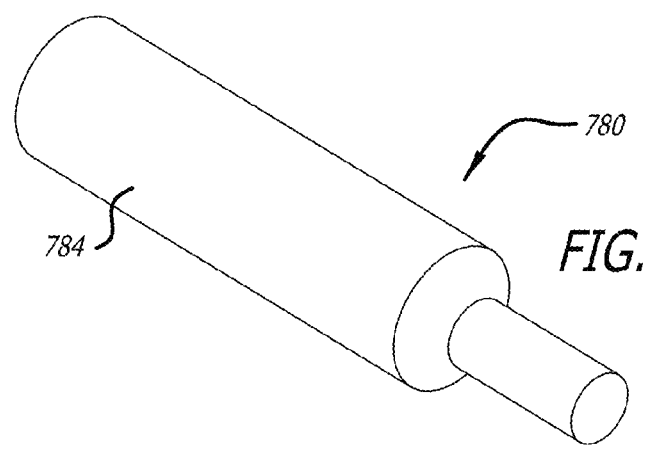
Figure 78F:
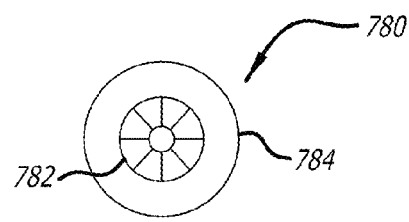

In another embodiment, the capsule 770 is constructed in a helical manner (See FIG. 77), with substantially cylindrical sections at the proximal and distal end of the capsule to facilitate loading, actuation and attachment. In some of these embodiments, the helical sleeve 772 is provided with a flange. In some embodiments, the helical sleeve elements are substantially parallel to the axis 776 of the catheter but form a stepped conical structure of decreasing diameter. In other embodiments, the helical sleeve 772 elements are inclined with respect to the catheter axis 776 but maintain a substantially constant diameter along the length of the capsule 770.

It has been found that for controlled valve deployment it is advantageous for the valve capsule 780 to resist deformation in radial, axial and circumferential directions but to retain sufficient flexibility to follow the curve of the catheter during capsule pullback and to provide a lubricious inner surface to reduce frictional resistance during valve deployment (See FIGS. 78A-F). A structure comprising a plurality of concentric layers has been developed that provides these properties. In one embodiment, an inner layer of substantially axially oriented strips 782 of PTFE is surrounded with an outer layer of circumferentially reinforced elastomeric tubing 784. The axial strips 782 are able to move with respect to each other to reduce peak strain. The axial strips 782 are constrained from expanding by the outer layer of tubing 784. The elastomeric material properties provide sufficient flexibility to prevent kinking and the circumferential reinforcement resists expansion. The reinforcement material may be in the form of a coil or braid or rings. Materials may include stainless steel, elgiloy mp35N Tungsten, Kevlar, aramid, Liquid crystal polymer, glass or ceramic fibers, filaments or yarn. In some embodiments the axial strips maybe bent inwards at the distal end to provide a smoother transition.

In some cases, after complete or partial deployment of the valve it is desired to remove or reposition the valve by retracting in completely or partially into a catheter. Such retraction requires overcoming substantial outward expansion force of the valve. It has been found that this is facilitated by providing a gradual tapered transition to guide the expanded valve into a smaller retrieval tube (See FIG. 79). In some embodiments, this transition is provided by an expandable funnel component 790. In some embodiments, this device is integral with the delivery catheter. In other embodiments, the funnel 790 may be part of a separate retrieval device. In still other embodiments, the funnel 790 may be part of a deflectable sheath component. In all cases, it is contemplated that the funnel can exhibit high axial and radial stiffness in its expanded configuration, while collapsing to a comparatively smaller diameter for delivery and retrieval.

In one embodiment, the expandable funnel 790 is comprised of a plurality of petal-like structures 792. These structures are configured to slide over each other to expand from a generally cylindrical configuration to a generally conical configuration. The individual petals 792 may be keyed to each other or constrained by another component to limit radial expansion. In some embodiments, slots are provided at the transition from a cylindrical to a conical geometry to reduce stress. The petal materials may be materials such as polyimide, Nitinol, high density polyethylene, Teflon or FEP. Moreover, they may be reinforced or they may be constrained on the outside be a braid. The funnel 790 may be released by continued pullback or the valve capsule or it may be advanced out of the valve delivery catheter after valve delivery.

In another embodiment, the funnel 790 is formed by a braid that is invaginated onto itself forming a conical distal chamber. The dimensions of such a braid are selected to provide both axial and radial stiffness in the expanded configuration. The braid angle and pic count maybe varied along the length of the braid.

Next addressed are general requirements for delivering a replacement mitral valve via a trans-septal approach, into a previously placed anchor. It is desirable that the valve be collapsed/compressed and encapsulated in some manner to navigate the venous system to the right atrium and to cross the inter-atrial septum and engage the native valve and the anchor ring in the disclosed embodiment. Also, given the relative stiffness of the collapsed valve assembly in this region, there may be a need for a flexible or possibly articulating segment proximal and possibly distal of the encapsulated valve region of the delivery system to aid with tracking. Further, the delivery system should be able to navigate a primary curve in the right atrium and trans-septal region of the anatomy. The system can then be able to navigate a secondary curve from the septum back toward the mitral valve, which may be out of plane relative the primary curve. The encapsulated valve can then also be able to be controllably expressed out of the catheter. In general, this can be accomplished via an advancement of the valve out of the catheter or via a pullback of an encapsulating sheath. The former requires significant adjustment and anticipation of final valve position as it is expressed. Unsheathing allows the valve to be in relative axial position prior to expression into the anchor structure. It may also be desirable during valve delivery to be able to reposition prior to full expression and deployment, primarily axially and to recapture or retrieval of the valve for removal prior to and after full expression and deployment. Moreover, it may be desirable for the delivery system to have temporary or releasable connections or holding points to control position as the valve begins to become loaded, as well as enable retrieval. Imaging visibility on fluoro and echo to facilitate alignment and positioning relative to native valve and the anchor of the disclosed embodiment is also contemplated. The alignment and positioning of the system includes axial position, rotational orientation, planar x-y position relative to native valve plane, and the axial vector relative to the perpendicular vector of the native valve plane.

It is to be noted that the creation of a flexible or articulating region can be accomplished via flexible shaft materials and construction and can be improved or augmented with deflectable catheters. Controlled deflection can occur in multiple locations along the catheter shaft and can be done to accomplish deflection that occurs in different planes. A system with multiple coaxial catheters for a valve delivery system can have one catheter that deflects or multiple catheters that deflect to create the proper compound vectoring to the mitral valve in a trans-septal configuration. Specifically, an outer catheter may be used to create the primary curve described with an inner catheter or shaft assembly utilized to create the secondary curve.

With this in mind, we turn to FIGS. 80-83A which depict components of one particular approach to a valve delivery catheter system 800. The delivery catheter 800 is generally elongate and tubular. A distal end portion 802 includes a valve capsule 804 sized and shaped to receive a radially compressed valve assembly. A marker 808 can be configured at the distal end to provide a visual aid when using remote viewing techniques. A proximal end portion 806 terminates in a hub 808 providing access for an actuator 810 and other structure such as control wires or the like. The actuator 810 itself can include a handle 812 and a lever 814 for controllable manipulation of a control member 820. A mid-section 824 of the collection system 800 is characterized by corrugated sections.

Figure 79:
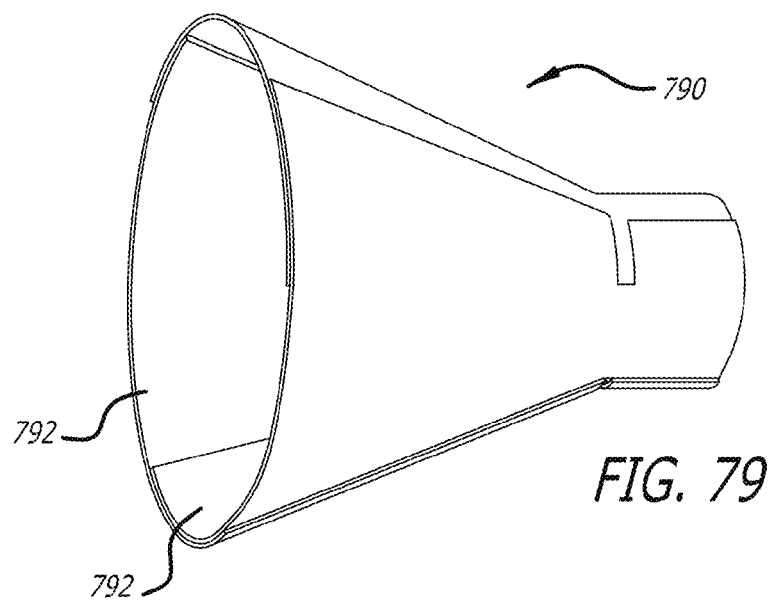
FIG. 79 is a perspective view, depicting a cone structure for incorporation into a delivery catheter.
Figure 80:
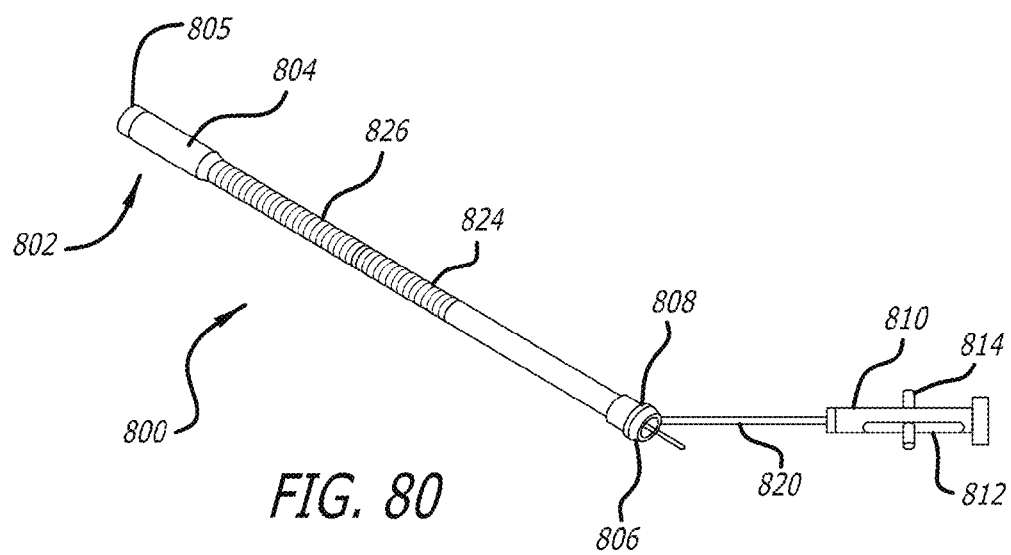
FIG. 80 is a perspective view, depicting a valve delivery sheath catheter.
Figure 81:
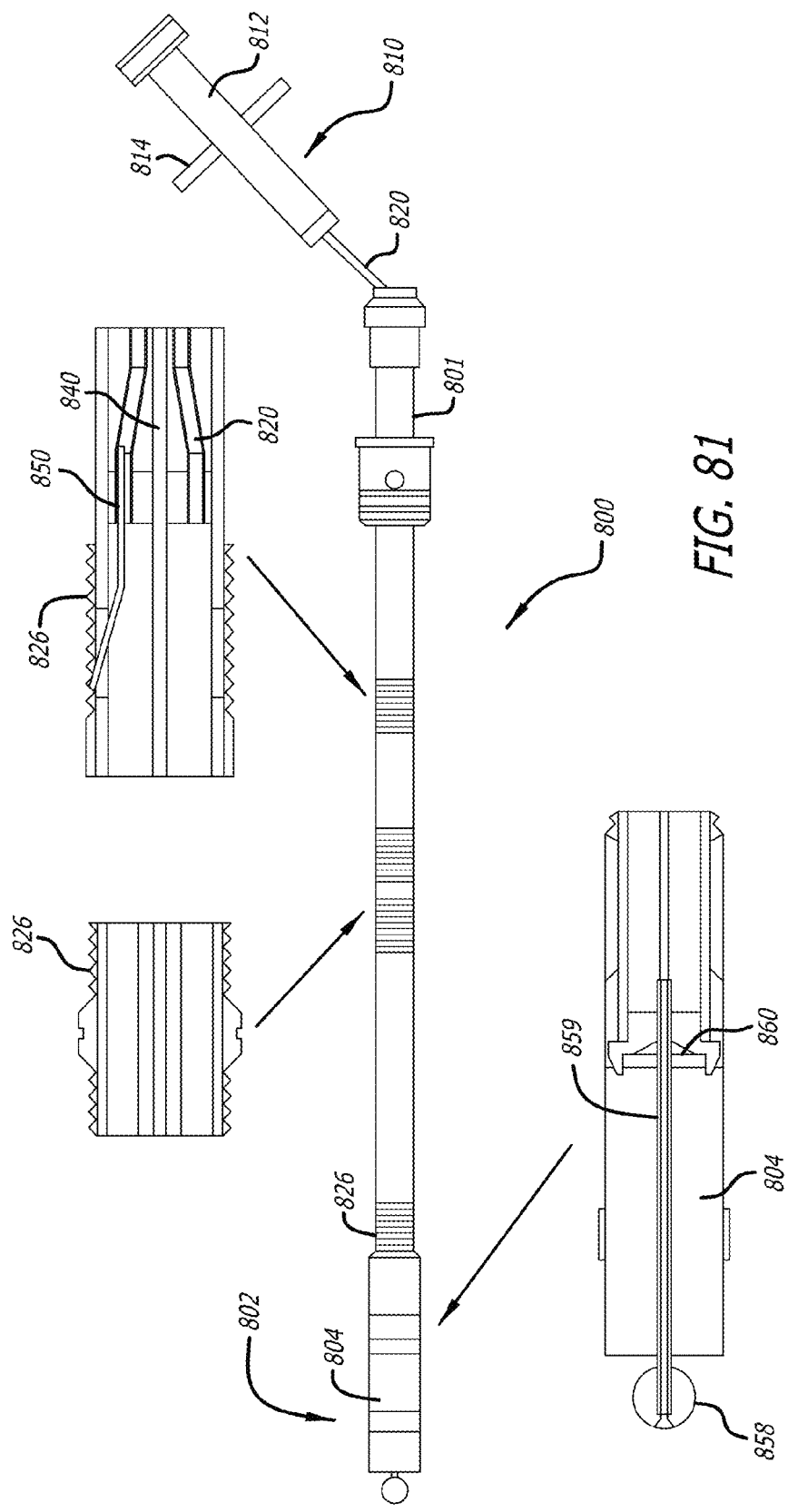
FIG. 81 is a side view with portions in cross section, depicting details of a capsule pullback mechanism.
Figure 82:
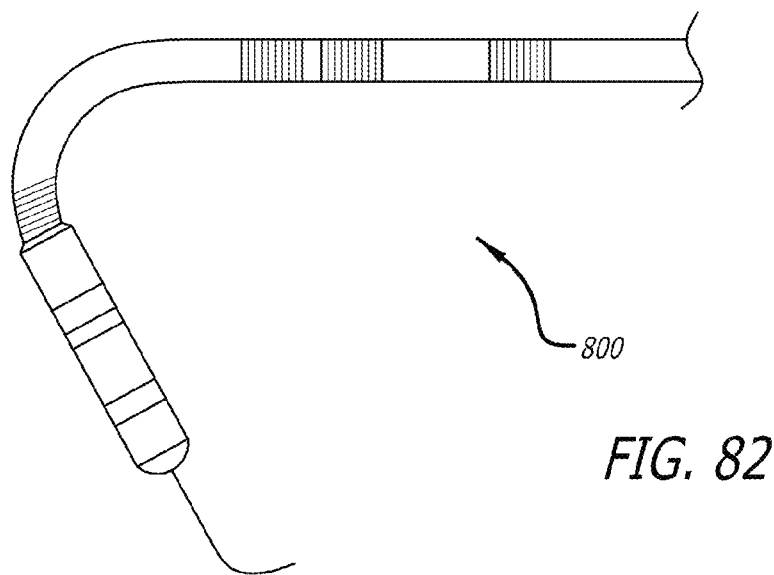
FIG. 82 is a side view, depicting the structure of FIG. 81 with a curved distal section.
Figure 83:
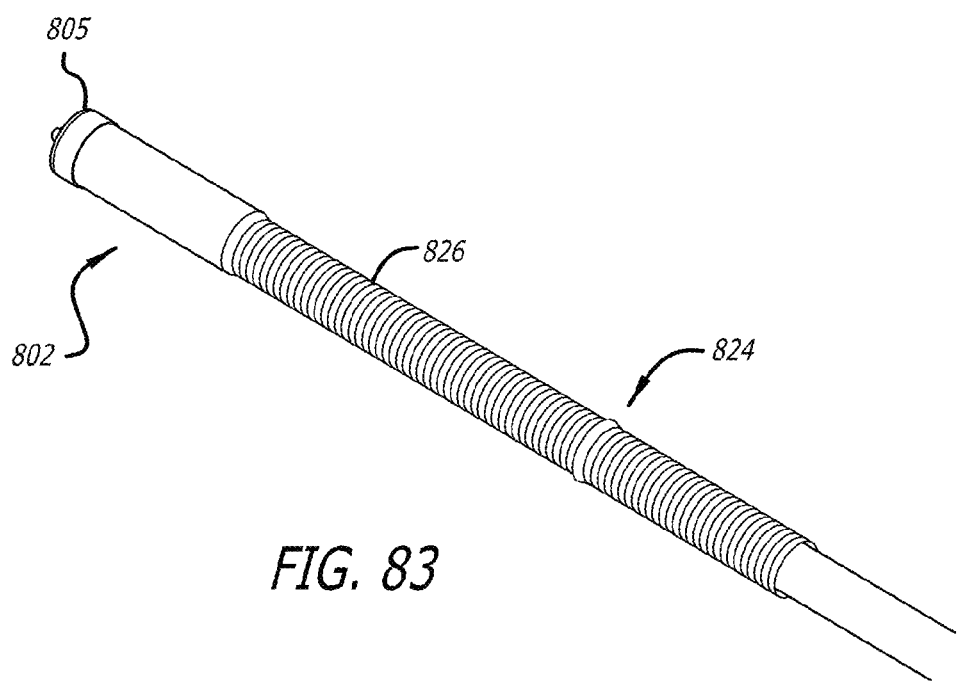
FIG. 83 is a perspective view, depicting a distal capsule and sleeve instruction.
Figure 83A:
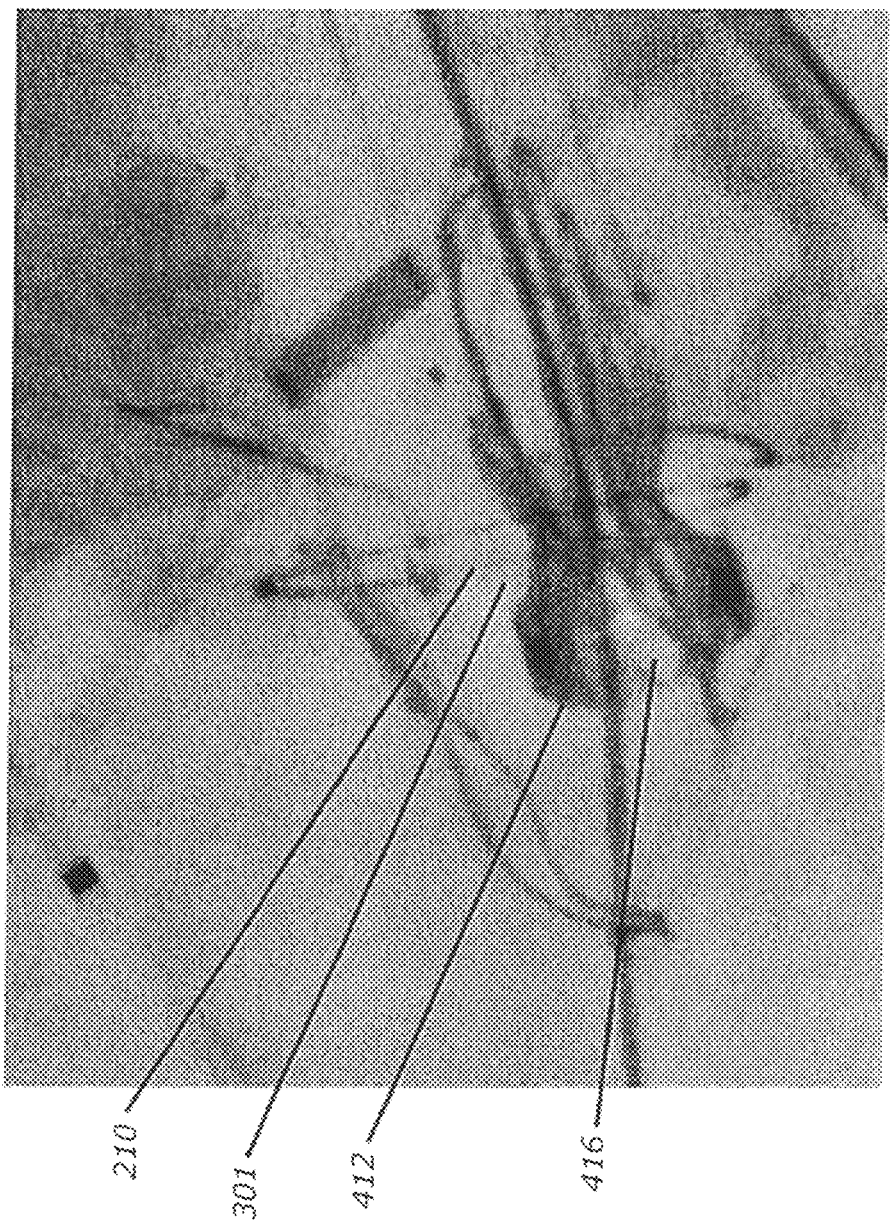
FIG. 83A is a fluoroscopic view of a valve prior to expansion into the anchor.
Figure 84:
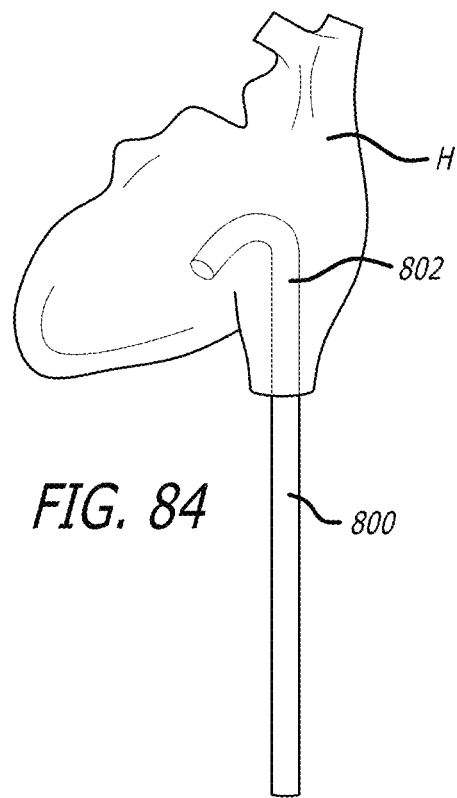
FIG. 84 is a perspective view, depicting a deflectable tip catheter structure.
Figure 85:
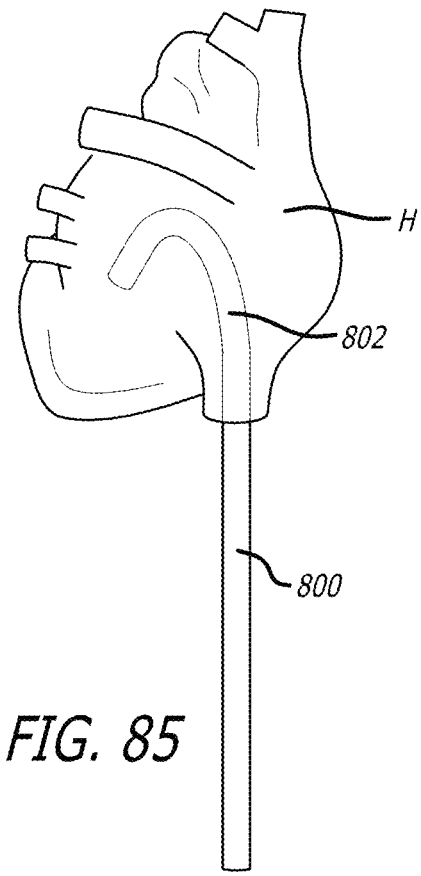
FIG. 85 is a perspective view, depicting another embodiment of a deflectable tip catheter within anatomy.
Figure 86:
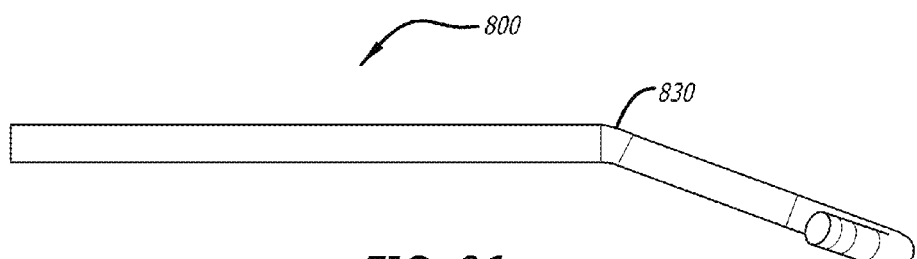
FIG. 86 is a side view, depicting a deflectable tip catheter with two deflection points.
Figure 87:
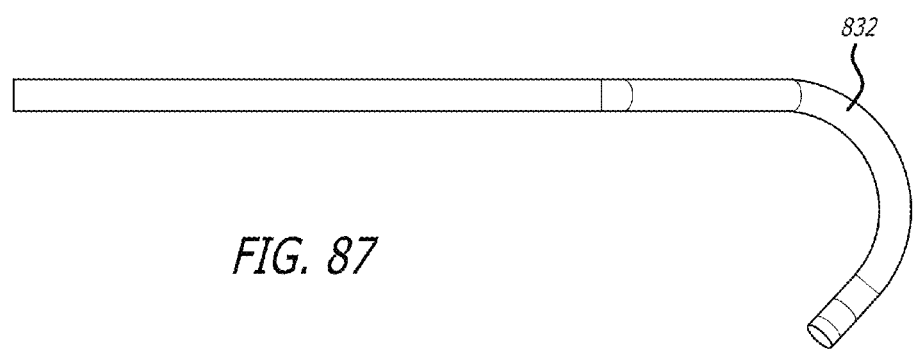
FIG. 87 is a side view, depicting a rotated view of the structure depicted in FIG. 86.
Figure 88:
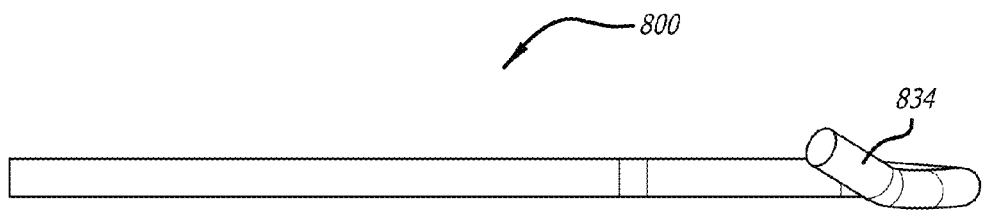
FIG. 88 is a side view, depicting another approach to a deflectable tip catheter with two deflection points.
Figure 89:
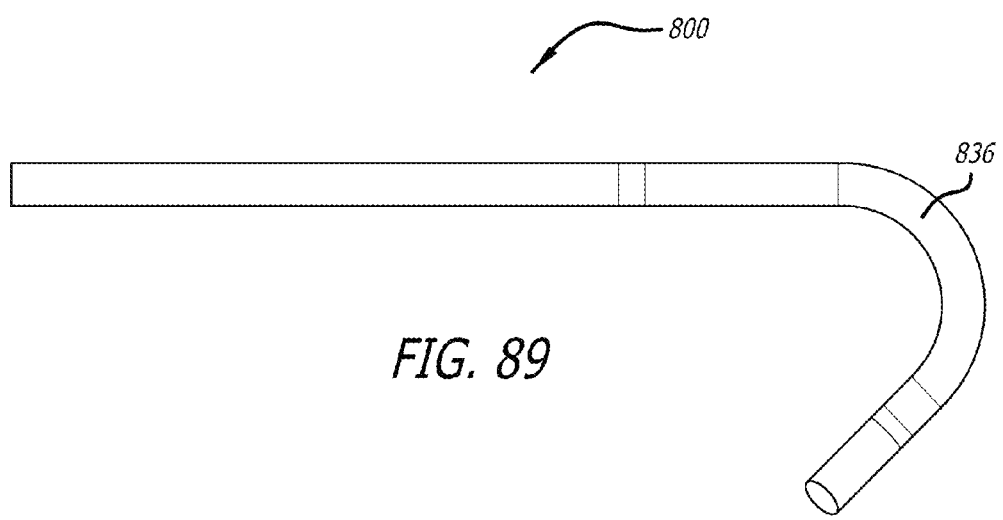
FIG. 89 is a rotated view, depicting the deflectable tip catheter of FIG. 88.

With reference to FIGS. 84-89, there are shown various angles which the anchor delivery catheter and valve delivery catheter 800 are expected to assure and traverse through anatomy. It has been found that such sharp angles can cause conventional tubular structures to buckle and collapse, thus limiting an ability to reach a target interventional site within anatomy like the heart H. The corrugated section 826 of the catheter 800 provides structure which can bend or curve without suffering from buckling or collapse. Moreover, knowing the anatomy leading to a mitral valve lends itself to providing a catheter prepared to deflect to navigate known anatomical structures. For example, the catheter 800 can be configured to include multiple deflection points. One deflection point 830 can be provided so that passage through the right atrium or IVC is possible (FIG. 78). Another deflection point 832 can permit passage through fossa ovalis (FIG. 79). In an alternative approach (See FIGS. 88-89), a deflection point 834 can direct the catheter from the left atrium to the mitral valve and another deflection point 836 can accomplish passage through the fossa ovalis. Other deflection points can also of course be incorporated to traverse other anatomy.

Returning to FIG. 81, one can appreciate control of axial bending of the valve delivery catheter 800. One or more control wires can be attached at a distal end to interior walls. Withdrawal of or otherwise placing a tension on the control wires from a proximal end of the wire will cause the portion of the corrugated section 826 to be withdrawn to express the valve. Further controls are also contemplated to permit certain patterns or certain ordering of degrees of bending or turning to thereby relieve possible reliance upon remote imaging. Regarding FIG. 75B, prior to deployment, the capsule 804 can be axially positioned and aligned with the waist section 301 centered with the anchor ring 210. While in the preferred imaging plane, the delivery catheter can also be positioned per the methods described in FIGS. 53B-53E.

Once the distal portion 802 of the valve delivery catheter system 800 is placed as desired within or proximate an anchor assembly using one or both of remote visualization and planned or adaptive articulation of the catheter, steps can be taken to eject a valve assembly from the valve capsule 804. To accomplish this, various approaches can be taken based upon a number of contemplated configurations of catheter shaft construction to enable releasable encapsulation of the replacement valve. In one approach, dual catheter construction with outer pullback is provided. Thus, a partial sheath with a pull system internalized on inner catheter can be utilized, or alternatively the delivery catheter can be equipped with a complete sheath along length. Moreover, the catheter can include a distal capsule pullback with collapse of an inside of an outer or a dual catheter with inner sheath pullback. Distal and proximal sheaths are also contemplated where a distal sheath is advanced off and a proximal is pulled off. Finally, also contemplated is a single sheath catheter pulled back off of a valve (inner assembly holds valve).

In any event, in one particular approach, a distal end of the catheter 802 can include two control features. A terminal end ball 858 can be provided to function both to retain the valve within the capsule 810 as well as present an atraumatic surface for navigating anatomy. Positioned proximally along a retainer bar 859 a length sufficient to accept a valve implant is a retaining surface 860. Thus, withdrawing the capsule 804 results in the ball 858 and retaining surface 860 maintain the longitudinal position of the valve. As the capsule is withdrawn, the valve returns to its expanded state and into engagement with the anchor. The delivery catheter is then withdrawn from the intervention site to thereby replace a mitral valve.

Further modifications and alternative embodiments will be apparent to those of ordinary skill in the art in view of the disclosure herein. For example, the systems and the methods may include additional components or steps that were omitted from the diagrams and description for clarity of operation. Moreover, those of ordinary skill in the art will appreciate that aspects and/or features disclosed with respect to one embodiment in some cases may be incorporated in other embodiments even if not specifically described with respect to such other embodiments. It is to be understood that the various embodiments shown and described herein are to be taken as exemplary, including dimensions of various components, and as such various sizes outside of identified ranges are also contemplated. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims. Accordingly, this description is to be construed as illustrative only and is for the purpose of enabling those skilled in the art the general manner of carrying out the present teachings. It is to be understood that the particular examples and embodiments set forth herein are nonlimiting, and modifications to structure, dimensions, materials, and methodologies may be made without departing from the scope of the present teachings. Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

Thus, it will be apparent from the foregoing that, while particular forms of the invention have been illustrated and described, various modifications can be made without parting from the spirit and scope of the invention.

We claim:

1. A method of replacing a mitral valve of a heart in a multiple step approach, the mitral valve including commissural clefts, an anterior leaflet, a posterior leaflet, an annulus and a sub-annular gutter, comprising:

inserting an anchor assembly within the heart, the anchor assembly including a first expandable frame movable between a compressed configuration and an expanded configuration, a retention structure, a plurality of projections, and a generally central hub of the first expandable frame positioned lower than the plurality of projections and positioned radially inward from the retention structure;

expanding the anchor assembly to the expanded configuration while positioned supra-annularly to the mitral valve;

arranging at least one of the plurality of projections so that the one projection is placed into engagement with the sub-annular gutter;

subsequent to inserting the anchor assembly and arranging the at least one of the plurality of projections of the anchor assembly, inserting an artificial valve within the heart, the artificial valve comprising a second expandable frame and valve leaflets attached to the second expandable frame, wherein the inserted anchor assembly leaves the leaflets of the mitral valve unaffected and the anchor assembly does not interrupt leaflet, chordae, or native valve function of the mitral valve until placement of the artificial valve; and arranging the artificial valve into engagement with the retention structure of the anchor assembly.

2. The method of claim 1, wherein the anchoring assembly is sized and shaped to be implanted without reshaping the annulus.

3. The method of claim 1, wherein the artificial valve is configured to sealingly engage natural tissue.

4. The method of claim 1, wherein the artificial valve is inserted within the heart using a catheter, wherein the artificial valve is self-expanded within the anchor assembly.

5. The method of claim 1, further comprising employing an orientation frame to align the plurality of projections with native anatomy.

6. The method of claim 5, wherein the orientation frame defines a part of the anchoring assembly.

7. The method of claim 5, wherein the orientation frame defines structure separate and distinct from the anchor assembly.

8. The method of claim 1, wherein said arranging the artificial valve comprises engaging a generally D-shaped outer peripheral region of the second expandable frame of the artificial valve with the retention structure of the anchor assembly while a circular valve orifice of the artificial valve is positioned radially inward from the generally D-shaped outer peripheral region and carries the valve leaflets that define a circular perimeter at the circular valve orifice.

9. The method of claim 8, wherein the first expandable frame of the anchor assembly comprises a first nitinol wire construction that is at least partially covered in a mesh material and that is movable between the compressed configuration and the expanded configuration, and wherein the second expandable frame of artificial valve comprises a second nitinol wire construction that is at least partially covered in a tissue material and that is expandable independently from the first expandable frame of the anchoring assembly.

10. The method of claim 9, wherein the plurality of projections of the anchor assembly comprise sub-annular projections that are positioned lower than the retention structure of the anchor assembly, and wherein the generally central hub is positioned lower than the sub-annular projections.

11. The method of claim 10, wherein said inserting the anchor assembly within the heart comprises inserting the anchor assembly into the left atrium via an anchor delivery catheter, and said inserting the anchor assembly within the heart comprises inserting the valve assembly into the left atrium via a valve delivery catheter after the anchor assembly engages with the sub-annular gutter of the mitral valve.

12. A method of replacing a mitral valve of a heart in a multiple step approach, the mitral valve including commissural clefts, an anterior leaflet, a posterior leaflet, an annulus and a sub-annular gutter, comprising:

inserting an anchor assembly within the heart using an anchor delivery catheter covering the anchor assembly, the anchor assembly including a first expandable frame movable between a compressed configuration and an expanded configuration, a retention structure, a plurality of projections, and a generally central hub of the first expandable frame positioned lower than the plurality of projections and positioned radially inward from the retention structure;

at least partially uncovering the anchor assembly while positioned supra-annular to the mitral valve;

arranging at least one of the plurality of projections so that the one projection is placed into engagement with the sub-annular gutter;

subsequent to inserting the anchor assembly and arranging the at least one of the plurality of projections of the anchor assembly, inserting an artificial valve within the heart, the artificial valve comprising a second expandable frame and valve leaflets attached to the second expandable frame, wherein the inserted anchor assembly leaves the leaflets of the mitral valve unaffected and the anchor assembly does not interrupt leaflet, chordae, or native valve function of the mitral valve until placement of the artificial valve; and arranging the artificial valve into engagement with the retention structure of the anchor assembly.

13. The method of claim 12, wherein the anchoring assembly is sized and shaped to be implanted without reshaping the annulus.

14. The method of claim 12, wherein the artificial valve is configured to sealingly engage natural tissue.

15. The method of claim 12, wherein the artificial valve has a sealing surface and the sealing surface is configured to engage natural leaflets.

16. The method of claim 12, wherein the artificial valve is self-expanded within the anchor assembly.

17. The method of claim 12, wherein said arranging the artificial valve comprises engaging a generally D-shaped outer peripheral region of the second expandable frame of the artificial valve with the retention structure of the anchor assembly while a circular valve orifice of the artificial valve is positioned radially inward from the generally D-shaped outer peripheral region and carries the valve leaflets that define a circular perimeter at the circular valve orifice.

18. The method of claim 17, wherein the first expandable frame of the anchor assembly comprises a first nitinol wire construction that is at least partially covered in a mesh material and that is movable between the compressed configuration and the expanded configuration, and wherein the second expandable frame of artificial valve comprises a second nitinol wire construction that is at least partially covered in a tissue material and that is expandable independently from the first expandable frame of the anchoring assembly.

19. The method of claim 18, wherein the plurality of projections of the anchor assembly comprise sub-annular projections that are positioned lower than the retention structure of the anchor assembly, and wherein the generally central hub is positioned lower than the sub-annular projections.

20. The method of claim 19, wherein said inserting the anchor assembly within the heart comprises inserting the anchor assembly into the left atrium via the anchor delivery catheter, and said inserting the anchor assembly within the heart comprises inserting the valve assembly into the left atrium via a valve delivery catheter after the anchor assembly engages with the sub-annular gutter of the mitral valve.

* * * * *